United States Patent

Suhadolnik et al.

[11] Patent Number: 5,863,905
[45] Date of Patent: Jan. 26, 1999

[54] 2',5'-PHOSPHOROTHIOATE/ PHOSPHODIESTER OLIGOADENYLATES AND ANTI-VIRAL USES THEREOF

[75] Inventors: Robert J. Suhadolnik, Roslyn, Pa.; Wolfgang Pfleiderer, Konstanz, Germany

[73] Assignee: Temple University-Of The Commonwealth System of Higher Education, Philadelphia, Pa.

[21] Appl. No.: 780,244

[22] Filed: Jan. 8, 1997

Related U.S. Application Data

[63] Continuation of Ser. No. 306,273, Sep. 14, 1994, abandoned.
[51] Int. Cl.⁶ .............................. A61K 31/70; C07H 21/00
[52] U.S. Cl. .......................... 514/44; 514/885; 514/889; 514/934; 536/25.2; 536/25.6; 536/26.4; 530/322; 530/395
[58] Field of Search .................. 536/25.2, 25.3, 536/25.34, 25.6; 530/322, 395; 514/44; 525/54.2

[56] References Cited

U.S. PATENT DOCUMENTS

| | | | |
|---|---|---|---|
| 4,378,352 | 3/1983 | Kimchi et al. ........................ 424/180 |
| 4,743,539 | 5/1988 | Gordon et al. ........................... 435/6 |
| 4,824,941 | 4/1989 | Gordon et al. ......................... 530/403 |
| 4,859,768 | 8/1989 | Suhadolnik et al. . | |
| 4,924,624 | 5/1990 | Suhadolnik et al. . | |
| 4,981,957 | 1/1991 | Leblev et al. ......................... 536/25.2 |
| 5,063,159 | 11/1991 | Revel et al. ........................ 435/252.3 |
| 5,071,963 | 12/1991 | Revel et al. ............................ 530/387 |
| 5,188,897 | 2/1993 | Suhadolnik et al. . | |
| 5,405,939 | 4/1995 | Suhadolnik et al. . | |
| 5,532,130 | 7/1996 | Alul ....................................... 435/6 |
| 5,550,111 | 8/1996 | Suhadolnik et al. . | |
| 5,556,840 | 9/1996 | Suhadolnik et al. . | |

OTHER PUBLICATIONS

Biochemistry, vol. 25, pp. 3730–3736 (1986).
Nucleic Acid Research, vol. 15, No. 23, pp. 9933–9943 (1987).
Inst. Bioorg. Khim., vol. 16, No. 11, pp. 1537–1544 (1990).
Sobol et al., *J. Interferon Res.* 12 (Suppl. 1), S.190 (1992).
Kon et al., *FASEB J.* (1), A332 (1992).

*Primary Examiner*—James O. Wilson
*Attorney, Agent, or Firm*—Seidel, Gonda, Lavorgna & Monaco, PC

[57] ABSTRACT

Optically active antiviral compounds having the formula

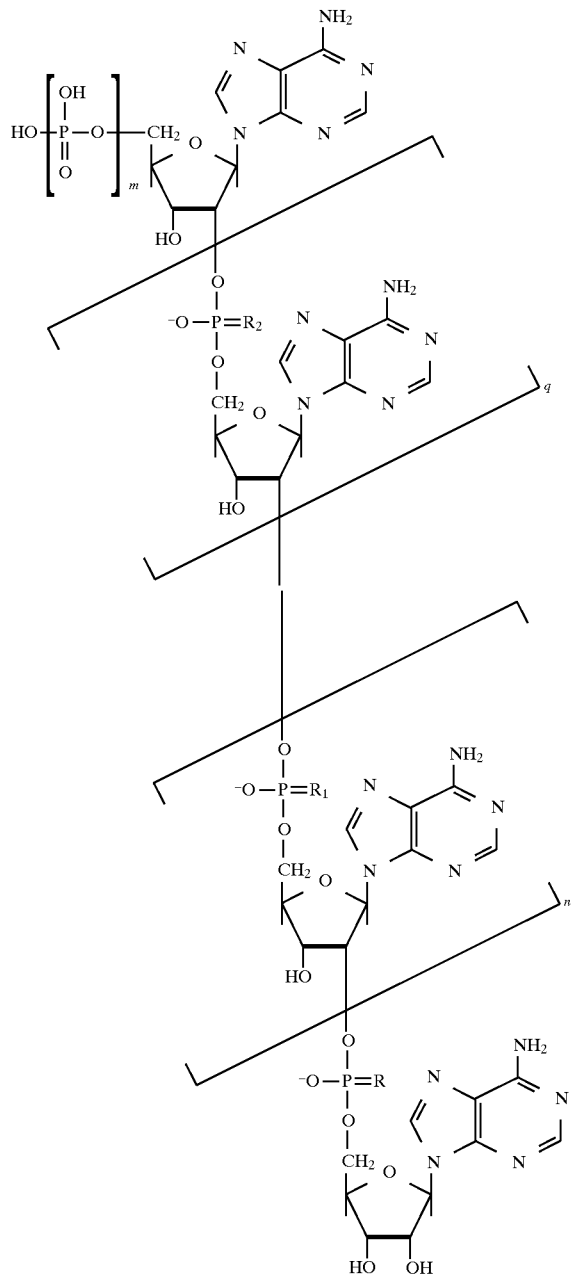

wherein m is 0, 1, 2, or 3; n and q are selected from the group of 0 and 1, provided that n and q may not both be zero; and R, $R_1$, and $R_2$ are independently of each other selected from the group consisting of oxygen and sulfur, provided that all R, $R_1$ and $R_2$, may not be oxygen, and further provided that all R, $R_1$, and $R_2$ may not be sulfur. The compounds possess increased antiviral activity and/or metabolic stability.

48 Claims, 8 Drawing Sheets

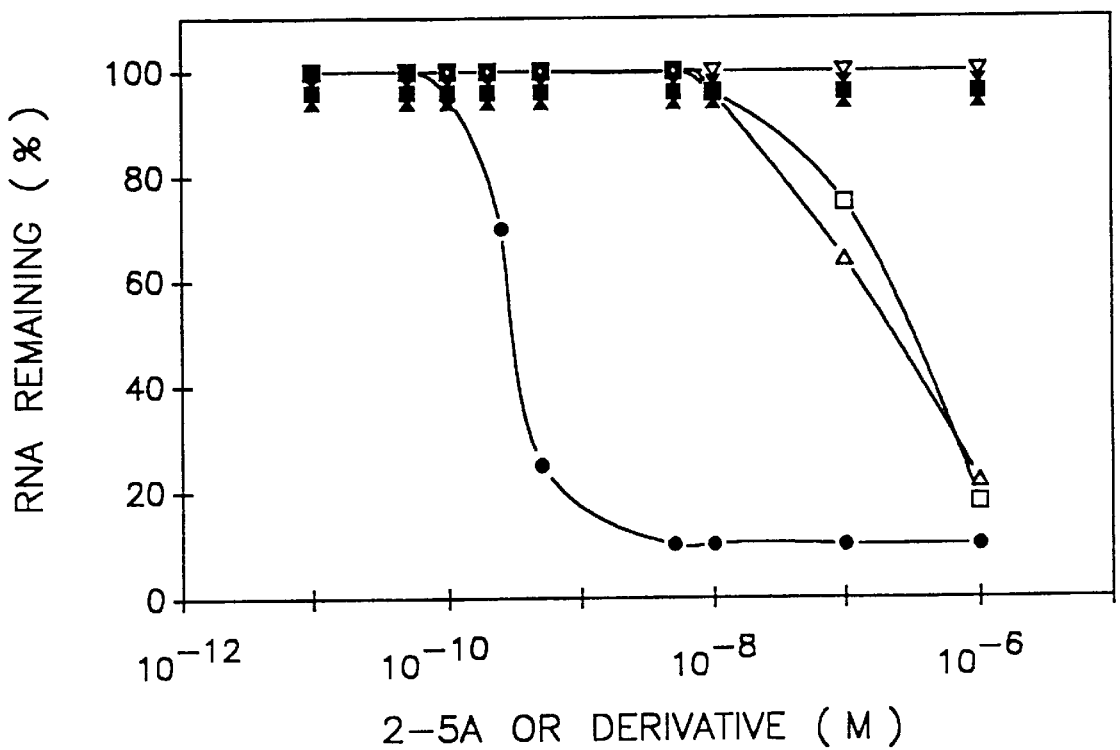
FIG.IC
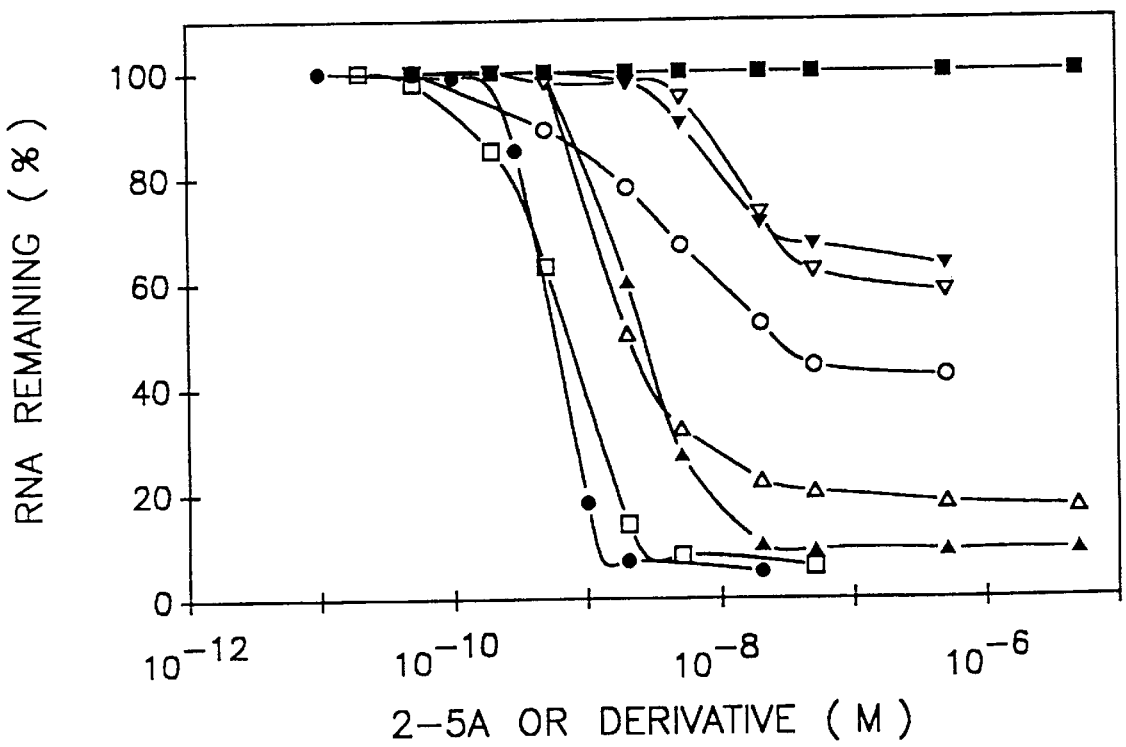
FIG.ID 5,863,905

2',5'-PHOSPHOROTHIOATE/ PHOSPHODIESTER OLIGOADENYLATES AND ANTI-VIRAL USES THEREOF

This is a continuation of application Ser. No. 08/306,273 filed on Sep. 14. 1994 now abandoned.

REFERENCE TO GOVERNMENT GRANT

The invention described herein was made, in part, in the course of work supported by National Science Foundation grant DMB-9004139 and U.S. Public Health Service grant P30-CA12227.

FIELD OF THE INVENTION

This invention relates to synthetic analogues of naturally occurring antiviral 2',5'-oligoadenylates wherein at least one of the internucleotide phosphodiester linkages is replaced with optically active phosphorothioate groups. The compounds with selected internucleotide phosphodiester linkages have antiviral activity and increased metabolic stability.

BACKGROUND OF THE INVENTION

The full nomenclature of the subject matter of the present invention involves lengthy terms. It is customary for those skilled in the art to abbreviate oligoadenylate analogues and related terms in a manner well-known to the art. These general and customary abbreviations are set forth herein below and may be utilized in the text of this specification.

Abbreviations 2-5A, 2',5'-oligoadenylate or $p_3A_n$: Oligomer of adenylic acid with 2',5'-phosphodiester linkages and a 5'-terminal triphosphate group.

$A_2$, $A_3$ and $A_4$: Dimer, trimer and tetramer of adenylic acid with 2',5'-phosphodiester linkages.

$pA_3$, $ppA_3$ (or $p_2A_3$), $pppA_3$ (or $p_3A_3$): 5'-terminal mono-, di- and triphosphates of $A_3$.

$pA_4$, $ppA_4$ (or $p_2A_4$), $pppA_4$ (or $p_3A_4$): 5'-terminal mono-, di- and triphosphates of $A_4$.

ApA: Dimer of adenylic acid with 2'-5'-phosphodiester linkage.

Ap*A: Dimer of adenylic acid with 2'-5'-phosphorothioate linkage.

PR: The R stereoconfiguration about a chiral phosphorous atom in a phosphorothioate internucleotide linkage.

PS: The S stereoconfiguration about a chiral phosphorous atom in a phosphorothioate internucleotide linkage.

$A_{Rp}$*ApA: (PR)-P-thioadenylyl-(2',5')-adenylyl-(2',5')-adenosine.

$A_{Sp}$*ApA: (PS)-P-thioadenylyl-(2',5')-adenylyl-(2',5')-adenosine.

Ap$A_{Rp}$*A: Adenylyl-(2',5')-(PR)-P-thioadenylyl-(2',5')-adenosine.

Ap$A_{Sp}$*A: Adenylyl-(2',5')-(PS)-P-thioadenylyl-(2',5')-adenosine.

$pA_{Rp}$*ApA, $ppA_{Rp}$*ApA, $pppA_{Rp}$*ApA, $pA_{Sp}$*ApA, $ppA_{Sp}$*ApA, $pppA_{Sp}$*ApA, $pApA_{Rp}$*A, $ppApA_{Rp}$*A, $pppApA_{Rp}$*A, $pApA_{Sp}$*A, $ppApA_{Sp}$*A, $pppApA_{Sp}$*A: 5'-mono-, di- and triphosphates of $A_{Rp}$*ApA, $A_{Sp}$*ApA, Ap$A_{Rp}$*A, and Ap$A_{Sp}$*A.

$A_{Rp}$*ApApA: (PR)-P-thioadenylyl-(2',5')-adenylyl-(2',5')-adenylyl-(2',5')-adenosine.

$A_{Sp}$*ApApA: (PS)-P-thioadenylyl-(2',5')-adenylyl-(2',5')-adenylyl-(2',5')-adenosine. Id.1 Ap$A_{Rp}$*ApA: Adenylyl-(2',5')-(PR)-P-thioadenylyl-(2',5')-adenylyl-(2',5')-adenosine.

Ap$A_{Sp}$*ApA: Adenylyl-(2',5')-(PS)-P-thioadenylyl-(2',5')-adenylyl-(2',5')-adenosine.

ApAp$A_{Rp}$*A: Adenylyl-(2',5')-(PR)-P-thioadenylyl-(2', 5')-adenylyl-(2',5')-adenosine.

ApAp$A_{Sp}$*A: Adenylyl-(2',5')-adenylyl-(2',5')-(PS)-P-thioadenylyl-(2',5')-adenosine.

$pA_{Rp}$*ApApA, $ppA_{Rp}$*ApApA, $pppA_{Rp}$*ApApA, $pA_{Sp}$*ApApA, $ppA_{Sp}$*ApApA, $pppA_{Sp}$*ApApA, $pApA_{Rp}$*ApA, $ppApA_{Rp}$*ApA, $pppApA_{Rp}$*ApA, $pApA_{Sp}$*ApA, $ppApA_{Sp}$*ApA, $pppApA_{Sp}$*ApA, $pApApA_{Rp}$*A, $ppApApA_{Rp}$*A, $pppApApA_{Rp}$*A, $pApApA_{Sp}$*A, $ppApApA_{Sp}$*A, $pppApApA_{Sp}$*A: 5'-mono-, di- and triphosphates of the above tetramers.

bz: benzoyl ce: cyanoethyl

CFS: Chronic Fatigue Syndrome

DEAE: 2-(diethylamino)ethyl

DBU: 1.8 diazabicyclo[5.3.0]undec-7-enc

HIV: Human Immunodeficiency Virus

MeOTr: monomethoxytrityl

M.O.I: multiplicity of infection mRNA: Messenger RNA npe: 2-(4-niytophenyl)ethyl PBL: Peripheral blood lymphocytes pCp: Cytidine 3'-5'-bisphosphate (PS)-ATP-alpha-S: Adenosine 5'O—(PS)-(1-thiotriphosphate).

RNase L: 2-5A-dependent endoribonuclease.

rRNA: Ribosomal RNA

RT: Reverse transcriptase

SCP: Specific cleavage products tbds: (tert-butyl)dimethylsilyl

Tris: tris(hydroxymethyl)aminomethane tRNA: Transfer RNA

It is generally regarded that activation of RNase L by 2-5A is key to the antiviral defense mechanisms. Interferon induces transcription of the enzyme 2-5A synthetase which produces 2',5' linked oligoadenylates upon activation of double-stranded RNA. Previously, the only known biochemical effect of 2-5A is activation of RNase L. This enzyme hydrolyses mRNA and rRNA, thereby resulting in inhibition of protein synthesis. The activation of RNase L is transient unless 2-5A is continuously synthesized, since 2-5A is rapidly degraded. RNase L activation thus plays a critical role in inhibiting replication, and therefore in defending against infection by viruses.

A correlation has also been established between 2-5A metabolism and the growth cycle of HIV-1, i.e., high levels of 2-5A and activated RNase L correlate with failure of infected cells to release HIV-1, Schröder et al., *J. Biol. Chem.* 264: 5669–5673 (1989). Conversely, when the intracellular 2-5A pool decreases, RNase L can not be activated and HIV-1 production increases. A role for 2-5A cores as inhibitors of HIV-1 replication has been established with reports that 2-5A trimer and tetramer cores, 5'-monophosphates and 5'-triphosphates inhibit HIV-1 reverse transcriptase/primer complex formation, Montefiori et al., *Proc. Natl. Acad. Sci. USA* 86: 7191–7194 (1989); M üller et al., *Biochemistry* 30: 2027–2033 (1991); Sobol et al., *Biochemistry* 32: 1211–12118 (1993).

The introduction of the phosphorothioate group in the 2',5'-internucleotide linkages of 2-5A, induces metabolic stability greater than authentic 2-5A and resulted in the first 2-5A cores (i.e. 2-5A lacking 5'-phosphate moieties) able to activate RNase L (Kariko et al. *Biochemistry* 26: 7136–7142

(1987); Charachon et al. *Biochemistry* 29: 2550–2556 (1990)). Further, RNase L is a functionally stereoselective enzyme and 2-5A trimers and tetramers having at least one of the internucleotide phosphorothioate 2',5'-linkages of the PS configuration have greatly enhanced metabolic stability. The chemical synthesis of the fully resolved 2',5'-phosphorothioate adenylate trimer and tetramer cores has been reported, Suhadolnik et al., U.S. Pat. No. 4,924,624. Preparation of the stereoisomers via enzymatic synthesis is not possible due to the sterospecificity of 2-5A synthetase for the substrate (PS)-ATP-alpha-S, which yields trimer and tetramer products of the PR configuration exclusively. Further, while Lebleu et al., U.S. Pat. No. 4,981,957, discloses the enzymatic synthesis of a phosphorothioate-substituted derivative of 2',5' oligoadenylate, the compounds disclosed are not stereospecific.

SUMMARY OF THE INVENTION

Compounds of the present invention useful in inhibiting viral infections in plants and mammals have increased metabolic stability and/or antiviral activity.

The compounds and the water-soluble salts thereof are of the formula

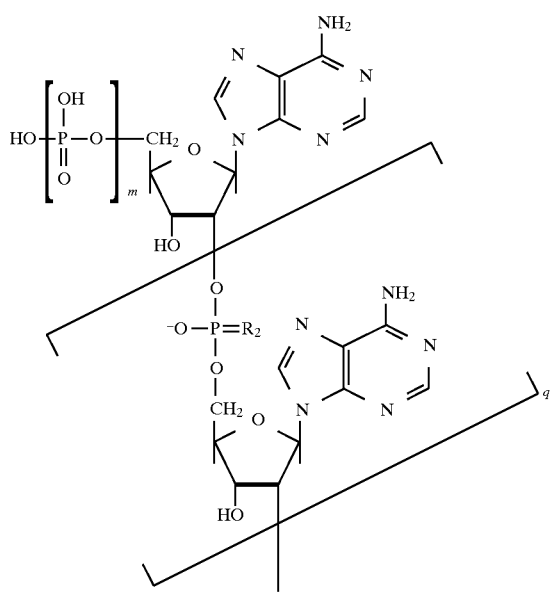

-continued

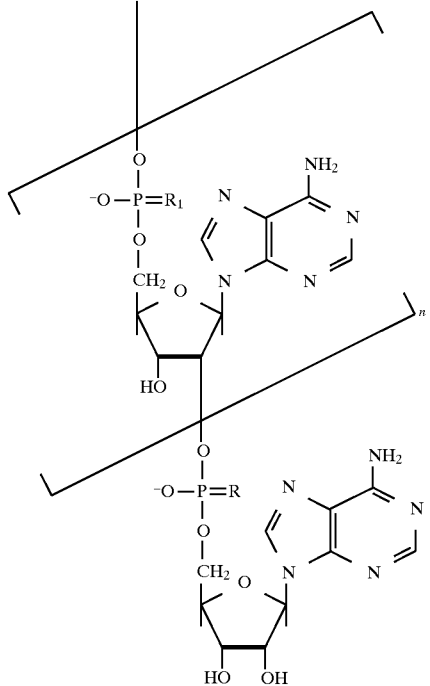

wherein m is zero, 1, 2 or 3; n and q are selected from the group of zero and 1, provided that n and q may not both be zero; and R, $R_1$ and $R_2$ are independently selected from the group of oxygen and sulfur, provided that all R, $R_1$ and $R_2$, may not be oxygen, and further provided that all R, $R_1$ and $R_2$ may not be sulfur.

The invention also comprises a method of inhibiting viral infection in mammals or plants by administering an antivirally effective amount of a compound according to the above formula, or a water-soluble salt thereof, and antiviral compositions containing such compounds with a carrier.

Compounds according to the formula wherein n is 1 and q is 1 may be utilized to form oligoadenylate conjugates with the macromolecular carrier poly(L-lysine) for intracellular transport. Such poly(L-lysine)/2',5'-phosphorothioate/phosphodiester oligoadenylate conjugates have the formula

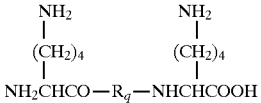

wherein q is an integer from about 60 to about 70, and R is randomly R' or

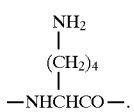

From about five to about ten of the R groups comprise R'. R' has the following formula wherein m is 0, 1, 2 or 3; and where each $R_3$, $R_4$, or $R_5$ are independently selected from the group of oxygen and sulfur; provided that all $R_3$, $R_4$ or $R_5$ may not be oxygen; and further provided that all $R_3$, $R_4$ or $R^5$, may not be sulfur.

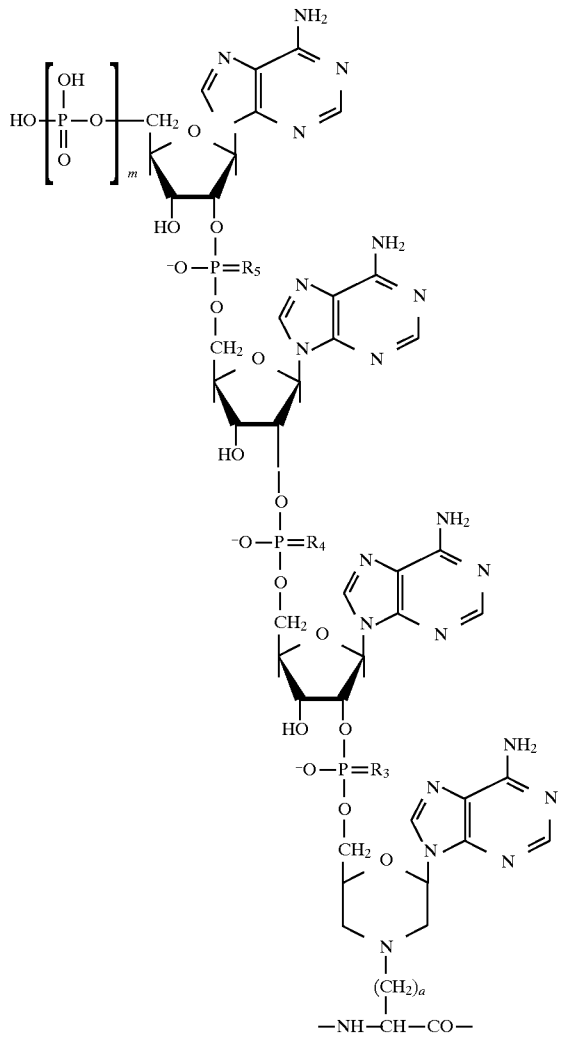

Preferably, at least one of the internucleotide phosphorothioate groups

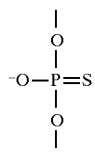

of the poly(L-lysine)/2',5'-phosphorothioate/phosphodiester oligoadenylate conjugates is of the PR configuration.

DESCRIPTION OF THE FIGURES

FIG. 1C represents the results of a radiobinding assay performed according to the method of FIG. 1A for 2',5'-phosphorothioate/phosphodiester tetramer core-2-5A derivatives. The curves are labeled as follows: $p_3A_4$ (●); $A_{Rp}$*ApApA (▽); $A_{Sp}$*ApApA (▼); $ApA_{Rp}$*ApA (□); $ApA_{Sp}$*ApA (■); $ApApA_{Rp}$*A (△); and $ApApA_{Sp}$*A (▲).

FIG. 1D represents the results of a radiobinding assay performed according to the method of FIG. 1A for 2',5'-phosphorothioate/phosphodiester tetramer 5'-monophosphate 2-5A derivatives. The curves are labeled as follows: $p_3A_4$ (●); $pA_4$ (○); $pA_{Rp}$*ApApA (▽); $pA_{Sp}$*ApApA (▼); $pApA_{Rp}$*ApA (□); $pApA_{Sp}$*ApA (■); $pApApA_{Rp}$*A (△); and $pApApA_{Sp}$*A (▲).

DETAILED DESCRIPTION OF THE INVENTION

The individual nucleotide linkages of the trimer and tetramer derivatives of 2',5'-oligoadenylate (2-5A) were stereochemically modified via phosphorothiate substitution by phosphotriester and phosphoramidite chemical synthesis. The approach described herein utilizes fully protected monomeric building blocks (Schemes 1 and 2 below, which can be individually manipulated. The protecting groups remain in place during the chemical synthesis of the oligonucleotide chain and are removed at the end of the sequence by β-elimination.

The phosphorothioate/phosphodiester trimer cores, A$_{Rp}$*ApA 10, A$_{Sp}$*ApA 11, ApA$_{Rp}$*A 23, and ApA$_{Sp}$*A 24, were chemically synthesized and separated by preparative thin layer chromatography on silica gel, deblocked and purified by applying the residue on a DEAE Sephadex column. The four trimer cores are prepared from phosphoramidite intermediates 4 and 15. The synthesis relies on separation of fully resolved protected intermediates, 8, 9, 21 and 22 followed by removal of all blocking groups to yield the individually substituted 2',5'-phosphorothioate/phosphodiester trimer adenylate cores. While not part of the invention, the preparation of the dimer core 6 is included for completeness.

The selectively substituted tetramer cores, 38 and 39, 51 and 52 and 57 and 58, were derived from the fully protected trimer cores, 30 and 31, and subsequently subjected to detrilylation and condensation to add the tetramer moiety.

The compounds of the present invention comprise 2-5A derivatives that are (i) nuclease-resistant, (ii) non-toxic, (iii) able to activate or inactivate RNase L and (iv) able to inhibit HIV-1 replication. The inventive compounds are chemically synthesized phosphorothioate/phosphodiester trimer and tetramer 2-5A derivatives in which at least one 2',5'- phosphodiester bond has been selectively replaced with a 2',5'-phosphorothioate bond. The chemical synthesis of these phosphorothioate/phosphodiester derivatives utilizes the phosphotriester and phosphoramidite approach in which reactive functional groups are protected by blocking groups which can be individually manipulated. The phosphorothioate/phosphodiester trimer and tetramer 2-5A derivatives reveal heretofore unknown aspects of the stereochemical requirements for activation of RNase L, namely, that activation of RNase L requires PR chirality in the second internucleotide linkage from the 5'-terminus of the 2-5A molecule and that PS chirality in the second internucleotide linkage results in 2-5A derivatives that are antagonists of RNase L activation. Without wishing to be bound by any theory, it appears that PR chirality in the second internucleotide linkage from the 5'-terminus may serve to facilitate formation of a productive complex between RNase L, the allosteric activator (ApA$_{Rp}$*A or ApA$_{Rp}$*ApA) and the RNA substrate such that hydrolysis of HIV-1 RNA can occur.

Figure 4A:
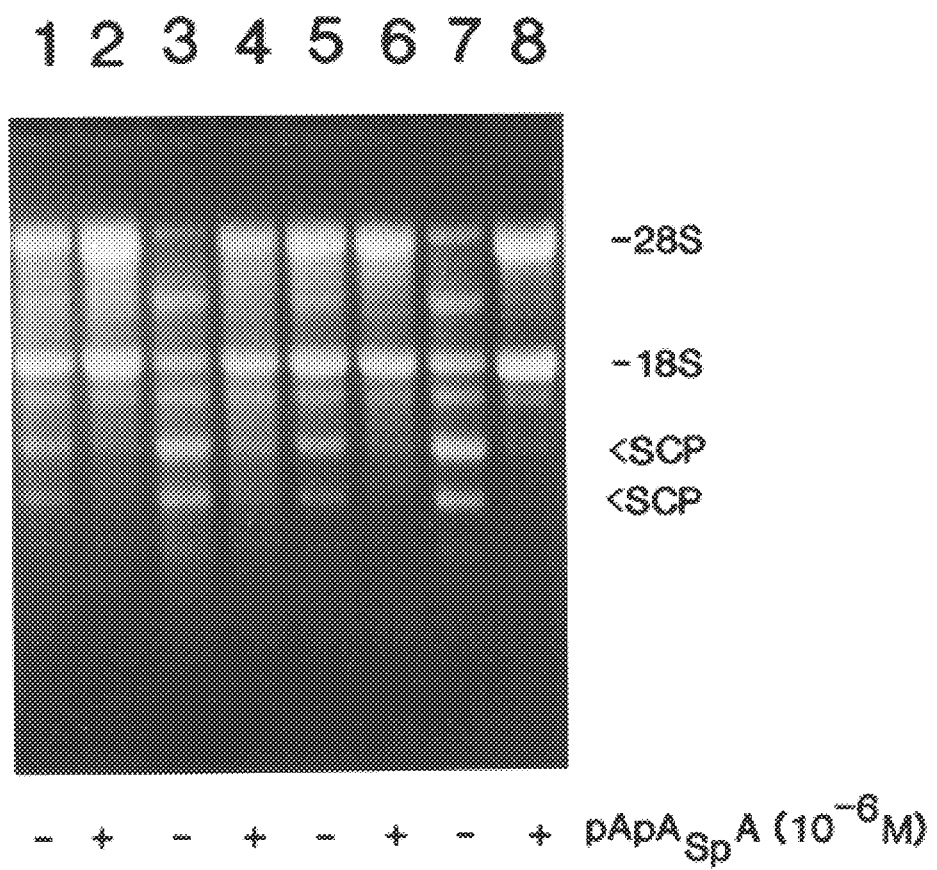
FIG. 4A represents the results of a ribosomal cleavage assay performed according to the method of FIG. 2A, indicating the inhibition of activation of RNase L by pApA$_{Sp}$*A in L929 cell extracts and by partially-purified RNase L. L929 cell extracts were incubated in the presence of p$_3$A$_3$ at $10^{-9}$M (lanes 1 and 2), P$_3$A$_3$ at $10^{-8}$M (lanes 3 and 4) pApA$_{Rp}$*A, at $10^{-9}$M (lanes 5 and 6), pApA$_{Rp}$*A at $10^{-8}$M (lanes 7 and 8), and pApA$_{Sp}$*A at $10^{-6}$M (lanes 2, 4, 6 and 8).
Figure 4B:
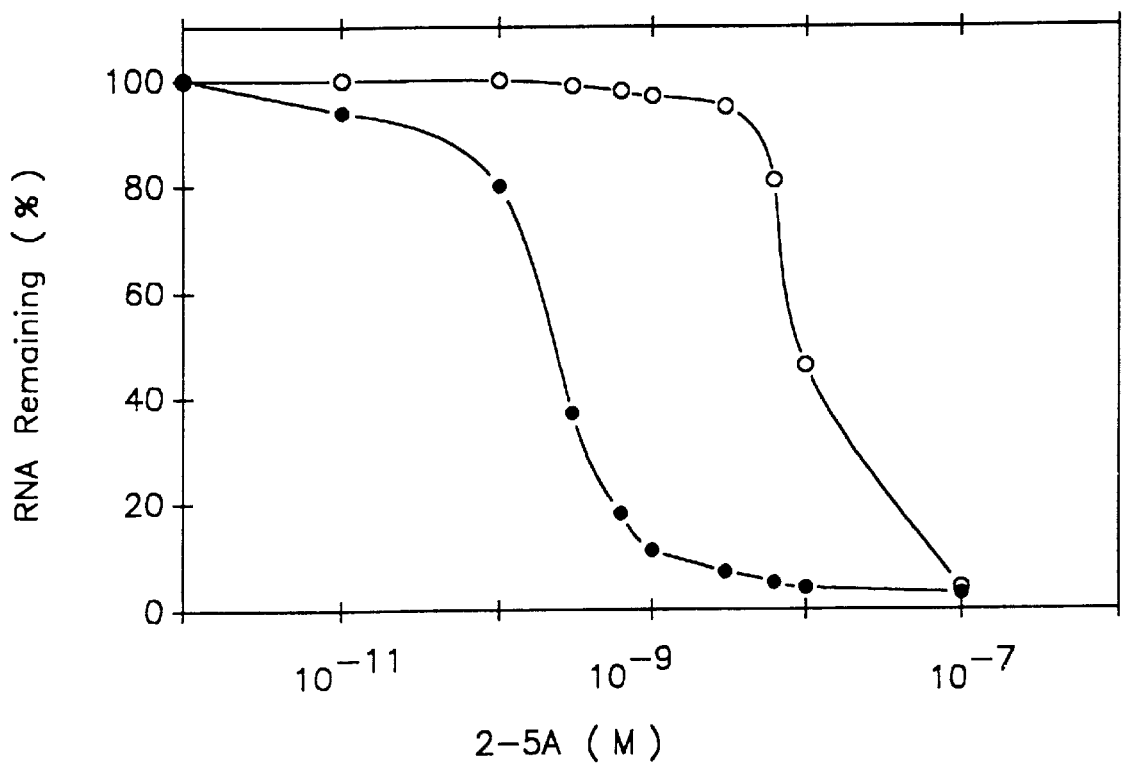
FIG. 4B represents the results of a radiobinding assay indicating the activation of RNase L partially-purified from L929 cell extracts. Activation of RNase L was determined by the conversion of poly(U) [$^{32}$P]pCp to acid-soluble fragments by immobilization on 2-5A$_4$ core-cellulose. 100% represents 25,000 dpm of poly(U) [32P]pCp bound to glass fiber filters. 2-5 A oligomer (phosphodiester internucleotide linkage) is also included for comparison. The curves are labeled as follows: p$_3$A$_3$ (●); p$_3$A$_3$+pApA$_{Sp}$*A at $10^{-6}$M (○).

Phosphorothioate substitution of individual internucleotide linkages in the 2-5A molecule has revealed that inhibition of HIV-1 replication is influenced by the location and stereoconfiguration of the chiral phosphorothioate group in the phosophorothioate/phosphodiester derivatives. Of the four phosphorothioate/phosphodiester trimer core derivatives, ApA$_{Rp}$*A and ApA$_{Sp}$*A were the most efficient inhibitors of HIV-1 induced syncytia formation (FIG. 4A). Of the six phosphorothioate/phosphodiester tetramer core derivatives, ApApA$_{Rp}$*A and ApApA$_{Sp}$*A were the most efficient inhibitors (FIG. 4B). A$_{Rp}$*A, A$_{Sp}$*A, 3',5'-A$_4$, adenosine and adenine did not inhibit HIV-1 RT activity. Whereas ApA$_{Rp}$*A and ApA$_{Sp}$*A are both phosphodiesterase-resistant and inhibit HIV-1 RT, the ApA$_{Rp}$*A enantiomer (but not the ApA$_{Sp}$*A enantiomer) can also activate RNase L.

In this regard it appears, again, without wishing to be bound by any theory, that the relative differences in the inhibition of HIV-1 replication by the phosphorothioate/phospohodiester trimer and tetramer core derivatives may be explained by their resistance to hydrolysis by serum phosphodiesterases (see Table 1, infra.). In contrast to 2',5'-phosphodiester bonds in authentic A$_2$ and A$_3$ which are totally hydrolyzed in serum-containing medium in 20 minutes, both PR and PS 2',5'-phosphorothioate bonds are more stable to hydrolysis by phosphodiesterases. The phosphorothioate/phosphodiester tetramer core derivatives which are stereochemically modified at the 5'-terminus (A$_{Rp}$*ApApA and A$_{Sp}$*ApApA) are rapidly hydrolyzed from the 2',3'-terminus to their respective dimers, A$_{Rp}$*A and A$_{Sp}$*A. These dimers, although resistant to further hydrolysis, can neither activate RNase L nor inhibit HIV-1 replication. The remaining four phosphorothioate/phosphodiester tetramer core derivatives (ApA$_{Rp}$*ApA, ApA$_{Sp}$*ApApA$_{Rp}$*A and ApApA$_{Sp}$*A) are hydrolyzed from the 5'-terminus to form their respective trimer cores, A$_{Rp}$*ApA, A$_{Sp}$*ApA, ApA$_{Rp}$*A and ApA$_{Sp}$*A, respectively. Because ApA$_{Rp}$*A and ApA$_{Sp}$*A are efficient inhibitors of HIV-1 replication, this hydrolysis most likely accounts for the antiviral action of the tetramer derivatives, ApApA$_{Rp}$*A and ApApA$_{Sp}$*A. Therefore, the decreased anti-HIV-1 activity observed with ApA$_{Rp}$*ApA and ApA$_{Sp}$*ApA (relative to ApApA$_{Rp}$*A and ApApAp$_{Sp}$*A) is likely due to hydrolysis from the 5'-terminus to form ApA$_{Rp}$*A and ApA$_{Sp}$*A, which are very efficient inhibitors of HIV-1 induced syncytia formation (compare FIGS. 4A and 4B).

In preliminary experiments, all phosphorothioate/phosphodiester trimer and tetramer 2-5A core derivatives of the present invention have been shown to inhibit HIV-1 RT. Inhibition ranges from 22% to 70%. $A_{Rp}*A$, $A_{Sp}*A$, 3',5'-$A_4$, adenosine and adenine did not inhibit HIV-1 RT activity. Whereas $ApA_{Rp}*A$ and $ApA_{Sp}*A$ are both phosphodiesterase-resistant and inhibit HIV-1 RT, the $ApA_{Rp}*A$ enantiomer (but not the $ApA_{Sp}*A$ enantiomer) can also activate RNase L.

These three biological properties (i.e., resistance to hydrolysis by phospohodiesterases, inhibition of reverse transcriptase and activation of RNase L) may account for the 100% inhibition of HIV-1 replication observed with $ApA_{Rp}*A$.

The compounds of the invention are advantageously prepared as soluble salts of sodium, ammonium or potassium. The preparative scheme begins with 6-N-benzoyl-3'-O-tert-butyldimethylsilyl-5'-O-monomethoxy-trityladenosine 1, which is advantageously prepared from adenosine according to the procedure of Flockerzi et al., *Liebig's Ann. Chem.*, 1568–1585 (1981). Preparation of the compounds of the present invention is illustrated in more detail by reference to the following non-limiting examples.

3-Nitro-1,2,4-triazole and p-nitrophenylethanol used in the examples may be prepared advantageously from published procedures: Chattopadhyaya et al., *Nucleic Acids Res.* 8:2039–2053 (1980); Schwarz et al., *Tetrahedron Lett.*, 5513–5516 (1984); Uhlmann et al., *Helv. Chim. Acta* 64:1688–1703 (1981). These compounds are also available commercially in the United States. 3-Nitro-1,2,4-triazole is available from Aldrich Chemical Co., P.O. Box 355, Milwaukee, Wis. 53201 (1986–1987 cat. no. 24,179.2).

p-Nitrophenylethanol is available from Fluka Chemical Corp. (cat. no. 73,610).

Pyridine and triethylamine used in the examples were purified by distillation over KOH, tosyl chloride and calcium hydride. Dichloromethane was distilled over calcium chloride and then passed through basic alumina. Pure acetonitrile was obtained by distillation over calcium hydride.

Purification of the protected nucleotides was achieved by preparative column chromatography on silica gel 60 (0.063–0.2 mesh, Merck) and by preparative thick layer chromatography on silica gel 60 $PF_{254}$ (Merck). Thin layer chromatography ("TLC") was carried out on precoated thin layer sheets F 1500 LS 254 and cellulose thin layer sheets F 1440 from Schleicher & Scheull.

Scheme 1 is the reaction scheme for the preparation of the fully resolved trimers, having phosphorothioate substitution of the first internucleotide linkage $A_{Rp}*ApA$ 10 and $A_{Sp}*ApA$ 11, from the protected intermediates, 8 and 9, wherein "bz" denotes the benzoyl radical, "tbds" denotes the tert-butyldimethylsilyl radical, "ce" denotes the cyanoethyl radical, "npe" denotes the nitrophenylethoxy radical and "MeOTr" represents the monomethoxytrityl radical. The preparation of the trimer cores, 10 and 11 is set forth in Preparations 1 through 4 and Example 1. Preparation 4 illustrates the fully protected trimer core, while Example 1 illustrates the removal of the blocking groups and the chemical purification of the fully resolved isomers.

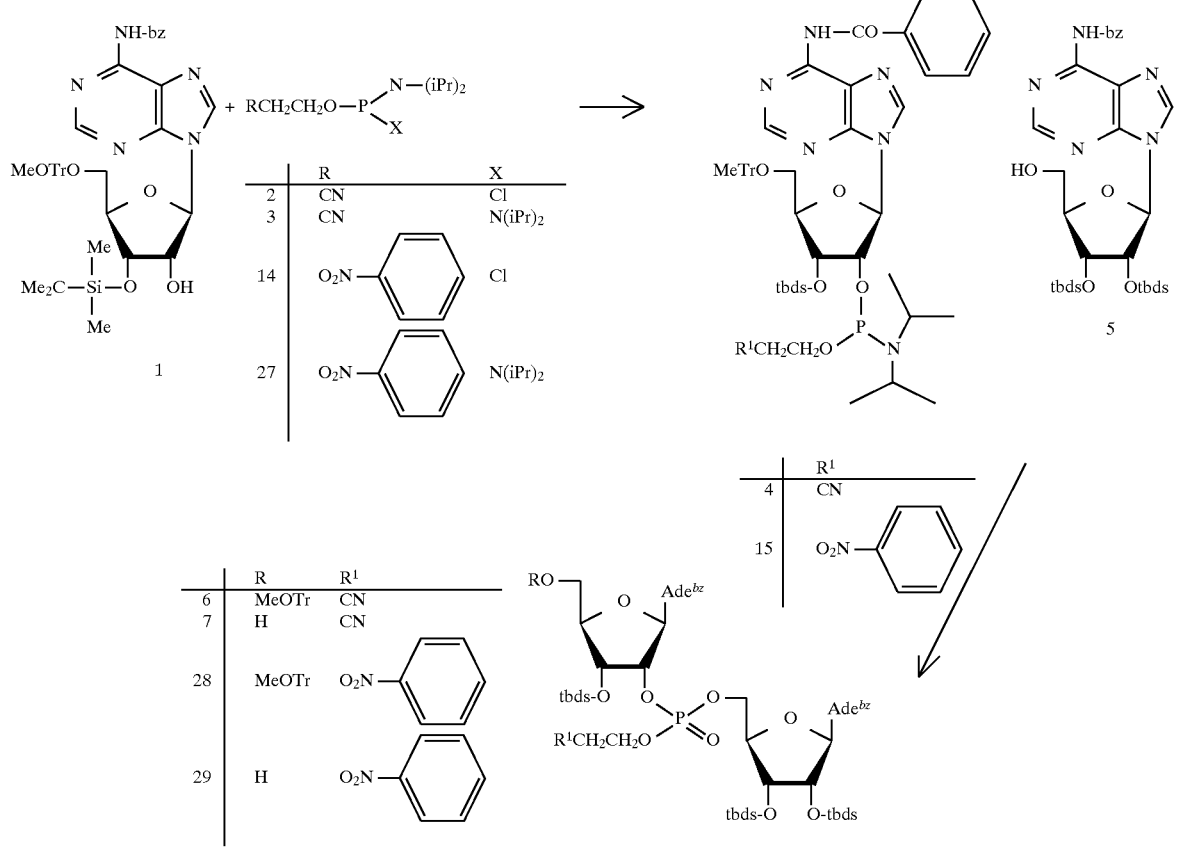

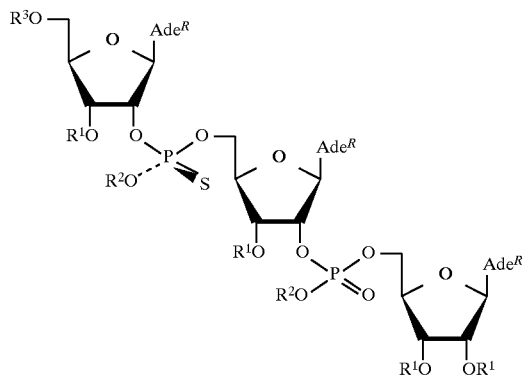

| | R | R¹ | R² | R³ |
|---|---|---|---|---|
| 8 | bz | tbds | ce | MeOTr |
| 10 | H | H | NH₄ | H |
| 12 | H | H | NH₄ | PO₃(NH₄)₂ |
| 30 | bz | tbds | npe | MeOTr |
| 32 | bz | tbds | npe | H |

-continued

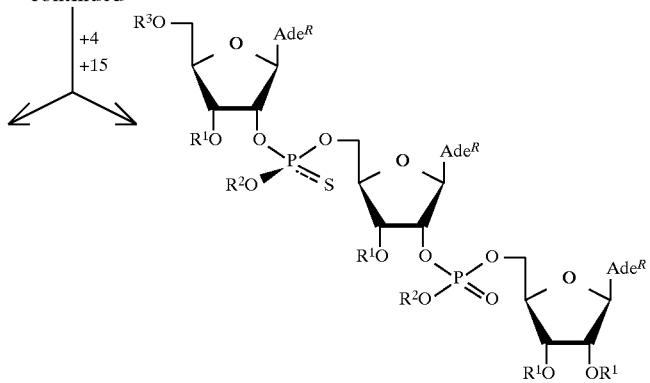

| | R | R¹ | R² | R³ |
|---|---|---|---|---|
| 9 | bz | tbds | ce | MeOTr |
| 11 | H | H | NH₄ | H |
| 13 | H | H | NH₄ | PO₃(NH₄)₂ |
| 31 | bz | tbds | npe | MeOTr |
| 33 | bz | tbds | npe | H |

PREPARATION 1 a. Bis-(diisopropylamino)-(β-cyanoethoxy) phosphane 3

Preparation of the titled compound was in accord with the procedure of Kraszewski & Norris, *Nucleic Acids Research Sump. Ser.* 18: 177–80 (1987). β-Cyanoethanol (7 g; 0.1 mole) in absolute $CH_3CN$ (40 ml was added dropwise within 30 min to a solution of freshly distilled $PCl_3$ (40 ml; 0.4 mole) at room temperature ("r.t.") and under nitrogen atmosphere. After stirring for 3.5 h, the solvent and excess $PCl_3$ were removed in high vacuum, the residue was dissolved in 450 ml of absolute ether and at $-10°$ C. reacted with N,N-diisopropylamine (127 ml; 0.9 mole) by dropwise addition within 1 h under nitrogen atmosphere. The reaction mixture was stirred at $-10°$ C. for 30 min and at r.t. for 15 h. The precipitate was filtered under nitrogen and the solvent was removed in vacuo. The yellow crude product was fractionally distilled over $CaH_2$ to give 14.7 g (49%) of pure 3 of b.p. 114°–118° C. This reagent was stored at $-20°$ C. under nitrogen. $^1$H-NMR ($CDCl_3$): 3.75 (s, 2H, $CH_2$); 3.52 (m, 4H, 4 N—CH); 2.60 (t, 2H, β-$CH_2$); 1.17+1.14 (2d, 24H, 4 N—$C(CH_3)_2$). $^{31}$P-NMR ($CDCl_3$): 124.6 ppm.

b. 6-N-Benzoyl-3'-O-[(tert-butyl)dimethylsilyl]-5'-O-(monomethoxytrityl)-adenosine-2'-O-[(β-cyanoethyl)-N,N-diisopropylamino]-phosphoramidite 4

METHOD A

The preparation of the titled compound was in accord with the procedures of Sinha et al., *Nucleic Acids Res.* 12: 4539–4557 (1984) wherein compound 1, Flockerzie et al. (1981), supra, (3.79 g; 5 mmole) and diisopropyl-ethylamine (3.5 ml) were dissolved in dry $CH_2Cl_2$ (20 ml) and chloro-N,N-diisopropylaminocyanoethoxy phosphane (2.37 g; 10 mmole) was added. After 1.5 h stirring under nitrogen at r.t., the reaction mixture was diluted with EtOAc (100 ml) and the organic phase was washed with a saturated $NaHCO_3$/NaCl solution (2×80 ml). The organic layer was dried over $Na_2SO_4$, filtered and evaporated to dryness. The residue was dissolved in $CH_2Cl_2$ (10 ml) and added dropwise to n-hexane (200 ml) at $-60°$ C. The product was collected and evaporated to dryness in high vacuum for 8 h to give 4.3 g (89%) of a colorless amorphous solid.

METHOD B

Alternatively, the titled compound was prepared according to the procedure of Kraszewski and Norris (1987), supra. In this method compound 1 (3.79 g; 5 mmole) and tetrazole (0.175 g; 2.5 mmole) were dissolved in dry $CH_2Cl_2$ (20 ml) and then bis-(diisopropylamino)-(β-cyanoethoxy) phosphane 3 (3 g; 10 mmole) was added. After stirring at r.t. under argon for 17 h, the reaction mixture was extracted with EtOAc (100 ml) and washed with saturated $NaHCO_3$/NaCl solution (80 ml). This was repeated twice and work-up was performed analogous to method A to give 4.49 g (94%) of a colorless amorphous powder. Anal. calc. for $C_{52}H_{64}N_7O_7PSi×2$ $H_2O$ (994.2): C 62.82, H 6.89, N 9.86. Found: C 62.52, H 7.08, N 10.35. UV (MeOH): $\lambda_{max}$ (logε) 279 nm (4.33); 229 nm (4.43). $R_f$ on silica gel with toluol/EtOAc (1/1, v/v): 0.64, 0.61 (diastereomers). $^{31}$P-NMR ($CDCl_3$): 150.98, 151.34.

PREPARATION 2

6-N-Benzoyl-3'-O-[(tert-butyl)dimethylsilyl]-5'-O-(monomethoxytrityl)-adenylyl-2'-[O$^P$-(2-cyanoethyl)-5'-]-6-N-benzoyl-2',3'-di-O-[(tert-butyl)dimethylsilyl]-adenosine 6

The phosphoramidite 4 (2.88 g; 3 mmole) and 6-N-benzoyl-2',3'-di-O-[(tert-butyl)dimethylsilyl]adenosine 5, Flockerzie et al. (1981), supra, (1.2 g; 2 mmole) were dried at r.t. in high vacuum for 24 h and dissolved in dry $CH_2Cl_2$ (30 ml). Tetrazole (0.5 g; 8 mmole) was added and after 3 h stirring at r.t. under argon, a solution of $I_2$ [0.5 g $H_2O$/pyridine/$CH_2Cl_2$ (1/3/1, v/v/v)] was added dropwise until the brown color does not disappear. The mixture was stirred for 15 min, then diluted with $CHCl_3$ (300 ml). The organic phase was saturated with $Na_2S_2O_3$/NaCl (3×80 ml), dried over $Na_2SO_4$ and evaporated to dryness. Final coevaporation was done with toluene (3×20 ml). The crude product was purified by silica gel column chromatography (15×2.5 cm) using $CHCl_3$ (100 ml), $CHCl_3$/MeOH (100/0.5, v/v; 1.5 L) and $CHCl_3$/MeOH: (100/1, v/v) to elute the product. Product fractions were collected and evaporated to dryness to give 2.33 g (79%) of the dimer 6 in the form of a solid foam. Anal. calc. for $C_{75}H_{94}N_{11}O_{13}PSi_3$ (1490.9): C 60.42, H 6.49, N 10.33. Found: C 60.50, H 6.49, N 10.22. UV (MeOH): $\lambda_{max}$ (logε) 278 nm (4.62), 230 nm (4.62). $R_f$ on silica gel with CHCl$_3$/MeOH (95/5, v/v)=0.56. $^{31}$P-NMR (CDCl$_3$): −0.74 and −1.07 ppm (diastereomers).

PREPARATION 3

6-N-Benzoyl-3'-O-[(tert-butyl)dimethylsilyl]-
adenylyl-2'-[O$^P$-(2-cyanoethyl)-5']-6-N-benzoyl-2',
3'-O-di-[(tert-butyl)dimethylsilyl]adenosine 7

Compound 6 (2.22 g; 1.51 mmole) was stirred with 2% p-TsOH in CH$_2$Cl$_2$/MeOH (4/1, v/v; 30 ml) at r.t. for 30 min. The reaction mixture was diluted with CH$_2$Cl$_2$ (300 ml), washed with phosphate buffer, pH 7.0 (2×100 ml), dried over Na$_2$SO$_4$ and evaporated to dryness. The residue was applied to a silica gel column (9×4.5 cm), washed with CHCl$_3$ (0.7 L) and CHCl$_3$/MeOH (100/1, v/v; 300 ml). The product was eluted with CHCl$_3$/MeOH (50/1, v/v; 300 ml and 100/3, v/v; 300 ml). The combined product fractions were evaporated to dryness in high vacuum to give 11.65 g (90%) of 5'-hydroxy dimer 7 as an amorphous solid. Anal. calc. for C$_{55}$H$_{78}$N$_{11}$O$_{12}$PSi$_3$×H$_2$O (1218.5): C 54.21, H 6.62, N 12.64. Found: C 54.53, H 6.58, N 12.62. UV (MeOH): $\lambda_{max}$ (logε) 278 nm (4.60), 232 nm (4.42.). R$_f$ on silica gel with CHCl$_3$/MeOH (95/5, v/v)=0.36. $^{31}$P-NMR (CDCl$_3$): −0.77 and −1.30 ppm (diastereomers).

PREPARATION 4 a. 6-N-Benzoyl-3'-O-[(tert-butyl)dimethylsilyl]-5'-
O-(monomethoxytrityl)-(PR)-thioadenylyl-2'-[O$^P$-
(2-cyanoethyl)-5']-6-N-benzoyl-3'-O-[(tert-butyl)
dimethylsilyl]-adenylyl-2'-[O$^P$-(2-cyanoethyl)-5']-6-
N-benzoyl-2',3'-di-O-[(tert-butyl)dimethylsilyl]-
adenosine A$_{Rp}$*ApA 8 b. 6-N-Benzoyl-3'-O-[(tert-butyl)dimethylsilyl]-5'-
O-(monomethoxytrityl)-(PS)-thioadenylyl-2'-[O$^P$-(2-
cyanoethyl)-5']-6-N-benzoyl-3'-O-[(tert-butyl)
dimethylsilyl]-adenylyl-2'-[O$^P$-(2-cyanoethyl)-5']-6-
N-benzoyl-2',3'-di-O-[(tert-butyl)dimethylsilyl]-
adenosine A$_{Sp}$*ApA 9

The phosphoramidite 4 (2.79 g; 2.92 mmole), the 5'-hydroxy dimer 7 (1.94 g; 1.62 mmole) and tetrazole (0.567 g; 8.1 mmole) were dissolved in dry CH$_3$CN (8.1 ml) and stirred at r.t. under nitrogen. After 3 h, S$_8$ (1.66; 6.48 mmole) and pyridine (7.8 ml) were added and stirred further for 20 h at r.t. The reaction mixture was then diluted with CH$_2$Cl$_2$ (300 ml), washed with saturated NaCl (2×200 ml), dried over Na$_2$SO$_4$ and evaporated to dryness. Final coevaporation was with toluene (3×20 ml). The crude diastereomeric mixture (A$_{Rp}$*ApA 8+A$_{Sp}$*ApA 9) was dissolved in CH$_2$Cl$_2$ and applied to a silica gel column (21×3.5 cm). The column was washed with CH$_2$Cl$_2$ (450 ml) and CH$_2$Cl$_2$/MeOH (99/1, v/v; 200 ml) and the product was eluted with CH$_2$Cl$_2$/MeOH (97/3, v/v; 400 ml). The product fractions were collected and evaporated to dryness to give 3.16 g (93%) of an isomeric mixture of A$_{Rp}$*ApA 8 and A$_{Sp}$*ApA 9. Separation into the pure diastereoisomers was achieved by medium pressure chromatography as described above by elution with CHCl$_3$/MeOH (99/1, v/v; 800 ml; 20 ml/fraction; fractions 1–40) followed by elution with CHCl$_3$/MeOH (95/5, v/v; 800 ml; 20 ml/fraction; fractions 41–80). The fully protected A$_{Rp}$*ApA isomer 8 (0.287 g) was eluted in fractions 21–56 (20 ml/fraction). Fractions 57–61 gave the isomer mixture (0.07 g) and the fully protected A$_{Sp}$*ApA isomer 9 (0.132 g) was eluted in fractions 62–64. Chromatographic separation was repeated with each 0.5 g of the crude mixture to yield 1.62 g (51%) of A$_{Rp}$*ApA 8 and 0.94 g (30%) of A$_{Sp}$*ApA 9. Anal. calc. for A$_{Rp}$*ApA-C$_{101}$H$_{127}$N$_{17}$O$_{19}$P$_2$SSi$_4$ (2089.6): C 58.05, H 6.13, H 11.40. Found: C 58.65, H 6.24, N 11.50. UV (MeOH): $\lambda_{max}$ (logε) 279 nm (4.76), 260 nm (4.56), 236 nm (4.73). R$_f$ on silica gel with CHCl$_3$/MeOH (97/3, v/v)=0.35. $^{31}$P-NMR (CDCl$_3$): 69.35 and −1.10 ppm. Anal. calc. for A$_{Sp}$*ApA-C$_{101}$H$_{127}$N$_{17}$O$_{19}$P$_2$SSi$_4$ (2089.6): C 58.05, H 6.13, N 11.25. Found: C 57.03, H 6.33, N 11.14. UV (MeOH): $\lambda_{max}$ (logε) 279 nm (4.77), 260 nm (4.57), 236 nm (4.73). $^{31}$P-NMR (CDCl$_3$): 68.33 and −0.84 ppm.

EXAMPLE 1 a. (PR)-P-Thioadenylyl-2'-5'-adenylyl-2'-5'-
adenosine A$_{Rp}$*ApA 10 b. (PS)-P-Thioadenylyl-2'-5'-adenylyl-2'-5'-
adenosine A$_{Sp}$*ApA 11

The corresponding fully protected trimers 8 and 9, respectively, were separately deblocked by stirring the trimer (0.06 g; 0.029 mmole) with 2% p-TsOH in CH$_2$Cl$_2$/MeOH (4/1, v/v; 1.2 ml) for 1.5 h at r.t. The reaction mixture was diluted with CHCl$_3$ (50 ml), washed with H$_2$O (2×25 ml), dried and evaporated to dryness. The crude product was purified on preparative silica gel plates (20×20×0.2 cm) in CHCl$_3$/MeOH (8/2, v/v). The product bands were eluted with CHCl$_3$/MeOH (4/1, v/v) and evaporated to a foam to give 0.04 g (84%) of the A$_{Rp}$*ApA isomer 10 and 0.034 g (73%) of the A$_{Sp}$*ApA isomer 11. The 5'-hydroxy trimer (0.034 g; 0.08 mmole) was then stirred with 0.5M DBU in pyridine (5.0 ml) and after stirring at r.t. for 20 h, the solution was neutralized with 1M acetic acid in dry pyridine (2.5 ml) and evaporated to dryness. The residue was treated with methanolic ammonia (5 ml) and after 48 h stirring the solvents were removed in vacuo. Desilylation was performed with 1M tetrabutylammonium fluoride in THF (2 ml). After 48 h stirring, the solvent was removed in vacuo and the residue was dissolved in H$_2$O (10 ml) and applied to a DEAE Sephadex A-25 column (60×1 cm). The pure product was eluted with a linear gradient of 0.14–0.17M TEAB buffer, pH 7.5. After evaporation and coevaporation with water several times, the trimer was applied to four paper sheets (35×50 cm) and developed in i-PrOH/conc. ammonia/H$_2$O (6/1/3, v/v/v). The product band was cut out, eluted with H$_2$O, evaporated and lyophilized to give 500 O.D.$_{260\,nm}$ units (79%) of the A$_{Rp}$*ApA isomer 10 and 410 O.D.$_{260\,nm}$ units (65%) of the A$_{Sp}$*ApA isomer 11. UV $\lambda_{max}$ in both cases was 258 nm in H$_2$O. A$_{Rp}$*ApA 10: R$_f$ on cellulose in i-PrOH/ammonia/H$_2$O (6/1/3, v/v/v)=0.33. $^1$H-NMR (D$_2$O): 8.20; 8.19; 8.14 (3s, 3H, H—C(8)); 7.97 (1s, 2H, 2 H—C(2)) and 7.76 (1 s, 1H, 1 H—C(2)); 6.08; 5.93; 5.82 (3d, 3H, 3 H—C(1')). Retention time on reverse-phase HPLC was 5.60 min. A$_{Sp}$*ApA 11: R$_f$ on cellulose in i-PrOH/ammonia/H$_2$O (6/1/3, v/v/v)=0.33. $^1$H-NMR (D$_2$O): 8.14; 8.09; 8.02 (3s, 3H, H—C(8)); 7.94; 7.89: 7.80 (3s, 3H, 2 H—C(2)); 6.03; 5.92; 5.80 (3d, 3H, 3 H—C(1')). Retention time on reverse-phase HPLC was 6.51 min.

Scheme 2 is the reaction scheme for the preparation of the remaining pair of trimer cores, ApA$_{Rp}$*A 23 and ApA$_{Sp}$*A 24, from the protected intermediates 21 and 22, and is outlined in detail in preparations 5 and 6 and Example 2, below.

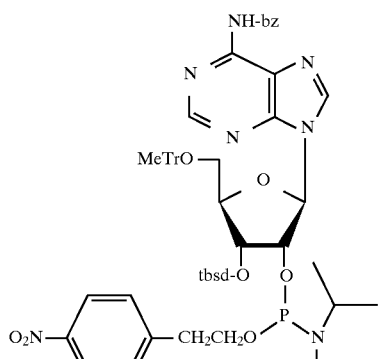
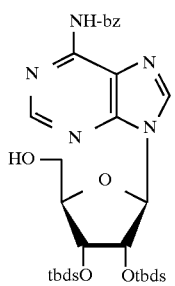
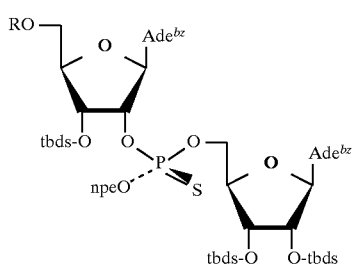
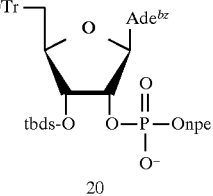
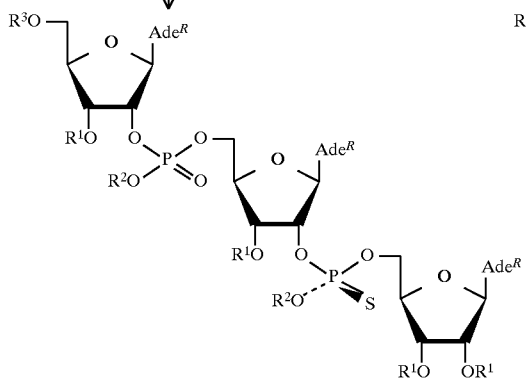
PREPARATION 5
a. N,N-Diisopropyl-trimethylsilylamine
The preparation of the titled compound was in accord with the procedure of Noth and Staudigl, *Chem. Ber.* 115: 3011–3024 (1982). Methyl iodide (37.6 ml; 0.6 mole) in absolute ether (50 ml) was added dropwise (over 90 min) to a suspension of 14.6 g (0.6 mole) of magnesium and a few crystals of iodine in absolute ether (100 ml). The reaction was then stirred for 30 min until all the magnesium was dissolved. Subsequently, N,N-diisopropylamine (78 ml; 0.55 mole) was added within 10–15 min and the reaction was refluxed for 1 h. After cooling to 0° C., trimethylsilyl chloride (76 ml; 0.6 mole) was added dropwise and the reaction mixture was again heated in an oil-bath with vigorous stirring to 80° C. for 20 h. The supernatant liquid was decanted and the residue was extracted with ether (4×50 ml). The supernatant and the ether extract were combined. The solvent, excess trimethylsilyl chloride and unreacted N,N-diisoproylamine were removed by distillation. The product was then isolated by distillation under vacuum at an oil-bath temperature of 60° C. to yield 73 g (80%), $Kp_{18}$= 36°–39° C. $^1$H-NMR (CDCl$_3$): 0.08 (s, 9H, SiCH$_3$); 1.04–1.07 (d, 12H, N—C—CH$_3$), 3.2 (m, 2H, N—CH).

b. Chloro-N,N-diisopropylamino-2-(4-nitrophenyl) ethoxy-phosphane 14 p-Nitrophenylethanol (4.16 g; 25 mmole) was added portion wise to a solution of freshly distilled PCl$_3$ (14 ml; 0.16 mole) in absolute ether (40 ml) at −30° C. under a nitrogen atmosphere within 45 min. The reaction mixture was stirred at r.t. for 1.5 h and the solvent and excess PCl$_3$ were then removed in vacuo at 0° C. The residue was treated with N,N-diisopropyl-trimethylsilylamine (Preparation 5a) (4.33 g; 25 mmole) at 0° C. under a nitrogen atmosphere for 30 min and then at r.t. for 20 h. The resulting trimethylsilyl chloride was removed under high vacuum at r.t. to yield a syrupy pale yellow product (7.1 g; 85%) which crystallized upon storage at −20° C. This material was then used for the subsequent phosphitylation reactions. $^1$H-NMR (CDCl$_3$): 8.1–8.2 (m, 2H, o to NO$_2$); 7.39–7.43 (m, 2H, m to NO$_2$); 4.04–4.18 (m, 2H, P—O—CH$_2$); 3.63–3.79 (m, 2H, N—CH); 3.07–3.13 (t, 2H, P—O—C—CH$_2$); 1.14–1.27 (2d, 12H, N—C—CH$_3$). $^{31}$P-NMR (CDCl$_3$): 181.60 ppm.

c. 6-N-Benzoyl-3'-O-[(tert-butyl)dimethylsilyl]-5'-O-(monomethoxytrityl)-adenosine-2'-O-[(4-nitrophenyl)ethyl)-N,N-diisopropylaimino]-phosphoramidite 15

METHOD A

Compound 1 (3.79 g; 5 mmole) and diisopropylethylamine (3.5 ml) were dissolved in dry CH$_2$Cl$_2$ (20 ml) and then chloro-N,N-diisopropylamino-2-(4-nitrophenyl)-ethoxyphosphane 14 (2.37 g; 10 mmole) was added dropwise under a nitrogen atmosphere. After stirring at r.t. for 2 h, the reaction mixture was diluted with EtOAc (200 ml), the organic phase was washed with a saturated NaHCO$_3$/NaCl solution (3×80 ml), dried over Na$_2$SO$_4$ and evaporated to dryness. The crude product was dissolved in toluene/EtOAc (7/3, v/v) and chromatographed on a silica gel column (12×2 cm) equilibrated with EtOAc/NEt$_3$ (95/5, v/v). The product fractions were eluted with EtOAc/NEt$_3$ (95/5, v/v), collected and evaporated to dryness, yielding 15 (5.28 g; 79%) as a colorless solid foam. Anal. calc. for C$_{57}$H$_{68}$N$_7$O$_9$PSi (1054.3): C 64.94, H 6.50, N 9.30. Found: C 64.81, H 6.51, N 9.01. UV (MeOH): $\lambda_{max}$ (log$\epsilon$) 277 nm (4.50), 229 nm (4.48). $^{31}$P-NMR (CDCl$_3$): 150.27, 150.01 ppm. R$_f$ on silica gel in toluene/EtOAC (1/1, v/v): 0.62 and 0.68 (diastereomers).

METHOD B

Alternatively, compound 15 was synthesized using bis-(diisopropylamino)-[2-(4-nitrophenyl)ethoxy]-phosphane 27, infra. To a solution of 1.52 g (2 mmole) of compound 1 in absolute CH$_3$CN (10 ml), bis-(diisopropylamino)-[2-(4-nitrophenyl)ethoxy]-phosphane 27 (1.59 g, 4 mmole) and tetrazole (0.07 g; 1 mmole) were added under nitrogen atmosphere and the reaction mixture was stirred for 17 h at r.t. The reaction mixture was diluted with EtOAc (120 ml) and washed twice with saturated NaHCO$_3$/NaCl solution (60 ml), dried over Na$_2$SO$_4$ and evaporated to dryness. The crude solid foam was applied onto a flash silica gel column (20×2.5 cm) and chromatographed with toluene/EtOAc (1/1, v/v; 250 ml). The product fraction (90 ml) was evaporated to give 15 (1.9 g, 90%) as a colorless solid foam.

c. Bis-(diisopropylamino)-[2-(4-nitrophenyl) ethoxy]-phosphane 27

2-(4-Nitrophenyl)ethanol (8.35 g, 50 mmole) was added in small portions over 30 min to a solution of distilled PCl$_3$ (28 ml; 280 mmole) in absolute ether (80 ml) at −5° C. under a nitrogen atmosphere. After stirring for 15 min at −5° C. and 1.5 h at r.t., the solvent and excess PCl$_3$ were removed under high vacuum. Then, the yellowish syrupy residue was dissolved in 200 ml of absolute ether and reacted at −10° C. with N,N-diisopropylamine (64 ml, 450 mmole) by dropwise addition over 30 min under a nitrogen atmosphere. The reaction mixture was stirred at −10° C. for 15 min and r.t. for 16 h. The voluminous precipitate of N,N-diisopropyl-amine hydrochloride was filtered under nitrogen and the solvent was removed in vacuo. The yellowish syrupy product (17.6 g; 89%), which crystallized on storage at −20° C. was pure enough to be used for phosphitylation reactions. $^1$-NMR (CDCl$_3$): 8.10–8.13 (d, 2H, o to NO$_2$); 7.36–7.40 (d, 2H, m to NO$_2$); 3.75–3.82 (q, 2H, P—O—CH$_2$); 3.36–3.51 (m, 2H, N—CH); 2.95–3.00 (t, 2H, P—O—C—CH$_2$); 1.05–1.12 (2d, 12H, N—C—CH$_3$). $^3$P-NMR (CDCl$_3$): 123.53 ppm.

PREPARATION 6 a. 6-N-Benzoyl-3'-O-[(tert-butyl)dimethylsilyl]-5'-O-(monomethoxytrityl)-adenylyl-2'-[(O$^P$-2-(4-nitrophenyl)ethyl-5']-6-N-benzoyl-3'-O-[(tert-butyl) dimethylsilyl]-(PR)-P-thioadenylyl-2'-[(O$^P$-2-(4-nitro-phenyl)ethyl-5']-6-N-benzoyl-2',3'-di-O-[(tert-butyl)dimethylsilyl]-adenosine ApA$_{Rp}$*A 21 b. 6-N-Benzoyl-3'-O-[(tert-butyl)dimethylsilyl]-5'-O-(monomethoxytrityl)-adenylyl-2'-[(O$^P$-2-(4-nitrophenyl)ethyl-5']-6-N-benzoyl-3'-O-[(tert-butyl) dimethylsilyl]-(PS)-P-thioadenylyl-2'-[(O$^P$-2-(4-nitro-phenyl)ethyl-5']-6-N-benzoyl-2',3'-di-O-[(tert-butyl)dimethylsilyl]-adenosine ApA$_{Sp}$*A 22

Triethylammonium 6-N-benzoyl-3'-O-[(tert-butyl) dimethylsilyl]-5'-O-(monomethoxytrityl)adenosine-2'-[2-(4-nitrophenyl)ethyl]-phosphate 20 (0.10 g; 0.1 mmole), Charubala et al., Liebig's Ann. Chem., 2392–2406 (1981), and the respective 5'-hydroxy dimers PR 18 and PS 19, (0.066 g; 0.05 mmole), Charubala and Pfleiderer (1992) supra, were coevaporated with dry pyridine (3×5 ml), dissolved in one ml dry pyridine and (2,4,6-triisopropyl) benzenesulfonyl chloride (0.062 g; 0.2 mmole) and 3-nitro-1,2,4-triazole (0.068 g; 0.6 mmole), Kroger and Mietchen, Z. Chem. 9: 378–379 (1969); Jones et al., Tetrahedron 36: 3075–3085 (1980), were added. After stirring at r.t. for 20 h, the reaction mixture was diluted with CHCl$_3$ (100 ml), washed with H$_2$O (2×50 ml), dried and evaporated. Final evaporations were done with toluene (2×10 ml) to remove pyridine. The crude trimers 21 and 22, respectively, were purified by silica gel column chromatography (15×2 cm), using first CHCl$_3$ and then CHCl$_3$/MeOH (100/1, v/v) as eluants. The product fraction was collected and evaporated to a solid foam, which was dried under high vacuum to give 0.08 g (70%) of 21. Anal. calc. for C$_{111}$H$_{135}$N$_{17}$O$_{23}$P$_2$SSi$_4$×2 H$_2$O (2317.8): C 57.52, H 5.95, N 10.27. Found: C 57.15, H 6.13, N 10.72. UV (MeOH): $\lambda_{max}$ (log$\epsilon$) 276 nm (4.87), 227 nm (4.83). R$_f$ on silica gel in CH$_2$Cl$_2$/EtOAc (1/1)=0.63. $^{31}$P-NMR (CDCl$_3$): 69.88 and −1.0 ppm.

EXAMPLE 2 a. Adenylyl-(2'-5')-(PR)-P-thioadenylyl-(2'-5')-adenosine ApA$_{Rp}$*A 23 b. Adenylyl-(2'-5')-(PS)-P-thioadenylyl-(2'-5')-adenosine and ApA$_{Sp}$*A 24

The fully protected trimers, ApA$_{Rp}$*A 21 and ApA$_{Sp}$*A 22, were separately deblocked by stirring the corresponding trimer (0.088 g; 0.037 mmole) with 2% p-TsOH in $CH_2Cl_2$/MeOH (4/1, v/v; 0.8 ml. After 30 min stirring at r.t., the reaction mixture was diluted with $CHCl_3$ (50 ml) and washed with $H_2O$ (2×25 ml). The organic phase was dried over $NaSO_4$ and evaporated to dryness. The crude product was purified or a silica gel column (5×2 cm) and the product eluted with $CHCl_3$/MeOH (100/1, v/v), evaporated and dried under high vacuum to give 0.073 g (94%) of the 5'-hydroxy trimer $ApA_{Rp}$*A 21 and 0.061 g (84%) of the 5'-hydroxy trimer $ApA_{Sp}$*A 22. The resulting 5'-hydroxy trimer (0.04 g; 0.02 mmole) was then stirred with 10 ml of 0.5M DBU in pyridine. After 24 h, the solution was neutralized with 1M acetic acid in pyridine (10 ml) and evaporated to dryness. The residue was treated with saturated methanolic ammonia (6 ml) and after stirring at r.t. for 48 h, the solvent was removed in vacuo and the residue was desilylated with 1M $Bu_4NF$ in THF (5 ml) for 48 h. The solvent was then removed in vacuo and the residue was dissolved in water (10 ml) and applied onto a DEAE Sephadex A-25 column (60×1 cm). The product was eluted with a linear gradient of 0.14–0.17M TEAB buffer, pH 7.5. After evaporation and coevaporation with water several times, the trimer was applied to four paper sheets (35×50 cm) and developed in i-PrOH/conc. ammonia/$H_2O$ (6/1/3, v/v/v). The product band was cut out, eluted with $H_2O$, evaporated and lyophilized to give 354 O.D.$_{260\ nm}$ units (79%) of the $ApA_{Rp}$*A isomer 23 and 410 O.D.$_{260\ nm}$ units (58%) of the $ApA_{Sp}$*A isomer 24. UV $\lambda_{max}$ in both cases was 258 nm in $H_2O$. $ApA_{Rp}$*A 23: $R_f$ on cellulose in iPrOH/ammonia/$H_2O$ (6/1/3, v/v/v) 0.34. $^1$H-NMR ($D_2O$): 8.17; 8.16; 8.09 (3s, 3H, H—C(8)); 7.90, 7.78 (2 s, 3H, 3×H—C(2)); 6.04; 5.96; 5.80 (3d, 3H, 3 H—C(1')). Retention time on reverse-phase HPLC was 5.98 min. $ApA_{Sp}$*A (24): $R_f$ on cellulose in i-PrOH/ammonia/$H_2O$ (6/1/3, v/v/v)=0.33. $^1$H-NMR ($D_2O$): 8.17; 8.07; 8.04 (3s, 3H, 3×H—C(8)); 8.01; 7.92: 7.72 (3s, 3H, 2 3×H—C(2)); 6.04; 5.92; 5.82 (3d, 3H, 3×H—C(1 )). Retention time on reverse-phase HPLC was 7.23 min.

Preparations 7 and 8 begin the preparation for the fully resolved tetramers, $ApA_{Rp}$*ApA 38 and $ApA_{Sp}$*ApA 39, from their corresponding dimer 28 (Scheme 1). The reaction scheme continues with the addition of the trimer moiety in Preparations 9 and 10 (Scheme 2).

PREPARATION 7

6-N-Benzoyl-3'-O-[(tert-butyl)dimethylsilyl]-5'-(monomethoxytrityl)-adenylyl-2'-[($O^P$-2-(4-nitrophenyl)ethyl-5']-6-N-benzoyl-2',3'-di-O-[(tert-butyl)dimethylsilyl]-adenosine $A_{(Rp,Sp)}$*A 28

The phosphoramidite 15 (1.41 g; 1.34 mmole), 6-N-benzoyl-2',3'-di-O-[(tert-butyl)dimethylsilyl]-adenosine 5 (0.36 g, 0.93 mmole) and tetrazole (0.188 g, 2.68 mmole) were stirred at r.t. in absolute $CH_3CN$ (9 ml) under a nitrogen atmosphere. After 4 h, a solution of $I_2$ [0.5 g in $CH_2Cl_2/H_2O$/pyridine (1/1/3, v/v/v)] was added dropwise until the brown color did not disappear. The mixture was stirred was stirred for another 15 min, then extracted with $CH_2Cl_2$ (3×60 ml) and saturated $Na_2S_2O_3$/NaCl solution (2×60 ml). The $CH_2Cl_2$ phase was collected, dried over $Na_2SO_4$, evaporated and coevaporated with toluene (2×20 ml) to remove the pyridine. The crude dimer (1.85 g) was dissolved in $CH_2Cl_2$ and applied onto a flash silica gel column (12×2.5 cm) and chromatographed using $CH_2Cl_2$/1% MeOH (400 ml), 2% MeOH (200 ml) and 3% MeOH (200 ml) to elute the product (600 ml). This fraction was evaporated to dryness to give 1.45 g (quant. yield) of the dimer 28 as a colorless amorphous solid. The identity of the isolated dimer 28 was proven by comparison with authentic material by spectrophotometric comparison. The authentic material was synthesized by the phosphotriester method: Anal. calc. for ApA 28=$C_{80}H_{98}N_{11}O_{15}PSi_3$ (1569.0): C 61.24, H 6.30, N 9.82. Found: C 61.24, H 6.24, N 9.65. UV (MeOH): $\lambda_{max}$ (logε) 277 (4.69); [260 (4.54)]; [231 (4.66)]. $R_f$ on silica gel with $CHCl_3$/MeOH (49/1, v/v)=0.37.

PREPARATION 8

6-N-Benzoyl-3'-O-[(tert-butyl)dimethylsilyl]-adenylyl-2'-[($O^P$-2-(4-nitrophenyl)ethyl-5']-6-N-benzoyl-2',3'-di-O-[(tert-butyl)dimethylsilyl]-adenosine-5'-OH-$A_{(Rp,Sp)}$*A 29

The crude dimer mixture 28 (2.24 g, 1.43 mmole) was stirred with 2% p-TsOH in $CH_2Cl_2$/MeOH (4/1, v/v, 20 ml) at r.t. for 30 min. The reaction mixture was diluted with $CH_2Cl_2$ (200 ml), washed with $H_2O$ (2×80 ml), dried over $Na_2SO_4$ and evaporated to dryness. The colorless amorphous residue (2.0 g) was applied onto a flash silica gel column (21×2.5 cm) and chromatographed with $CH_2Cl_2$ (200 ml), $CH_2Cl_2$/2% MeOH (400 ml) and the product was eluted with $CH_2Cl_2$/2% MeOH (500 ml). The product fraction was evaporated and dried under high vacuum to give 1.2 g (75% calculated to compound 5 over 2 steps) of 5'-OH dimer 29 as an amorphous solid. The identity of the isolated dimer 29 with authentic material was proven by chromatographic and spectrophotometric comparison. Anal. calc. for 5'-OH-ApA 29=$C_{60}H_{82}N_{11}O_{14}PSi_3$ (1296.6): C 55.58, H 6.37, N 11.88. Found: C 55.33, H 6.38, N 11.78. UV (MeOH): $\lambda_{max}$ (logε) 278 (4.68); [259 (4.51)]; 233 (4.46). $R_f$ on silica gel with toluene/EtOAc/MeOH (5:4:1)=0.53. $^{31}$P=NMR ($CDCl_3$: −0.36 and −0.73 ppm.

PREPARATION 9 a. 6-N-Benzoyl-3'-O-[(tert-butyl)dimethylsilyl]-5'-O-(monomethoxytrityl)-(PR)-P-thioadenylyl-2'-[($O^P$-2-(4-nitrophenyl)ethyl-5']-6-N-benzoyl-3'-O-[(tert-butyl)dimethylsilyl]-adenylyl-2'-[($O^P$-2-(4-nitrophenyl)ethyl-5'-]-6-N-benzoyl-2',3'-di-O-[(tert-butyl)dimethylsilyl]-adenosine $A_{Rp}$*ApA 30 b. 6-N-Benzoyl-3'-O-[(tert-butyl)dimethylsilyl]-5'-O-(monomethoxytrityl)-(PS)-P-thioadenylyl-2'-[($O^P$-2-(4-nitrophenyl)ethyl-5']-6-N-benzoyl-3'-O-[(tert-butyl)dimethylsilyl]-adenylyl-2'-[($O^P$-2-(4-nitrophenyl)ethyl-5'-]-6-N-benzoyl-2',3'-di-O-[(tert-butyl)dimethylsilyl]-adenosine $A_{Sp}$*ApA 31

The phosphoramidite 15 (0.59 g, 0.56 mmole), the 5'-hydroxy ApA dimer 29 (0.52 g, 0.40 mmole) and tetrazole (0.079 g; 1.12 mmole) were dissolved in dry $CH_3CN$ (4 ml) and stirred at r.t. under a nitrogen atmosphere. After 3 h, phosphoramidite 15 (0.464, 0.44 mmole) and tetrazole (0.062 g, 0.88 mmole) were added again and the mixture was stirred for another 3 h. Then, oxidation with $S_8$ (0.257 g, 1 mmole) and pyridine (2.6 ml) was followed within 16 h at r.t. The reaction mixture was diluted with $CH_2Cl_2$ (200 ml) at r.t. The reaction mixture was diluted with $CH_2Cl_2$ (200 ml), washed with a saturated NaCl solution (2×80 ml), dried over $Na_2SO_4$ and evaporated to dryness. Final coevaporation was done with toluene (3×20 ml) to remove pyridine. The crude diastereoisomeric mixture $A_{(Rp,Sp)}$*ApA 30+31 was dissolved in $CH_2Cl_2$ (20 ml), applied onto a flash silica gel column (11×2.5 cm) and chromatographed with $CH_2Cl_2$ (400 ml), $CH_2Cl_2$/0.5% MeOH (200 ml), 1% MeOH (200 ml) and the product was eluted with $CH_2Cl_2$/1.5% MeOH (200 ml). The product fraction was evaporated to dryness to give 0.713 g (78%) of the isomeric mixture 30+31. Separation into the pure diastereomers was achieved by application to preparative silica gel plates (40×20×0.2 cm, 8 plates) in toluene/EtOAc (1/1, v/v, 4 developments). The isomeric products bands were separately eluted with CH$_2$Cl$_2$/MeOH (4/1, v/v) and evaporated to solid foams, which were dried under high vacuum to give 0.311 g (34%) of the fully protected A$_{Rp}$*ApA isomer 30 and 0.245 g (270%) of the fully protected A$_{Sp}$*ApA isomer 31. Anal. calc. for A$_{Rp}$*ApA 30=Cl$_{111}$H$_{13.5}$N$_{17}$O$_{23}$P$_2$SSi$_4$×H$_2$O (2299.8): C 57.97, H 6.00, N 10.35. Found: C 57.63, H 6.11, N 10.39. UV (MeOH): $\lambda_{max}$ (logε) 278 (4.87); [260 (4.72)]; [231. (4.75)]. R$_f$ on silica gel with toluene/EtOAc (1/1, v/v, 2 developments) and toluene/EtOAc (1/2, v/v, 1 development)=0.37. Anal. calc. for A$_{Sp}$*ApA 31=C$_{111}$H$_{135}$N$_{17}$O$_{23}$P$_2$SSi$_4$×2 H$_2$O (2317.8): C 57.52, H 6.05, N 10.27. Found: C 57.44, H 6.19, N 10.41. UV (MeOH): $\lambda_{max}$ (logε) 277 (4.86); [260 (4.72)]; [231 (4.75)]. R$_f$ on silica gel with toluene/EtOAc (1:1, 2 developments) and toluene/EtOAc (1:2, 1 development)=0.27.

PREPARATION 10 a. 6-N-Benzoyl-3'-O-[(tert-butyl)dimethylsilyl]-(PR)-P-thioadenylyl-2'-[O$^P$-2-(4-nitrophenyl)ethyl-5']-6-N-benzoyl-3'-O-[(tert-butyl)dimethylsilyl]-adenylyl-2'-[O$^P$-2-(4-nitrophenyl)ethyl-5']-6-N-benzoyl-2',3'-di-O-[(tert-butyl)dimethylsilyl]-adenosine 5'-hydroxy A$_{Rp}$*ApA 32 b. 6-N-Benzoyl-3'-O-[(tert-butyl)dimethylsilyl]-(PS)-P-thioadenylyl-2'-[O$^P$-2-(4-nitrophenyl)ethyl-5']-6-N-benzoyl-3'-O-[(tert-butyl)dimethylsilyl]-adenylyl-2'-[O$^P$-2-(4-nitrophenyl)ethyl-5']-6-N-benzoyl-2',3'-di-O-[(tert-butyl)dimethylsilyl]-adenosine 5'-hydroxy A$_{Sp}$*ApA 33

The corresponding fully protected trimers 30 and 31, respectively, were separately detritylated by stirring the trimer (A$_{Rp}$*ApA 30: 0.263 g, 0.115 mmole; A$_{Sp}$*ApA 31: 0.21 g, 0.92 mmole) with 2% p-TsOH in CH$_2$Cl$_2$/MeOH (4/1, v/v, for 30: 3.2 ml; for 31: 2.6 ml) for 75 min at r.t. The reaction mixture was diluted with Ch$_2$Cl$_2$ (120 ml), washed with H$_2$O (2×40 ml), dried over Na$_2$SO$_4$ and evaporated to dryness. The crude product was purified on preparative silica gel plates (40×20×0.2 cm) in toluene/EtOAc (3/7, v/v), the product bands were eluted with CH$_{2C1}$2/MeOH (4/1, v/v) and evaporated to a solid foam to give 0.2 g (86%) of the 5'-hydroxy A$_{Rp}$*ApA 32 and 0.121 g (66%) of the 5'-hydroxy A$_{Sp}$*ApA 33, respectively. Anal. Calc. for 5'-OH-A$_{Rp}$*ApA 32=C$_{91}$H$_{119}$N$_{17}$O$_{22}$SSI$_4$ (2009.4: C 54.39, H 5.97, N 11.85. Found: C 54.12, H 6.13, N 1174. UV (MeOH): $\lambda_{max}$ (logε) 278 (4.86); [260 (4.71)]; [233 (4.64]. R$_f$ on silica gel with toluene/EtOAc (3:7, 2 developments) =0.35 (diastereomers). $^{31}$P-NMR: 69.60, 68.91, −0.36 and −0.56 ppm (diastereomers). Anal. calc. for 5'-OH-A$_{Sp}$*ApA 33=C$_{91}$H$_{119}$N$_{17}$O$_{22}$P$_2$SSi$_4$ (2009.4): C 54.39, H 5.97, N 11.85. Found: C 54.29, H 6.23, N 11.51. UV (MeOH); $\lambda_{max}$ (logε) 277 (4.85; [260 (4.71)]; [233 (4.63)]. R$_f$silica gel with toluene/EtOAc (3:7, 2 developments=0.42 (diastereomers). $^{31}$P-NMR: 69.28, 69.09, −0.33 and −0.56 ppm (diastereomers).

Scheme 3 is the reaction scheme for the preparation of the fully resolved tetramers, ApA$_{Rp}$*ApA 38 and ApA$_{Sp}$*ApA 39, from the protected intermediates, 34 and 35. The preparation of these compounds is outlined in Preparations 11 and 12 and Example 3.

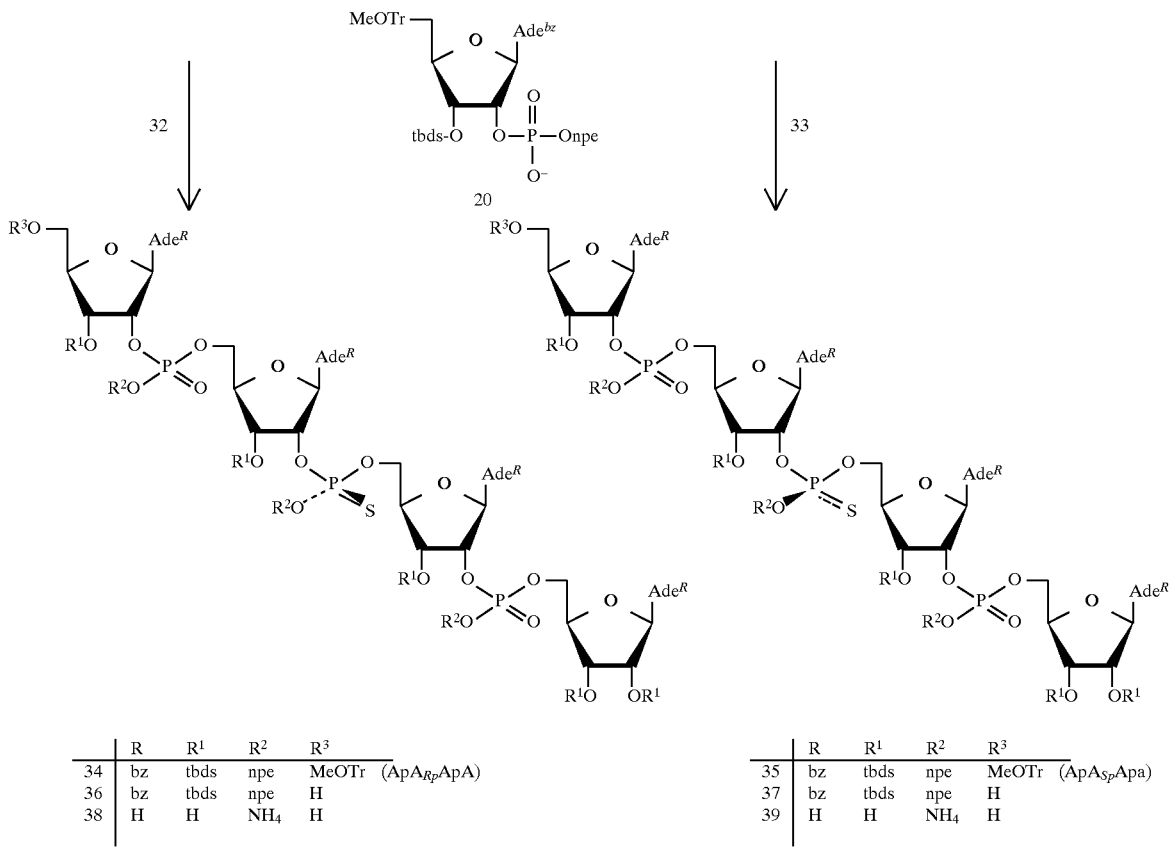

PREPARATION 11 a. 6-N-Benzoyl-3'-O-[(tert-butyl)dimethylsilyl]-5'-O-(monomethoxytrityl)-adenylyl-2'-[$O^P$-2-(4-nitrophenyl)ethyl]-5']-6-N-benzoyl-3'-O-[(tert-butyl)dimethylsilyl]-(PR)-P-thioadenylyl-2'-[$O^P$-(2-(4-nitrophenyl)ethyl)-5']-6-N-benzoyl-3'-O-[(tert-butyl)dimethylsilyl]-adenylyl-2'-[$O^P$-2-(4-nitrophenyl)-ethyl-5']-6-N-benzoyl-2',3'-di-O-[(tert-butyl)dimethylsilyl-adenosine $ApA_{Rp}$*ApA 34 b. 6-N-Benzoyl-3'-O-[(tert-butyl)dimethylsilyl]-5'-O-(monomethoxytrityl)-adenylyl-2'-[$O^P$-2-(4-nitrophenyl)ethyl-5']-6-N-benzoyl-3'-O-[(tert-butyl)dimethylsilyl]-(PS)-P-thioadenylyl-2'-[$O^P$-(2-(4-nitrophenyl)ethyl)-5']-6-N-benzoyl-3'-O-[(tert-butyl)dimethylsilyl]-adenylyl-2'-[$O^P$-2-(4-nitrophenyl)-ethyl-5']-6-N-benzoyl-2',3'-di-O-(tert-butyl)dimethylsilyl-adenosine $ApA_{Sp}$*ApA 35

The condensation to the fully protected tetramers 34 and 35, respectively, were separately realized by coevaporating triethylammonium-6-N-benzoyl-3'-O-[(tert-butyl)dimethylsilyl]-5'-O-(monomethoxytrityl)adenosine-2'-[2-(4-nitrophenyl)ethyl]-phosphate 20 (0.108 g, 0.1 mmole) and the 5'-hydroxy PR trimer 32 or PS trimer 33 (0.1 g, 0.05 mmole), respectively, with dry pyridine (3×2 ml), dissolved in dry pyridine (0.5 ml) and then (2,4,6-triisopropyl)benzenesulfonyl chloride (0.061 g, 0.2 mmole) and 3-nitro-1,2,4-triazole (0.068 g, 0.6 mmole) were added. The solution was stirred at r.t. for 21 h, then extracted with $CH_2Cl_2$ (2×20 ml) and $H_2O$ (3×20 ml). The organic phase was collected, dried over $Na_2SO_4$, evaporated and coevaporated with toluene (3×20 ml) to remove pyridine. The crude tetramers 34 and 35, respectively, were separately purified on preparative silica gel plates (40×20×0.2 cm) with toluene/EtOAc/MeOH (5/4/0.5, v/v/v), the product bands were eluted with $CH_2Cl_2$/MeOH (4/1, v/v/) and evaporated to solid foams, which were dried under high vacuum to give 0.116 g (78%) of $ApA_{Rp}$*ApA 34 and 0.12 g (8%) of the $ApA_{Sp}$*ApA 35. Anal. calc. for $ApA_{Rp}$*ApA 34=$C_{142}H_{172}N_{23}O_{32}P_3SSi_5 \times 2 H_2O$ (3014.5): C 56.58, H 5.89, N 10.69; found: C 56.22, H 6.07, N 10.57. UV (MeOH): $\lambda_{max}$ (logε) 277 (4.99): [260 (4.85)]; [231 (4.85)]. $R_f$ silica gel with toluene/EtOAc/MeOH (5:4:0.5)=0.63 (diastereomers). Anal. calc. for $ApA_{Sp}$*ApA 35=$C_{142}H_{172}N_{23}O_{32}P_3SSi_5 \times H_2O$ (2996.5): C 56.92, H 5.85, N 10.75; found: C 56.40, H 5.89, N 10.61. UV (MeOH): $\lambda_{max}$ (logε) 277 (5.01): [260 (4.88)]; [232 (4.89)]. $R_f$ silica gel with toluene/EtOAc/MeOH (5/4/0.5, v/v/v)=0.62 (diastereomers).

PREPARATION 12 a. 6-N-Benzoyl-3'-O-[(tert-butyl)dimethylsilyl]-adenylyl-2'-[($O^P$-2-(4-nitrophenyl)ethyl-5']-6-N-benzoyl-3'-O-[(tert-butyl)dimethylsilyl]-(PR)-P-thioadenylyl-2'-[($O^P$-2-(4-nitrophenyl)ethyl-5']-6-N-benzoyl-3'-O-[(tert-butyl)dimethylsilyl]-adenylyl-2'-[($O^P$-2-(4-nitrophenyl)-ethyl-5']-6-N-benzoyl-2',3'-di-O-[(tert-butyl)dimethylsilyl]-adenosine 5'-OH-$ApA_{Rp}$*ApA 36 b. 6-N-Benzoyl-3'-O-[(tert-butyl)dimethylsilyl]-adenylyl-2'-[($O^P$-2-(4-nitrophenyl)ethyl-5']-6-N-benzoyl-3'-O-[(tert-butyl)dimethylsilyl]-(PS)-P-thioadenylyl-2'-[($O^P$-2-(4-nitrophenyl)ethyl-5']-6-N-benzoyl-3'-O-[(tert-butyl)dimethylsilyl]-adenylyl-2'-[($O^P$-2-(4-nitrophenyl)-ethyl-5']-6-N-benzoyl-2',3'-di-O-[(tert-butyl)dimethylsilyl]-adenosine 5'-OH-$ApA_{Sp}$*ApA 37

The fully protected tetramers (0.105 g; 0.035 mmole) 34 and 35, respectively, were separately detritylated by treatment with 20% p-TsOH in $CH_2Cl_2$/MeOH (4/1, v/v, 1.2 ml) for 1 h at r.t. The reaction mixture was extracted with $CH_2Cl_2$ (3×40 ml) and washed with $H_2O$ (3×30 ml). The organic phase was collected, dried over $Na_2SO_4$ and evaporated to dryness. The resulting residue was purified on preparative silica gel plates (20×20×0.2 cm) in toluene/EtOAc/MeOH (5/4/0.5, v/v/v). The product bands were eluted with $CH_2Cl_2$/MeOH (4:1) and evaporated to a solid foam, which was dried in high vacuum to give 0.064 g (67%) of the 5'-hydroxy $ApA_{Rp}$*ApA 36 and 0.057 g (60%) of the corresponding PS tetramer 37. Anal. calc. for 5'-OH-$ApA_{Rp}$*ApA 36=$C_{122}H_{156}N_{23}O_{31}P_3SSi_5 \times H_2O$ (2724.1): C 53.79, H 5.85, N 11.83; found: C 53.62, H 5.87, N 11.51. UV (MeOH): $\lambda_{max}$ (logε) 277 (5.00); [260 (4.87)]; 92.35 (4.81)]. $R_f$ silica gel with toluene/EtOAc/MeOH (5:4:0.5)=0.41. Anal. calc. for 5'-OH-$ApA_{Sp}$*ApA 37=$C_{122}H_{156}N_{23}O_{31}P_3SSi_5 \times HO$ (2724.1): C 53.69, H 5.85, N 11.83; found: C 53.58, H 5,97, N 11.32. UV (MeOH): $\lambda_{max}$ (logε) 277 (4.96): [260 (4.82)]; 234 (4.74)]. $R_f$ silica gel with toluene/EtOAc/MeOH (5/4/0.5, v/v/v)=0.39.

EXAMPLE 3 a. Adenylyl (2'-5')-(PR)-P-thioadenylyl-(2'-5')-adenylyl-2(2'-5')-adenosine $ApA_{Rp}$*ApA 38 b. Adenylyl (2'-5')-(PS)-P-thioadenylyl-(2'-5')-adenylyl-2(2'-5')-adenosine $ApA_{Sp}$*ApA 39

The corresponding 5'-hydroxy tetramers 36 and 37, respectively, were separately deblocked by stirring each 5'-hydroxy tetramer (0.056 g; 0.021 mmole) with 0.5M DBU in absolute $CH_3CN$ (2.5 ml) at r.t. and after 22 h, the solution was neutralized with 1M AcOH in absolute $CH_3CN$ (1.25 ml) and evaporated to dryness. The residual mixture was then treated with methanolic ammonia and after stirring at r.t. for 60 h, the solvent was removed in vacuum and finally the residue was disilylated with 1M $Bu_4NF$ in THF (5 ml) for three days. The solvent was then removed, the residue was dissolved in HO (10 ml), applied onto a DEAE Sephadex column A-25 (30×2 cm) and chromatographed first with $H_2O$ (200 ml) and then with a linear gradient of 0–0.04 ml TEAB buffer, pH 7.5, within 3000 ml (flow rate 2 ml/min). Under this condition, the $ApA_{Rp}$*ApA tetramer 38 was eluted with a 0.23–0.28M TEAB buffer and $ApA_{Sp}$*ApA tetramer 39 with 0.245–0.305M TEAB buffer, respectively. The product fractions were collected, evaporated and coevaporated several times with MeOH. For further purification, paper chromatography was performed using a system of i-PrOH/ammonia $H_2O$ (55/10/35, v/v/v). The product band was cut out, eluted with $H_2O$, concentrated to a smaller volume and finally lyophilized to give 728 O.D.$_{260\ nm}$ units (73%) of the $ApA_{Rp}$*ApA isomer 38 and 686 O.D.$_{260\ nm}$ units (69%) of the $ApA_{Sp}$*ApA isomer 39, respectively. $ApA_{Rp}$*ApA 38: $R_f$ on cellulose in i-PrOH/ammonia/$H_2O$ (55:10:35)=0.36. UW ($H_2O$): $\lambda_{max}$ 257 nm. $^1$H-NMR (D$_2$O): 8.15, 8.07, 8.06, 7.93 (4s, 4H, 4×H—C(8)); 7.92 (s, 2H, 2×H—C(2)); 6.03, 5.89, 5.86, 5.79 (4d, 4×H—C(1')). HPLC: on PR-18, A: 50 mM $NH_4H_2PO_4$ (pH 7.24). B: MeOH/$H_2O$ (1/1, v/v); gradient: 0–1 min, 80% A, 20% B; 1–31 min, 30% A, 70% B; retention time: 9.55 min. $ApA_{Sp}$*ApA 39: $R_f$ on cellulose in i-PrOH/ammonia/$H_2O$ (55/10/35, v/v/v)=0.40. UV ($H_2O$): $\lambda_{max}$ 257 nm. HPLC: PR-18, A: 50 mM $NH_4H_2PO_4$ (pH 7.24). B: MeOH/$H_2O$ (1/1, v/v); gradient: 0–1 min, 80% A, 20% B; 1–31 min, 30% A, 70% B; retention time: 10.37 min.

Scheme 4 is the beginning of the reaction scheme for the preparation of the remaining tetramers from their intermediates, $A_{Rp}$*Ap-diester 45 and the $A_{Sp}$*Ap-diester 46, with the blocking groups in place. The preparation of the diesters is outlined in Preparations 13 and 14.

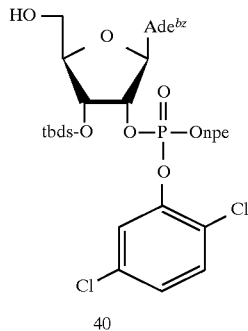

40

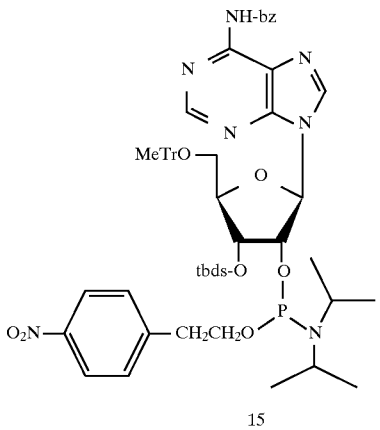

15

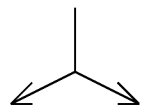

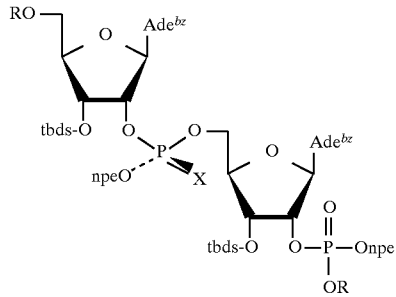

| | X | R |
|---|---|---|
| 41 | O | 2,5-di Cl $C_6H_4$ |
| 42 | O | $Et_3NH$ |
| 43 | S | 2,5-di Cl $C_6H_4$ |
| 45 | S | $Et_3NH$ |

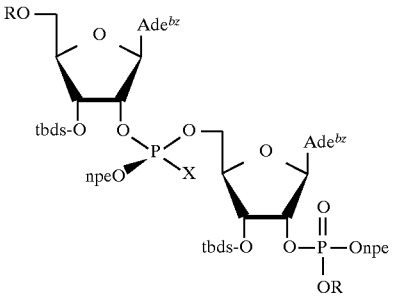

| | X | R |
|---|---|---|
| 41a | O | 2,5-di Cl $C_6H_4$ |
| 42a | O | $Et_3NH$ |
| 44 | S | 2,5-di Cl $C_6H_4$ |
| 46 | S | $Et_3NH$ |

PREPARATION 13 a. 6-N-Benzoyl-3'-O-[(tert-butyl)dimethylsilyl]-5')-(monomethoxytrityl)-adenylyl -2'-[($O^P$-2-(4-nitrophenyl)ethyl-5']-6-N-benzoyl-3'-O-[(tert-butyl)dimethylsilyl]-adenosine-2'-[2,5-dichlorophenyl,2-(4-nitrophenyl)-ethylphosphate]ApAp-triester 41 and 41a 6-N-Benzoyl-3'-O-[(tert-butyl)dimethylsilyl]-adenosine-2'-[2,5-dichlorophenyl,2-(4-nitrophenyl)ethylphosphate]5'-OH-Ap-triester 40 (0.43 g, 0.5 mmole) and the phosphoramidite 15 (0.735 g, 0.7 mmole) were dissolved in absolute $CH_3CN$ (5 ml) in the presence of tetrazole (0.098 g, 1.5 mmole) under a nitrogen atmosphere. After stirring for 3.5 h at r.t., phosphoramidite (0.2 g, 0.19 mmole) and tetrazole (0.026 g, 0.37 mmole) were added again and the reaction mixture was stirred for another 30 min. A solution of $I_2$ [0.5 g in $Ch_2Cl_2/H_2O$/pyridine (1/1/3, v/v/v)] was added dropwise until the brown color did not disappear. The mixture was stirred for another 10 min, diluted with $CH_2Cl_2$ (20 ml) and washed with saturated $Na_2S_2O_3NaCl$ solution (2×80 ml). The organic phase was collected, dried over $Na_2SO_4$, evaporated and coevaporated with toluene (3×30 ml) to remove the pyridine. The crude product was purified by flash silica gel chromatography (15×2 cm), using toluene/EtOAc (1/1, v/v), EtOAc and EtOAc/2–4% MeOH as eluants. The product fraction was evaporated to a solid foam, which was dried in high vacuum at 30° C. to give 0.610 g (67%) of the ApAp-triester 41 and 41a. The identity of the isolated compound with authentic material was proved by spectrophotometric comparison. The authentic material was synthesized from the Ap-diester 20 (Charubala et al., 1981) with the 5'-hydroxy P-triester 40 by the phosphotriester method. Anal. calc. for ApAp-triester=$C_{88}H_{94}N_{12}O_{20}Cl_2P_2SSi_2$ (1828.8): C 57.80, H 5.18, N 9.9. Found: C 57.77, H 5.20, N 9.02. UV (MeOH): $\lambda_{max}$ (log$\epsilon$): 277 (4.75); [260 (4.62)]; [228 (4.72)]. $R_f$ on silica gel with toluene/EtOAc/MeOH (5/4/1, v/v/v)=0.78.

b. 6-N-Benzoyl-3'-O-[(tert-butyl)dimethylsilyl]-5')-(monomethoxytrityl)-(PR,PS)-P-thioadenylyl-2'-[($O^P$-2-(4-nitrophenyl)ethyl-5']-6-N-benzoyl-3'-O-[(tert-butyl)dimethylsilyl]-adenosine-2'-[2,5-dichlorophenyl-2-(4-nitrophenylethyl)-phosphate] A $_{(Rp,Sp)}$*Ap-triester 43+44

6-N-Benzoyl-3'-O-[(tert-butyl)dimethylsilyl]-adenosine-2'-[2,5-dichlorophenyl,2-(4-nitrohenyl)-ethylphosphate]5'-OH-Ap-triester 40 (0.52 g; 0.6 mmole) and the phosphoramidite 15 (0.95 g; 0.9 mmole) were dissolved in absolute CH₃CN (6.5 ml) in the presence of tetrazole (0.126 g, 1.8 mmole) and under nitrogen atmosphere. After stirring for 3 h at r.t., S₈ (0.39 g, 1.51 mmole) and absolute pyridine (3.9 ml) were added and the reaction mixture was further stirred for 20 h, then extracted with CH₂Cl₂ (2×80 ml) and H₂O (2×80 ml). The organic phase was collected, dried over Na₂SO₄ and evaporated to dryness. Final coevaporation was done with toluene (4×20 ml) to remove the pyridine. The crude diastereomeric mixture $A_{(Rp,Sp)}$*Ap-triester 43+44 was purified by flash silica gel column chromatography (14×2.5 cm), using 200 ml CH₂Cl₂, CH₂Cl₂/1% MeOH, 2% MeOH and finally 200 ml CH₂Cl₂/1% MeOH, 2% MeOH and finally CH₂Cl₂/3% MeOH as eluants. The product fraction (150 ml) was evaporated to a solid foam, which was dried in high vacuum to give 0.975 g (88%) of (43) and (44) as a diastereomeric mixture. Anal. calc. for $A_{(Rp,Sp)}$*Ap-triester 43+44=$C_{88}H_{94}N_{12}O_{19}Cl_2P_2SSi_2$ (1844.9): C 57.29, H 5.14, N 9.11. Found: C 56.96, H 5.16, N 9.09. UV (MeOH): $\lambda_{max}$ (logε): 277 (4.75); [228 (4.72)]. $R_f$ on silica gel with toluene/EtOAc/CHCl₃ (1/1/1, v/v/v)=0.21. ³¹P-NMR (CDCl₃) 69.87, 69.25, −6.89, −7.22 and −7.31 ppm.

PREPARATION 14 a. Triethylammonium-N-6-benzoyl-3'-O-[(tert-butyl)-dimethylsilyl]-5')-(monomethoxytrityl)-(PR)-P-thioadenylyl-2'-[(O^P-2-(4-nitrophenyl)-ethyl-5']-N-6-benzoyl-3'-O-[(tert-butyl)dimethylsilyl]-adenosine-2'-[2-(4-nitrophenylethyl)-phosphate]
$A_{Rp}$*Ap-diester 45 b. Triethylammonium-N-6-benzoyl-3'-O-[(tert-butyl)-dimethylsilyl]-5')-(monomethoxytrityl)-(PS)-P-thioadenylyl-2'-[(O^P-2-(4-nitrophenyl)-ethyl -5']-N-6-benzoyl-3'-O-[(tert-butyl)dimethylsilyl]-adenosine-2'-[2-(4-nitrophenylethyl)-phosphate]
$A_{Sp}$*Ap-diester 46

The solution of 0.558 g (3.36 mmole) of 4-nitrobenzaldehyde oxime in 15 ml of H₂O/dioxane/Et₃N (1:1:1) was stirred for 30 min at r.t. Then, 0.62 g (0.336 mmole) of the diastereomeric mixture of the $A_{(Rp,Sp)}$*Ap-triester 43+44 was added and stirred for 2.5 h at r.t. The mixture was evaporated, then coevaporated with pyridine (3×15 ml), toluene (3×15 ml) and finally with CH₂Cl₂ (3×15 ml). The residue was dissolved in a small amount of CHCl₃ and chromatographed on a flash silica gel column (15×2.5 cm) with CHCl₃ (150 ml), CHCl₃/2% MeOH (200 ml), 4% MeOH (100 ml), 6% MeOH (200 ml), CHCl₃/6% MeOH/ 0.5% Et₃N (300 ml) and CHCl₃/6% MeOH/2% Et₃N (250 ml). The product fraction (600 ml) was evaporated to a solid foam, which was dried under high vacuum to give 0.55 g (91%) of the isomeric mixture 45+46. Separation into the pure diastereomers was achieved by chromatography on preparative silica gel plates (7 plates, 40×20×0.2 cm) and three developments in CHCl₃/MeOH (9/1, v/v). The product bands were eluted with CHCl₃/MeOH (4/1, v/v) containing 1% Et₃N and evaporated to a solid foam to give 0.262 g (43%) of $A_{Rp}$*Ap-diester 45, 0.144 (24%) of $A_{Sp}$*Ap-diester 46 and 0.045 g (7%) of $A_{(Rp,Sp)}$*Ap-diester 45+46. Anal. calc. for $A_{Rp}$*Ap-diester 45=$C_{88}H_{107}N_{13}O_{19}P_2SSi_2$×2 H₂O (183.7.1) C 57.53, H 6.09, N 9.91. Found: C 57.30, H 6.70, N 9.75. UV (MeOH): $\lambda_{max}$ (logε); 277 (4.69); [260 (4.56)]; [231 (4.61)]. $R_f$ on silica gel with CHCl₃/MeOH (9/1, v/v)=0.37. ³¹P-NMR (CDCl₃): 69.66 and −0.09 ppm. Anal. calc. for $A_{Sp}$*Ap-diester 46=$C_{88}H_{107}N_{13}O_{19}P_2SSi_{2×2}$ H₂O (1837.1): C 57.53, H 6.09, N 9.91. Found: C 56.44, H 7.15, N 8.61. UV (MeOH): $\lambda_{max}$ (logε); 276 (4.60); [260 (4.49)]; [232 (4.52)]. $R_f$ on silica gel with CHCl₃/MeOH (9/1, i/v)=0.28. ³¹P-NMR (CDCl₃): 68.96 and −0.06 ppm.

Scheme 5 is the reaction scheme for the preparation of the remaining fully resolved tetramers, ApAp$A_{Rp}$*A 51, ApAp$A_{Sp}$*A 52, $A_{Rp}$*ApApA 57, and $A_{Sp}$*ApApA 58, from their respective protected intermediates, 47, 48, 53 and 54. The corresponding preparations are outlined in Preparation 15, 16, and 17 and Examples 4 and 5.

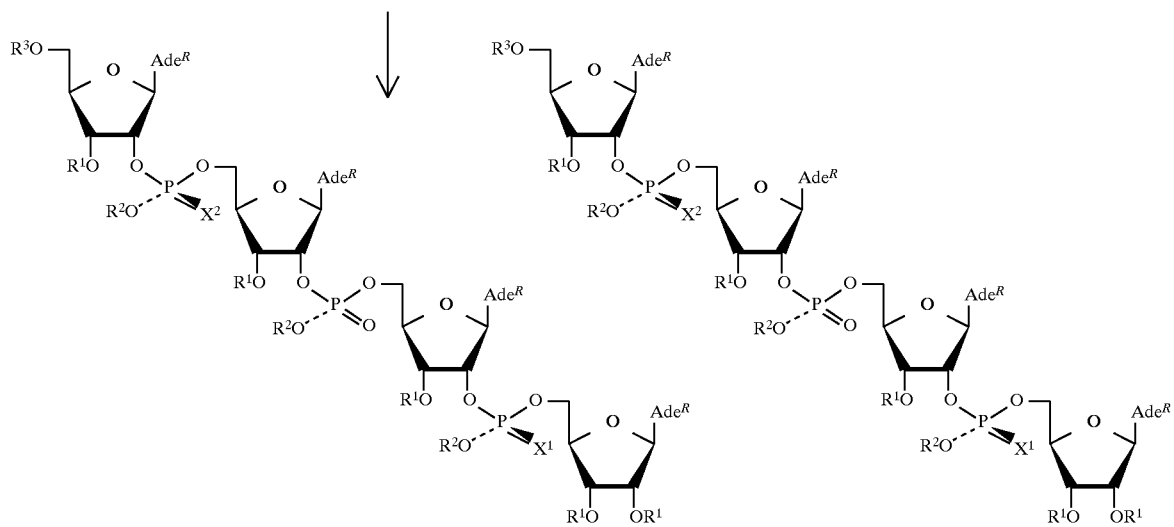

| | $X^1$ | $X^2$ | R | $R^1$ | $R^2$ | $R^3$ | |
|---|---|---|---|---|---|---|---|
| 47 | S | O | bz | tbds | npe | MeOTr | (ApApA$_{Rp}$A) |
| 49 | S | O | bz | tbds | npe | H | |
| 51 | S | O | H | H | NH$_4$ | H | |
| 53 | O | S | bz | tbds | npe | MeOTr | (A$_{Rp}$ApApA) |
| 55 | O | S | bz | tbds | npe | H | |
| 57 | O | S | H | H | NH$_4$ | H | |

-continued

| | $X^1$ | $X^2$ | R | $R^1$ | $R^2$ | $R^3$ | |
|---|---|---|---|---|---|---|---|
| 48 | S | O | bz | tbds | npe | MeOTr | (ApApA$_{Sp}$A) |
| 50 | S | O | bz | tbds | npe | H | |
| 52 | S | O | H | H | NH$_4$ | H | |
| 54 | O | S | bz | tbds | npe | MeOTr | (A$_{Sp}$ApApA) |
| 56 | O | S | bz | tbds | npe | H | |
| 58 | O | S | H | H | NH$_4$ | H | |

PREPARATION 15 a. 6-N-Benzoyl-3'-O-[(tert-butyl)dimethylsilyl]-5'-O-(monomethoxytrityl)-adenylyl-2'-[(O$^P$-2-(4-nitrophenyl)ethyl-5']-6-N-benzoyl-3'-O-[(tert-butyl)-dimethylsilyl]-adenylyl-2'-[(O$^P$-2-(4-nitrophenyl)ethyl-5']-6-N-benzoyl-3'-O-[(tert-butyl)dimethylsilyl]-(PR)-P-thioadenylyl-2'-[(O$^P$-2-(4-nitrophenyl)ethyl-5']-6-N-benzoyl-2',3'-di-O-[(tert-butyl)-dimethylsilyl]-adenosine ApApA$_{Rp}$*A 47

Triethylammonium 6-N-benzoyl-3'-O-[(tert-butyl)-dimethylsilyl]-5'-O-(monomethoxytrityl)-adenylyl-2'-[(O$^P$-2-(4-nitrophenyl)ethyl-5']-6-N-benzoyl-3'-O-[(tert-butyl)dimethylsilyl]-adenosine-2'-[2-(4-nitrophenyl)ethyl-phosphate] 42 (0.14 g; 0.078 mmole) and the 5'-hydroxy PR dimer 18 (0.08 g, 0.06 mole) were coevaporated with dry pyridine (4×0.5 ml), dissolved in dry pyridine (0.6 ml) and then (2,4,6-triisopropyl)benzenesulfonyl chloride (0.047 mg, 0.156 mmole) and 3-nitro-1,2,4-triazole (0.053 mg, 0.47 mmole) were added. The solution was stirred at r.t. for 22 h, extracted with CH$_2$Cl$_2$ (2×30 ml), washed with H$_2$O (2×20 ml), dried over Na$_2$SO$_4$ and evaporated to dryness. Pyridine was removed by coevaporation with toluene (3×20 ml). The crude tetramer 47 was purified by flash silica gel column chromatography (15×1 cm) and eluted first with CH$_2$Cl$_2$ (50 ml), then with CH$_2$Cl$_2$/1% MeOH (100 ml), 2% MeOH (50 ml) and finally with CH$_2$Cl$_2$/3% MeOH (100 ml). The product fraction (80 ml) was evaporated to dryness to give 0.11 g (62%) of the fully protected tetramer ApApA$_{Rp}$*A 47 as a colorless foam after drying under high vacuum at 350° C. Anal. calc. for C$_{142}$H$_{172}$N$_{23}$O$_{32}$P$_3$SSi$_5$×H$_2$O (2996.5): C 56.92, H 5.85, N 10.75. Found: C 56.51, H 5.91, N 10.37. UV (MeOH): $\lambda_{max}$ (logε) 277 (4.99); [259 (4.84)]; [233 (4.85)]. R$_f$ on silica gel with CHCl$_3$/MeOH (19/1, v/v)=0.46.

b. 6-N-Benzoyl-3'-O-[(tert-butyl)dimethylsilyl]-5'-O-(monomethoxytrityl)-adenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)-ethyl-5']-6-N-benzoyl-3'-O-[(tert-butyl)dimethylsilyl]-(PS)-P-thioadenylyl-2'-[(O$^P$-2-(4-nitrophenyl)ethyl-5']-6-N-benzoyl-2',3'-di-O-[(tert-butyl)-dimethylsilyl]-adenosine ApApA$_{Sp}$*A 48

ApAp-diester 41 (0.14 g, 0.078 mmole) and the 5'-hydroxy PS dimer 19 (0.08 g, 0.06 mmole) were coevaporated with dry pyridine (4×0.5 ml), dissolved in dry pyridine (0.6 ml) and then (2,4,6-triisopropyl)benzenesulfonyl chloride (0.47 mg, 0.156 mmole) and 3-nitro-1,2,4-triazole (0.053 mg, 0.46 mmole) were added. After stirring for 4.5 h at r.t., (2,4,6-triisopropyl)benzenesulfonyl chloride (0.024 g, 0.078 mmole) and 3-nitro-1,2,4-triazole (0.027 g, 0.234 mmole) were added again. The solution was stirred at r.t. for 16.5 h, then extracted with CH$_2$Cl$_2$ (4×20 ml) and added with H$_2$O (3×20 ml), dried over Na$_2$SO$_4$ and evaporated. Final coevaporations were done with toluene (4×15 ml) to remove pyridine. The crude tetramer 48 was purified by flash silica gel column chromatography (15×1 cm) and eluted analogous to tetramer 47 with CH$_2$Cl$_2$ and CH$_2$Cl$_2$/1–3% MeOH to give 0.107 g (60%) of the fully protected tetramer ApApA$_{Sp}$*A 48 as a colorless foam after drying under high vacuum at 35° C. Anal. calc. for C$_{142}$H$_{172}$N$_{23}$O$_{32}$P$_3$SSi$_5$×H$_2$O (2996.5): C 56.92, H 5.85, N 10.75. Found: C 56.51, H 5.91, N 10.85. UV (MeOH): $\lambda_{max}$ (logε) 277 (4.99); [259 (4.85)]; [231 (4.86)]. R$_f$ on silica gel with CHCl$_3$/MeOH (19/1, v/v)=0.46.

PREPARATION 16 a. 6-N-Benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-(PR)-P-thioadenylyl-2'-[(O$^P$-2-(4-nitrophenyl)ethyl-5']-6-N-benzoyl-2',3'-di-O-[(tert-butyl)dimethylsilyl]-adenosine 5'-OH-ApApA$_{Rp}$*A 49 b. 6-N-Benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-(PS)-P-thioadenylyl-2'-[(O$^P$-2-(4-nitrophenyl)ethyl-5']-6-N-benzoyl-2',3'-di-O-[(tert-butyl)dimethylsilyl]-adenosine 5'-OH-ApApA$_{Sp}$*A 50

The fully protected tetramer ApApA$_{Rp}$*A 47 (0.104 g, 0.035 mmole) was stirred with 2% p-TsOH in CH$_2$Cl$_2$/MeOH (4/1, v/v, 1.4 ml) at r.t. After 1.5 h, the reaction mixture was extracted with CH$_2$Cl$_2$ (3×40 ml) and H$_2$O (2×40 ml). The combined organic phase was dried over Na$_2$SO$_4$ and evaporated to dryness. The crude product was purified on a flash silica gel column (11×1 cm) and the product eluted with 20 ml CH$_2$Cl$_2$ and 50 ml CH$_2$Cl$_2$/1% MeOH to 5% MeOH. The product fraction (100 ml) was evaporated and dried under high vacuum to give 0.075 g (80%) of the hydroxy tetramer ApApA$_{Rp}$*A 49. Anal. calc. for C$_{122}$H$_{156}$N$_{23}$O$_{31}$P$_3$SSi$_5$×H$_2$O (2706.5): C 54.15, H 5.81, N 11.90. Found: C 53.97, H 6.02, N 11.65. UV (MeOH): $\lambda_{max}$ (logε) 277 (5.00); [260 (4.85)]; [234 (4.77)]. R$_f$ on silica gel with CHCl$_3$/MeOH (19/1, v/v)=0.43.

The fully protected tetramer ApApA$_{Sp}$*A 48 was treated in an analogous manner through the purification stage. The crude product 50 was purified on two preparative silica gel plates (20×20×0.2 cm) in CHCl$_3$/MeOH (19/1, v/v), the product band was eluted with CH$_2$Cl$_2$/MeOH (4/1, v/v) and evaporated to a solid foam to give 0.068 g (72%) of the 5'-hydroxy tetramer ApApA$_{Sp}$*A 50.

EXAMPLE 4 a. Adenylyl-(2'-5')-adenylyl-(2'-5')-(PR)-P-thioadenylyl-(2'-5')-adenosine ApApA$_{Rp}$*A 51 b. Adenylyl-(2'-5')-adenylyl-(2'-5')-(PS)-P-thioadenylyl-(2'-5')-adenosine ApApA$_{Sp}$*A 52

The corresponding 5'-hydroxy tetramers 49 and 50, respectively, were deblocked separately by stirring the 5'-hydroxy tetramer (0.067 g, 0.025 mmole) with 0.5M DBU in absolute $CH_3CN$ (3 ml) at r.t. for 20 h, the solution was neutralized with 1M AcOH in absolute $CH_3CN$ (1.5 ml) and evaporated to dryness. [$R_f$ on silica gel with {EtOAc/i-PrOH/ammonia/$H_2O$, 7/1/2, v/v/v) 7/3, v/v: ApAp$A_{Rp}$*A= 0.58; ApAp$A_{Sp}$*A=0.66. The residue was then treated with methanolic ammonia (10 ml) and after 3 days reaction time, the solvent was removed under vacuum. [$R_f$ on silica gel with EtOAc/i-PrOH/ammonia/$H_2O$, 7/1/2, v/v/v) 1/1, v/v}: ApAp$A_{Rp}$*A=0.38; ApAp$A_{Sp}$*A=0.36]. Desilylation was done with 1M $Bu_4NF$ in THF (5 ml). The reaction mixture was stirred at r.t. for 48 h and then the solvent was evaporated in vacuum. The residue was taken up in $H_2O$ (10 ml) and applied to a DEAE Sephadex A-25 column (30×2 cm). With flow rates of 2 ml/min, the pure tetramer ApAp$A_{Rp}$*A was eluted with 0.15–0.20M TEAB buffer, pH 7.5, and in the case of the tetramer ApAp$A_{Sp}$*A with 0.24–0.32M TEAB buffer, pH 7.5. After evaporation and coevaporation with MeOH several times, the tetramer was applied onto eight paper sheets (25×50 cm) and developed in i-PrOH/ammonia/$H_2O$ (6/1/3, v/v/v). The product band was cut out, eluted with $H_2O$, concentrated to a smaller volume and finally lyophilized to give 675 O.D.$_{260\ nm}$ units (57%) of ApAp$A_{Rp}$*A isomer 51 and 753 O.D.$_{260\ nm}$ (65%) of ApAp$A_{Sp}$*A isomer 52. ApAp$A_{Rp}$*A 51: $R_f$ on cellulose in i-PrOH/ammonia/$H_2O$ (6/1/3, v/v/v)=0.33. UV ($H_2O$): $\lambda_{max}$ 258 nm. HPLC: PR-18, A: 50 mM $NH_4H_2PO_4$, pH 7.2. B: MeOH/$H_2O$ (1/1, v/v), gradient: 0–1 min, 80% A, 20% B; 1–31 min, 30% A, 70% B; retention time: 9.70 min. ApAp$A_{Sp}$*A 52: $R_f$ on cellulose in i-PrOH/ammonia/$H_2O$ (6/1/3, v/v/v)=0.21. UV ($H_2O$): $\lambda_{max}$ 258 nm. HPLC: PR-18, A: 50 mM $NH_4H_2PO_4$, pH 7.2. B: MeOH/$H_2O$ (1/1, v/v), gradient: 0–1 min, 80% A, 20% B; 1–31 min, 30% A, 70% B; retention time: 13.49 min.

PREPARATION 17 a. 6-N-Benzoyl-3'-O-[(tert-butyl)dimethylsilyl]-5'-O-(monomethoxytrityl)-(PR)-P-thioadenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-2',3'-di-O-[(tert-butyl)dimethylsilyl]-adenosine A$_{Rp}$*ApApA 53

Triethylammonium 6-N-benzoyl-3'-O-[(tert-butyl)-dimethylsilyl]-5'-O-(monomethoxytrityl)-(PR)-P-thioadenylyl-2'-[(O$^P$-2-(4-nitrophenyl)ethyl-5']-6-N-benzoyl-3'-O-[(tert-butyl)dimethylsilyl]-adenosine-2'-[(O$^P$-2-(4-nitrophenyl)ethyl-phosphate] A$_{Rp}$*Ap-diester 45 (0.141 g, 0.078 mmole) and the 5'-hydroxy dimer 29 (0.078 g, 0.06 mmole) were coevaporated with dry pyridine (4×0.5 ml) and finally dissolved in dry pyridine (0.6 ml). Then (2,4,6-triisopropyl)-benzenesulfonyl chloride (0.047 mg, 0.156 mmole) and 3-nitro-1,2,4-triazole (0.053 mg, 0.47 mmole) were added and stirred at r.t. for 21 h. The reaction mixture was diluted with $CH_2Cl_2$ (60 ml) and washed with $H_2O$ (2×30 ml), dried over $Na_2O_4$ and evaporated to dryness. Pyridine was removed by coevaporation with toluene (3×20 ml). The crude tetramer 53 was purified by flash silica gel column chromatograpy (11×1 cm) and eluted first with $CH_2Cl_2$ (50 ml), then with $CH_2Cl_2$/1% MeOH (100 ml), 2% MeOH (200 ml), 3% MeOH (50 ml) and finally with $CH_2Cl_2$/5% MeOH (50 ml). The product fraction (200 ml) was evaporated to dryness. The residue was chromatographed again on two preparative silica gel plates (20×20×0.2 cm) in toluene/EtOAc/MeOH (5/4/0.5, v/v/v) to remove small amount of 5'-hydroxy dimer. The tetramer product band was eluted with $CH_2Cl_2$/MeOH (4/1, v/v) and evaporated to a solid foam to give 0.053 g (30%) of the tetramer A$_{Rp}$*ApApA 53 after drying in high vacuum at 35° C. Anal. calc. for $C_{142}H_{172}N_{23}O_{32}P_3SSi_5$×3 $H_2O$ (3032.5): C 56.24, H 5.92, N 10.62. Found: C 55.75, H. 5.71, N 9.83. UV (MeOH): $\lambda_{max}$ (logε) 277 (4.96); [260 (4.82)]; [232 (4.82)]. $R_f$ on silica gel with toluene/EtOAc/MeOH (5:4:1)=0.78.

b. 6-N-Benzoyl-3'-O-[(tert-butyl)dimethylsilyl]-5'-O-(monomethoxytrityl)-(PS)-P-thioadenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-3'-O-[(tert-butyl)dimethylsilyl]-adenylyl-2'-[(O$^P$-2-(4-nitrophenyl)ethyl-5']-6-N-benzoyl-2',3'-di-O-[(tert-butyl)dimethylsilyl]-adenosine A$_{Sp}$*ApApA 54

A$_{Sp}$*Ap-diester 46 (0.141 g, 0.078 mmole) and the 5'-hydroxy dimer 29 (0.078 g, 0.06 mmole) were coevaporated with dry pyridine (4×0.5 ml) and dissolved in dry pyridine (0.6 ml). (2,4,6-Triisopropyl)-benzenesulfonyl chloride (0.047 mg, 0.156 mmole) and 3-nitro-1,2,4-triazole (0.053 mg, 0.47 mmole) were added and the mixture was stirred at r.t. After 21 h, (2,4,6-triisopropyl)benzenesulfonyl chloride (0.024 mg, 0.079 mmole) and 3-nitro-1,2,4-triazole (0.027 mg, 0.24 mmole) were added again. The reaction mixture was stirred for another hour, then diluted with $CH_2Cl_2$ (60 ml) and washed with $H_2O$ (2×30 ml), dried over $Na_2SO_4$ and evaporated to dryness. Further work-up was performed analagous to that described for tetramer 53 to give 43 mg (24%) of A$_{Sp}$*ApApA 54 in the form of a solid foam. Anal. calc. for $C_{142}H_{172}N_{23}O_{32}P_3SSi_5$×$H_2O$ (2996.5): C 56.92, H 5.85, N 10.75. Found: C 56.63, H 6.08, N 10.18. UV (MeOH): $\lambda_{max}$ (logε) 277 (4.98); [260 (4.84)]; [232 (4.85)]. $R_f$ on silica gel with toluene/EtOAc/MeOH (5/4/1, v/v/v)=0.78.

EXAMPLE 5 a. (PR)-P-Thioadenylyl-(2'-5')-adenylyl-(2'-5')-adenylyl-(2'-5')-adenosine A$_{Rp}$*ApApA 57 b. (PS)-P-Thioadenylyl-(2'-5')-adenylyl-(2'-5')-adenylyl-(2'-5')-adenosine A$_{Sp}$*ApApA 58

The corresponding fully protected tetramers 53 and 54 were deblocked by stirring a solution of 0.047 g (0.016 mmole) of PR tetramer 53 (PS tetramer 54: 0.032 g, 0.012 mmole) in 2% p-TsOH in $CH_2Cl_2$/MeOH (4/1; v/v; for PR: 0.5 ml; for PS: 0.38 ml) for 1 h at r.t. The reaction mixture was diluted with $CH_2Cl_2$ (60 ml), washed with $H_2O$ (2×30 ml), dried over $Na_2SO_4$ and evaporated to dryness. The crude products were purified on preparative silica gel plates (20×20×0.2 cm) in $CHCl_3$/MeOH (19/1, v/v), the product bands were eluted with $CH_2Cl_2$/MeOH (4/1, v/v) and evaporated to solid foams to give 0.034 g (80%) of the 5'-hydroxy A$_{Rp}$*ApApA isomer 55 and 0.02 g (68%) of the 5'-hydroxy A$_{Rp}$*ApApA isomer 56. The solution of the 5'-hydroxy tetramers 55 (0.034 g, 0.013 mmole) and 56 (0.02 g, 0.007 mmole), respectively, were separately stirred with 0.5M DBU in absolute $CH_3CN$ [(55: 1.5 ml; 56: 0.9 ml)] for 18 h at r.t., then neutralized by addition of 1M AcOH [(55: 0.75 ml; 56: 0.45 ml)] and evaporated. The residue was treated with 10 ml of saturated methanolic ammonia and the solution, after stirring at r.t. for 60 h, was evaporated to dryness. Desilylation was done by treatment with 1M $Bu_4NF$ in THF (2.5 ml). After stirring at r.t. for 60 h, the solvent was removed under vacuum. Some $H_2O$ (10 ml) was added to the resulting residue and applied to a DEAE Sephadex column A-25 (32×2 cm) and eluted with 0–0.5M TEAB buffer, pH 7.5. The fractions of the main peak were collected, evaporated and coevaporated several times with MeOH. Further purification by paper chromatography (i-PrOH/ammonia/$H_2O$, 55/10/35, v/v/v) gave, after lyophilization, 347 O.D.$_{260\ nm}$ units (58%) of $A_{Rp}$\*ApApA 57 and 111 O.D.$_{260\ nm}$ units (31%) of $A_{Sp}$\*ApApA 58, respectively. $A_{Rp}$\*ApApA 57: UV ($H_2O$)=257 nm. $R_f$ on cellulose in i-PrOH/ammonia/$H_2O$ (6/1/3, v/v/v)=0.21. HPLC: PR-18, A: 50 mM $NH_4H_2PO_4$ (pH 7.2). B: MeOH/$H_2O$ (1/1, v/v), gradient: 0–1 min, 80% A, 20% B; 1–31 min, 30% A, 70% B; retention time: 7.47 min. $A_{Sp}$\*pApA 58: UV ($H_2O$)=257 nm. $R_f$ on cellulose in iPrOH/ammonia/$H_2O$ (6/1/3, v/v/v)=0.32. HPLC: PR-18, A: 50 mM $NH_4H_2PO_4$, pH 7.2. B: MeOH/$H_2O$ (1/1, v/v), gradient: 0–1 min, 80% A, 20% B; 1–31 min, 30% A, 70% B; retention time: 9.84 min.

Preparation of 2',5'-Phosphorothioate/
Phosphodiester Oligoadenylate 5'-Monophosphates The phosphorothioate/phosphodiester trimer and tetramer cores were synthesized as described above in Examples 1, 2, 3, 4, and 5. The trimer and tetramer 5'-monophosphates were enzymatically synthesized according to the procedure of Sambrook et al., *Molecular Cloning— A Laboratory Manual*, 2 ed., Cold Spring Harbor Laboratory Press, pp. 5.68–5.71 (1989) from their corresponding cores and ATP with T4 polynucleotide kinase. 5'-Monophosphorylation was determined by reverse-phase HPLC analysis and confirmed by the subsequent hydrolysis of each 5'-monophosphate derivative by 5'-nucleotidase (data not shown). Yields of phosphorylation ranged from 15% to 68%.

Preparation of 2',5'-Phosphorothioate/
phosphodiester Oligoadenylate 5'-Diphosphate and
5'-Triphosphate The 5'-diphosphate and 5-triphosphate of the 2',5'-phosphorothioate/phosphodiester oligoadenylates may be prepared from the 5'-monophosphate by following the procedure of Example 6.

EXAMPLE 6

All reactions are performed in glassware oven-dried at 125° C. for 18–24 hr. A 2',5'-phosphorothioate/phosphodiester oligoadenylate stereoisomer (trimer or tetramer, 400 OD units at 260 nm) is dissolved in 500 microliters of dry dimethylformamide ("DMF") and dried in vacuo in a 10 ml conical flask at 35° C. This process is repeated three times. To the dry residue, 50 micromoles of triphenylphosphine, 100 micromoles of imidazole and 50 micromoles of dipyridinyl disulfide are added. The mixture is dissolved in 500 microliters dry DMF plus 50 microliters of dry dimethylsulfoxide. The solution is stirred with a stirring bar for 2 hr at room temperature. After 2 hr the solution is homogeneous (after 30 minutes, the solution begins to change to yellow). The solution is transferred dropwise to 10 ml of a 1% NaI/dry acetone (w/v) solution. The clear colorless precipitate which forms is the sodium salt of the 5'-phosphoroimidazolidate. The precipitate is centrifuged at room temperature, the supernatant is decanted, and the precipitate is washed three times with 10 ml dry acetone. The centrifuging is repeated. The precitipate is dried over $P_2O_5$ in vacuo for 2 hr. The precipitate is dissolved in 200 microliters of freshly prepared 0.5M tributylammonium pyrophosphate in dry DMF. The solution is maintained at room temperature for 18 hr after which time the DMF is removed in vacuo. The residue is dissolved in 0.25M triethylammonium bicarbonate buffer ("TEAB") (pH 7.5). The 5'-di and 5'-triphosphate products are separated using a DEAE-Sephadex A25 column ($HCO_3$-form; 1×20 cm) with a linear gradient of 0.25M to 0.75N TEAB. Fractions (10 ml) are collected. The product is observed by ultraviolet spectroscopy at 254 nm. The fractions containing the 5'-di and 5'-triphosphates are separately pooled and dried in vacuo. by lyophilization. The yield of the 5'-diphosphate is about 5%; the yield of the 5'-triphosphate is about 60%.

Stability of the Phosphorothioate/Phosphodiester
Trimer and Tetramer Core Derivatives to Serum
Phosphodiesterase The stability of authentic 2-5A and phosphorothioate/phosphodiester trimer and tetramer core derivatives (300 μM) was determined by incubation in 200 μL of RPMI-1640 medium supplemented with 10% fetal calf serum in 5% $CO_2$-in-air at 37° C. Aliquots (30 μL) were removed at time zero and 6 hours. The hydrolysis products were identified by HPLC as described in Kariko et al. , *Biochemistry* 26: 7127–7135 (1987). Under the conditions described therein, authentic $A_2$ and $A_3$ were completely hydrolyzed to inosine and hypoxanthine in 20 min (Table 1), while $A_{Rp}$\*A and $A_{Sp}$\*A were not hydrolyzed.

No hydrolysis of the phosphorothioate/phosphodiester trimer core derivatives was observed. However, the phosphorothioate/phosphodiester tetramer core derivatives were hydrolyzed from the 5'- or 2',3'-terminus, depending on the location of the phosphorothioate-substituted internucleotide linkage. For example, $A_{Rp}$\*ApApA and $A_{Sp}$\*ApApA were 50% degraded to their respective dimer cores, $A_{Rp}$\*A and $A_{Sp}$\*A, whereas $ApA_{Rp}$\*ApA and $ApA_{Sp}$\*ApA are degraded from the 2',3'-terminus to form the trimer cores, $ApA_{Rp}$\*A and $ApA_{Sp}$\*A. $ApApA_{Rp}$\*A and $ApApA_{Sp}$\*A are degraded from the 5'-terminus to yield $ApA_{Rp}$\*A and $ApA_{Sp}$\*A, respectively.

TABLE 1

Hydrolysis of Phosphorothioate/Phosphodiester Trimer and Tetramer
2–5A Core Derivatives by Serum Phosphodiesterases

| 2–5A or Derivative | % Hydrolysis[a] | Hydrolysis Products[b] |
|---|---|---|
| $A_2$ | 100 (20 min) | inosine, hypoxanthine |
| $A_3$ | 100 (20 min) | inosine, hypoxanthine |
| $A_{Rp}$\*A | 0[b] | not hydrolyzed |
| $A_{Sp}$\*A | 0[b] | not hydrolyzed |
| $A_{Rp}$\*ApA | 0 | not hydrolyzed |
| $A_{Sp}$\*ApA | 0 | not hydrolyzed |
| $ApA_{Rp}$\*A | 0 | not hydrolyzed |
| $ApA_{Sp}$\*A | 0 | not hydrolyzed |
| $A_{Rp}$\*ApApA | 100 | inosine, hypoxanthine, $A_{Rp}$\*A |
| $A_{Sp}$\*ApApA | 100 | inosine, hypoxanthine, $A_{Sp}$\*A |
| $ApA_{Rp}$\*ApA | 50 | inosine, hypoxanthine, $A_{Rp}$\*ApA |
| $ApA_{Sp}$\*ApA | 50 | inosine, hypoxanthine, $A_{Sp}$\*ApA |
| $ApApA_{Rp}$\*A | 30 | inosine, hypoxanthine, $ApA_{Rp}$\*A |
| $ApApA_{Sp}$\*A | 33 | inosine, hypoxanthine, $ApA_{Sp}$\*A |

[a]Incubations were for 6 h as described in text. Number in parentheses indicates the time at which 100% hydrolysis was observed.
[b]Identified as described by Kariko et al., Biochemistry 26: 7127-7135 (1987).

Binding of 2',5'-Phosphorothioate/Phosphodiester
Oligoadenylates to RNase L

The affinity of the phosphorothioate/phosphodiester 2-5A derivatives for RNase L was determined in radiobinding assays according to the method of Knight et al., *Meth. Enzymol* 79: 216–227 (1981). Authentic $A_3$, $pA_3$ and $p_3A_3$ bind to RNase L with $IC_{50}$, values of $1 \times 10^{-6}$M, $1 \times 10^{-9}$M and $1 \times 10^{-9}$M, respectively. According to the invention, the binding of the phosphorothioate/phosphodiester core and their 5'1-monophosphates to RNase L was equivalent to or slightly better than the corresponding authentic 2-5A cores and 5'-monophosphates, with $IC_{50}$ values from $8 \times 10^{-7}$M to $8 \times 10^{-6}$M for the cores and from $1 \times 10^{-8}$M to $1 \times 10^{-9}$M for the 5'-monophosphates. The trimer and tetramer 2-5A core derivatives with phosphorothioate substitution in the first internucleotide linkage from the 5'-terminus exhibited lower affinity compared to those with phosphorothioate substitution in the second or third internucleotide linkage.

Activation of RNase L by Phosphorothioate/Phosphodiester Derivatives of 2-5A Correlation of biological properties with absolute configuration has only been possible with the preparation of the fully resolved 2',5'-phosphorothioate/phosphodiester adenylate trimer cores. However, the trimer core compounds have been found to bind and/or activate RNase L only modestly. RNase L activation by the 2',5'-phosphorothioate core molecules is significantly enhanced by 5'-phosphorylation.

Figure 1A:
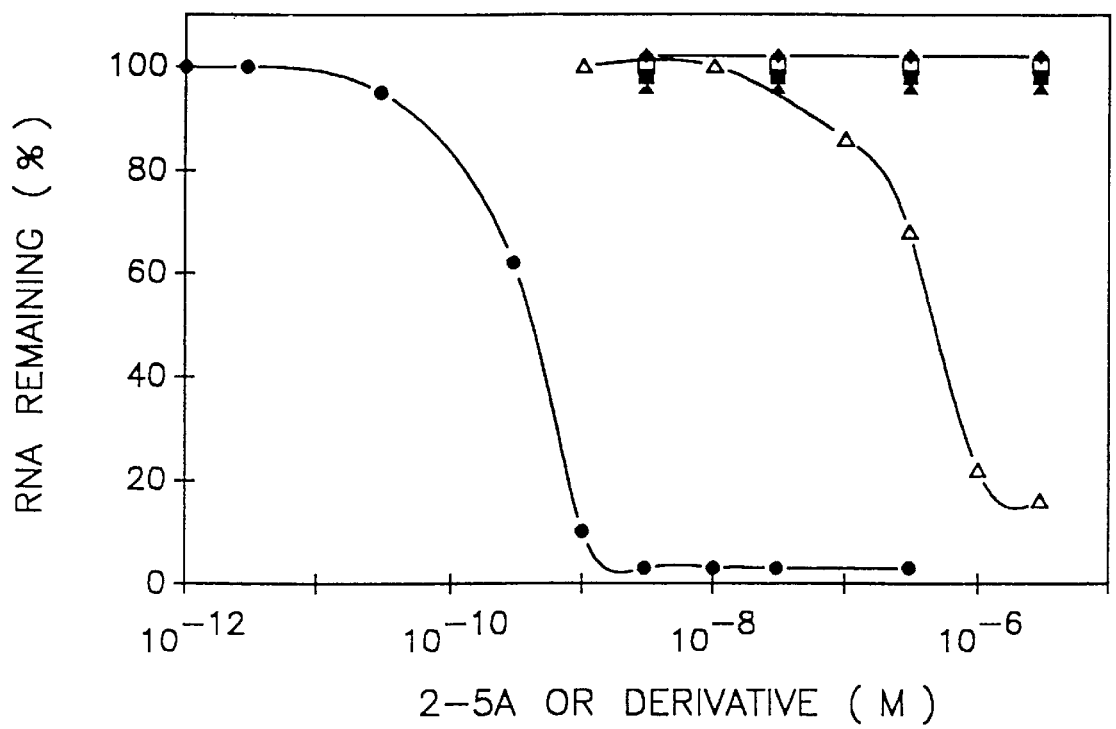
FIG. 1A represents the results of a radiobinding assay indicating the ability of 2',5'-phosphorothioate/ phosphodiester trimer core 2-5A derivatives to activate partially-purified RNase L from L929 cell extracts to hydrolyze the substrate poly(U) [$^{32}$P]pCp, but not poly(C). Activation of RNase L was determined by the conversion of poly(I) [$^{32}$P]pCp to acid soluble fragments. 100% represents 25,000 dpm of poly(U) [$^{32}$P]pCp bound to glass fiber filters. 2-5A oligomer (phosphodiester internucleotide linkage) is included for comparison. The curves are labeled as follows: $p_3A_3$ (●); $A_3$ (♦); $A_{Rp}$*ApA (□); $A_{Sp}$*ApA (■); $ApA_{Rp}$*A (△); and $ApA_{Sp}$*A (▲)
Figure 1B:
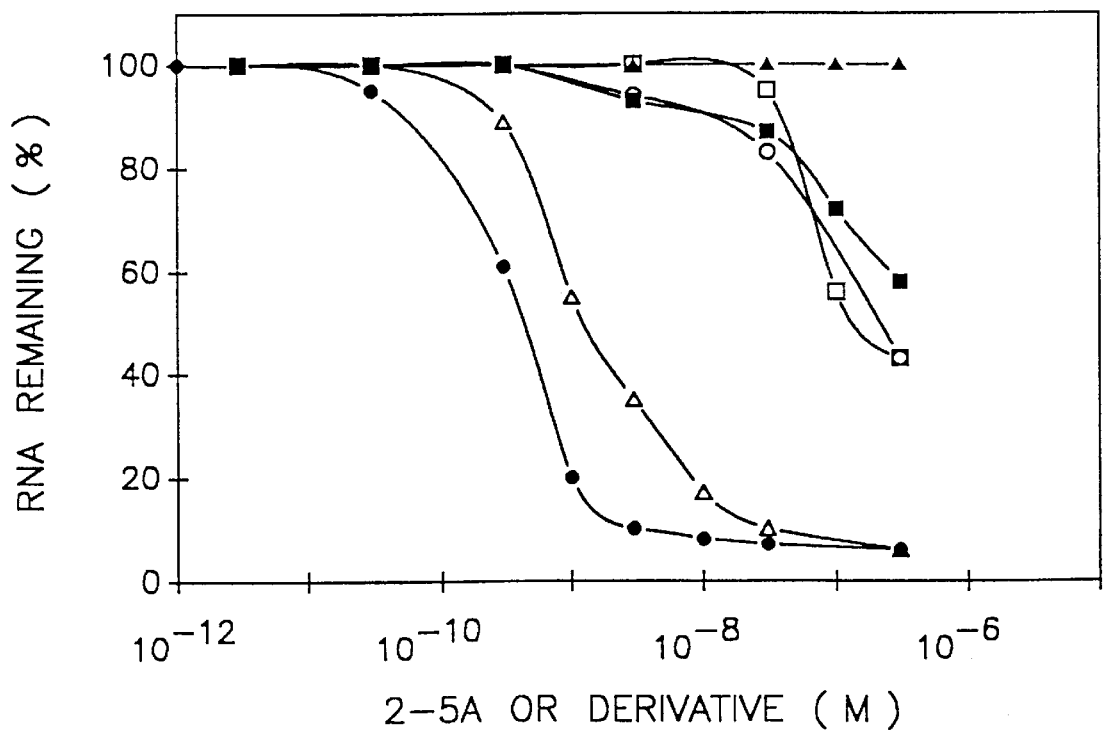
FIG. 1B represents the results of a radiobinding assay performed according to the method of FIG. 1A for 2',5'-phosphorothioate/phosphodiester trimer 5'-monophosphate 2-5A derivatives. The curves are labeled as follows: $p_3A_3$ (●); $pA_3$ (○); $pA_{Rp}$*ApA (□); $pA_{Sp}$*ApA (■); $pApA_{Rp}$*A (△); and $pApA_{Sp}$*A (▲).

Core-cellulose assays were performed according to the method of Silverman, *Anal. Biochem.* 144: 450–460 (1985) and Kariko et al. (1987), supra, in which RNase L was partially purified from L929 cell extracts by immobilization on 2-5$A_4$ core-cellulose. Activation of RNase L was measured by the conversion of poly(U) [$^{32}$p]pCp to acid soluble fragments. The results indicate that authentic $p_3A_3$, $p_3A_4$, $pA_3$ and $pA_4$ have $IC_{50}$ values of $5 \times 10^{-10}$M, $5 \times 10^{-10}$M, $2 \times 10^{-7}$M and $2 \times 10^{-8}$M, respectively, while surprisingly, of the phosphorothioate/phosphodiester trimer core derivatives, only $ApA_{Rp}$*A can activate RNase L ($IC_{50}$ of $5 \times 10^{-7}$M) (FIG. 1A, Δ). Three of the phosphorothioate/phosphodiester trimer 5'-monophosphates can activate RNase L, with $pApA_{Rp}$*A being the most potent activator of RNase L ($IC_{50}$ of $1 \times 10^{-9}$M) (FIG. 1B, Δ). $pA_{Rp}$*ApA (□) and $pA_{Sp}$*ApA (■) are 100-fold less potent activators of RNase L. Of the six phosphorothioate/phosphodiester tetramer core derivatives, only $ApA_{Rp}$*ApA (□) and $ApApA_{Rp}$*A (Δ) can activate RNase L ($IC_{50}$ of $5 \times 10^{-7}$M and $5 \times 10^{-7}$M, respectively) (FIG. 1C). Five of the six phosphorothioate/phosphodiester tetramer 5'-monophosphates activate RNase L ($IC_{50}$ values >$6 \times 10^{-7}$M to $8 \times 10^{-10}$M). The $pApA_{Sp}$*ApA enantiomer did not activate RNase L, even at concentrations as high as $1 \times 10^{-5}$M (FIG. 1D, ■).

Figure 2A:
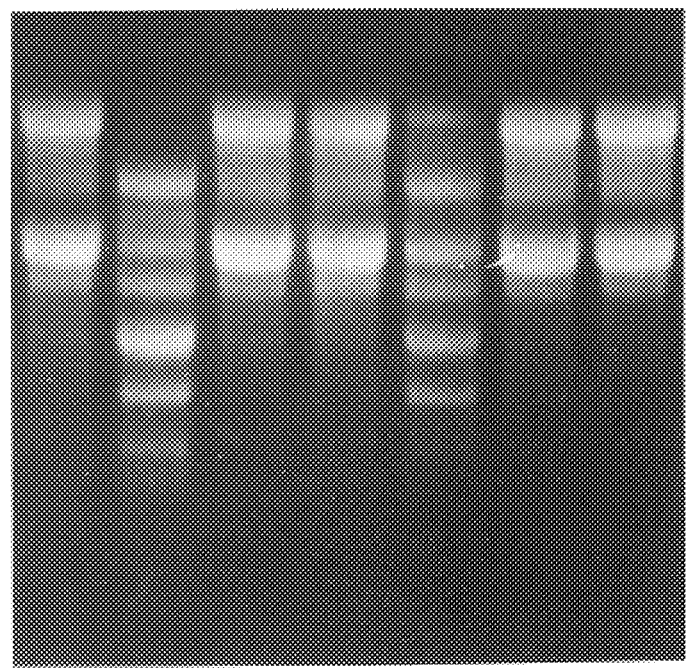
FIG. 2A represents the results of a ribosomal RNA cleavage assay with 2',5'-phosphorothioate/phosphodiester trimer core 2-5A derivatives. The procedure was performed according to the method of Kariko et al., *Biochemistry* 26: 7127–7135 (1987). 2-5A oligomer (phosphodiester internucleotide linkage) is also included for comparison. L929 cell extracts were incubated in the absence (lane 1) or presence of $p_3A_3$ at $10^{-8}$M (lane 2), $A_{Rp}$*ApA at $10^{-6}$M (lane 3), $A_{Sp}$*ApA at $10^{-6}$M (lane 4), $ApA_{Rp}$*A at $10^{-6}$M (lane 5), $ApA_{Sp}$*A at $10^{-6}$M (lane 6) or $A_3$ at $10^{-6}$M (lane 7). The positions of 28S and 18S rRNA are shown; the arrows indicate the positions of the well-characterized specific cleavage products (SCP) of RNase L.
Figure 2B:
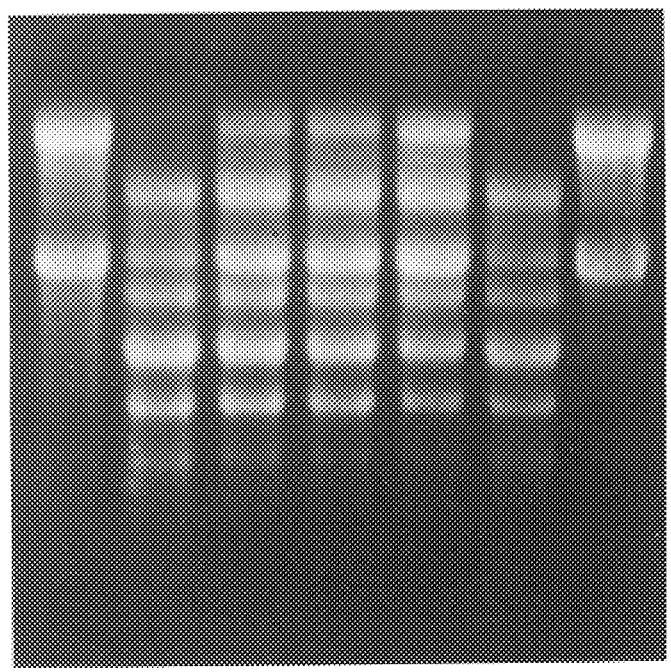
FIG. 2B represents the results of a ribosomal RNA cleavage assay performed according to the method of FIG. 2A with 2',5'-phosphorothioate/phosphodiester trimer 5'-monophosphate derivatives. L929 cell extracts were incubated in the absence (lane 1) or presence of $p_3A_3$ at $2\times10^{-9}$M (lane 2), $pA_3$ at $10^{-6}$M (lane 3), $pA_{Rp}$*ApA at $10^{-7}$M (lane 4), $pA_{Sp}$*ApA at $10^{-7}$M (lane 5), $pApA_{Rp}$*A at $2\times10^{-9}$M (Lane 6), $pApA_{Sp}$*A at $10^{-7}$M (lane 7).

Activation of RNase L by the phosphorothioate/phosphodiester trimer and tetramer 2-5A derivatives was also measured in a rRNA cleavage assay using L929 cell extracts according to the method of Kariko et al. (1987), supra, in which extracts of L929 cells were incubated for 1 h at 30° C. in the presence or absence of 2-5A or 2-5A derivative. Consistent with the results from the core-cellulose assays (FIG. 1A), $ApA_{Rp}$*A ($1 \times 10^{-6}$M) was the only trimer core able to activate RNase L to cleave rRNA to the well-characterized specific cleavage products (SCP) of RNase L (FIG. 2A, lane 5). $A_{Rp}$*ApA, $A_{Sp}$*ApA and $ApA_{Sp}$*A, as well as authentic $A_3$, did not activate RNase L at concentrations as high as $1 \times 10^{-6}$M (FIG. 2A, lanes 3, 4, 6, 7). Authentic $p_3A_3$ was active at $1 \times 10^{-8}$M (FIG. 2A, lane 2). The corresponding 5'-monophosphates, $pA_{Rp}$*ApA, $pA_{Sp}$*ApA and $pApA_{Rp}$*A, activated at $1 \times 10^{-7}$M, $1 \times 10^{-7}$M, and $2 \times 10^{-9}$M, respectively (FIG. 2B, lanes 4–6), as compared with $pA_3$ which was active at $1 \times 10^{-6}$M (lane 3). Incubation with $pApA_{Sp}$*A, even at concentrations as high as $5 \times 10^{-6}$M, did not result in detectable rRNA degradation (data not shown).

Figure 3A:
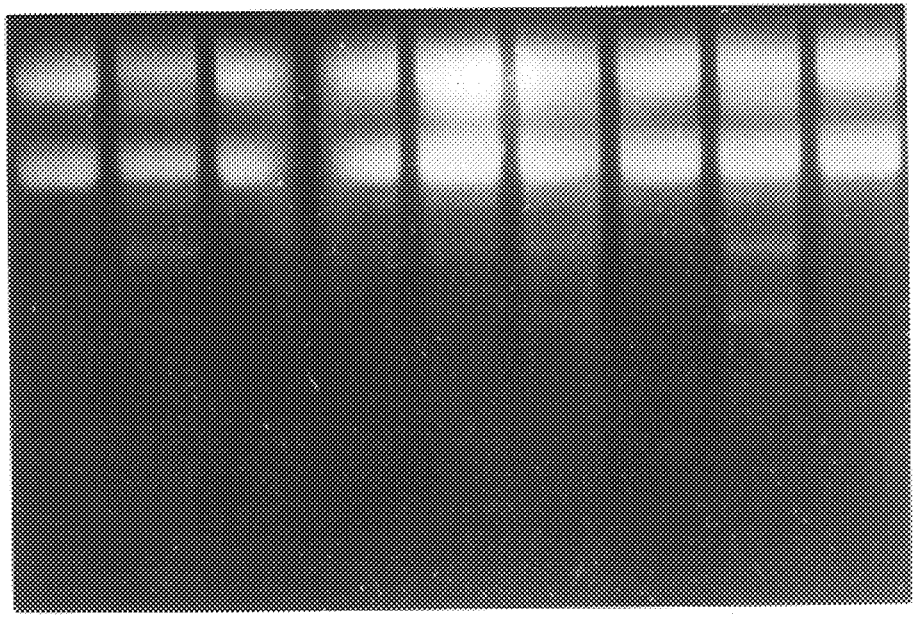
FIG. 3A represents the results of a ribosomal RNA cleavage assay performed according to the method of FIG. 2A with 2',5'-phosphorothioate/phosphodiester tetramer core 2-5A derivatives. 2-5A oligomer (phosphodiester internucleotide linkage) is also included for comparison. L929 cell extracts were incubated in the absence (lane 1) or presence of $p_3A_4$ at $10^{-8}$M (lane 2), $A_4$ at $10^{-5}$M (lane 3), $A_{Rp}$*ApApA at $10^{-5}$M (lane 4), $A_{Sp}$*ApApA at $10^{-5}$M (lane 5), $ApA_{Rp}$*ApA at $10^{-5}$M (lane 6), $ApA_{Sp}$*ApA at $10^{-5}$M (lane 7), $ApApA_{Rp}$*A at $10^{-5}$M (lane 8) or $ApApA_{Sp}$*A at $10^{-5}$M (lane 9).
Figure 3B:
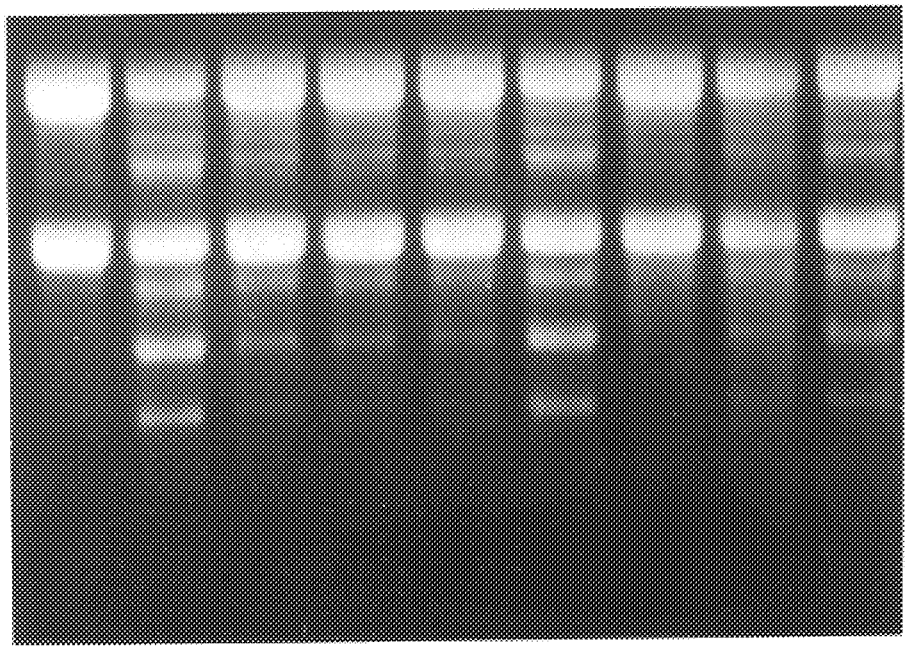
FIG. 3B represents the results of a ribosomal RNA cleavage assay performed according to the method of FIG. 2A with 2',5'-phosphorothioate/phosphodiester tetramer 5'-monophosphate derivatives. L929 cell extracts were incubated in the absence (lane 1) or presence of $p_3A_4$ at $10^{-8}$M (lane 2), $pA_4$ at $10^{-6}$M (lane 3), $pA_{Rp}$*ApApA at $10^{-6}$M (lane 4), $pA_{Sp}$*ApApA at $10^{-6}$M (lane 5), $pApA_{Rp}$*ApA at $10^{-8}$M (lane 6), $pApA_{Sp}$*ApA at $10^{-5}$M (lane 7), $pApApA_{Rp}$*A at $10^{-7}$M (lane 8) or $pApApA_{Sp}$*A at $10^{-7}$M (lane 9).

Comparable degradation of rRNA was observed with two of the six phosphorothioate/phosphodiester tetramer core derivatives relative to the authentic $p_3A_4$ control. $ApA_{Rp}$*ApA and $ApApA_{Rp}$*A activated RNase L at $1 \times 10^{-5}$M (FIG. 3A, lanes 6 and 8). As was observed in the core-cellulose assays (FIG. 1D), five of the six phosphorothioate/phosphodiester tetramer 5'-monophosphates were able to activate RNase L ($pA_{Rp}$*ApApA, $pA_{Sp}$*ApApA, $pApA_{Rp}$*ApA, $pApApA_{Rp}$*A, and $pApApA_{Sp}$*A) (FIG. 3B, lanes 4, 5, 6, 8, 9, respectively). The most efficient activator or RNase L was $pApA_{Rp}$*ApA ($1 \times 10^{-8}$M) (FIG. 3B, lane 6), while $pApA_{Sp}$*ApA was an antagonist of RNase L activation and was unable to activate RNase L even at concentrations as high as $1 \times 10^{-5}$M (FIG. 3B, lane 7).

Inhibition of RNase L Activation by $pApA_{Sp}$*A

The high affinity of $pApA_{Sp}$*A for RNase L and the observation that $pApA_{Sp}$*A does not activate RNase L, suggests that it might be a specific inhibitor of RNase L. Indeed, $pApA_{Sp}$*A inhibits the activation of RNase L by $p_3A_3$ or $pApA_{Rp}$*A (FIG. 4A). Authentic $p_3A_3$ activates RNase L to hydrolyze 28S and 18S rRNA to SCP at $10^{-9}$M or $10^{-8}$M (lanes 1 and 3). However, addition of $pApA_{Sp}$*A ($10^{-6}$M) results in the inhibition of RNase L-catalyzed hydrolysis of rRNA (lanes 2 and 4). Similarly, whereas $pApA_{Rp}$*A activates RNase L at $10^{-9}$M or $10^{-8}$M (lanes 5 and 7), the addition of $pApA_{Sp}$*A ($10^{-6}$M) inhibits this activation (lanes 6 and 8). The inhibitory activity of $pApA_{Sp}$*A was also observed with partially-purified RNase L (FIG. 4B). $p_3A_3$ activates RNase L with an $IC_{50}$ value of $5 \times 10^{-10}$M (●); however, upon addition of $pApA_{Sp}$*A ($1 \times 10^{-6}$M), the observed $IC_{50}$ value shifts to $1 \times 10^{-8}$M (○), demonstrating specific inhibition of $p_3A_3$-mediated activation of RNase L by $pApA_{Sp}$*A.

Notwithstanding, $pApA_{Sp}$*A is useful as a probe in the evaluation of the role of RNase L in the interferon-induced biological cascade. Most importantly, $pApA_{Sp}$*A selectively inhibits activation of RNase L at physiological concentrations, and is metabolically stable to specific and non-specific phosphodiesterases. The molecule provides the means to selectively inhibit RNase L activation.

Moreover, it is expected that $pApA_{Sp}$*A has therapeutic activity. Individuals afflicted with chronic myelogenous leukemia ("CML") display a highly elevated RNase L activity, as evidenced by novel rRNA CML-specific cleavage products. Thus, $pApA_{Sp}$*A, which is a metabolically stable inhibitor of RNase L, has potential utility in treating chronic myelogenous leukemia.

Additionally, individuals afflicted with chronic fatigue syndrome ("CFS") (also known as myalgic encephalomyelitis (ME) or low natural killer ("NK") cell disease) and other HHV-6 related disorders also display a highly elevated RNase L activity compared to controls (mean basal level= 466±23 compared to 123±12 in controls; p<0.0001), Suhadolnik et al, *Clinical Infectious Disease* 18 (*SUPPL.* 1): 96–104 (1994). In experiments performed using extracts of peripheral blood mononuclear cells ("PBMC") from individuals with CFS before and during therapy with a biological response modifier, poly (I)-poly ($C_{12}$U) (mismatched dsRNS, Ampligen®), as compared to healthy individuals, the mean basal latent 2-5A synthetase level in PMBC extracts was significantly decreased following therapy (610±220 picomoles 2-5A/mg protein/hour) compared to controls (2035±325 picomoles 2-5A/mg protein/hour, P<0.001). Id. Further, all pretherapy PBMC extracts tested were positive for human herpes virus-6 (HHV-6) replication. Therapy resulted in a significant decrease in HHV-6 activity (p<0.01) and down regulation of the 2-5A synthetase/RNase L pathway in temporal association with clinical and neuropsychological improvement. Without wishing to be bound by any theory, it appears that the upregulated 2-5A pathway observed in CFS pretherapy is consistent with a hypothesis that an activated immune state and persistent viral infection may play a pathogenesis of CFS. Thus, pApA$_{Sp}$*A, which, as stated above, is a metabolically stable inhibitor of RNase L, also has potential utility in treating CFS.

Inhibition of Cell Growth by Phosphorothioate/ Phosphodiester 2-5A Core Derivatives Cell viability was determined by Trypan blue exclusion. Post-treatment colony forming ability was determined by growth in microtiter wells as outlined in the procedure of Kraemer et al. *Mutation Res.* 72: 285–292 (1980). The results indicate that no decrease in survival or inhibition of Sup T1 cell growth in microtiter plates was observed with any of the dimer, trimer or tetramer phosphorothioate/ phosphodiester 2-5A core derivatives. On the basis of the lack of cytotoxicity and estimated uptake of 1% on a previous report with the cordycepin derivative of 2-5A, Suhadolnik et al., *Nucleosides and Nucleotides* 2: 351–366 (1983), $3 \times 10^{-4}$M was chosen as the concentration at which to screen the phosphorothioate/phosphodiester derivatives for anti-HIV-1 activity.

Effect of 2',5'-Phosphorothioate/Phosphodiester Oligoadenylates on Inhibition of HIV-1-Induced Syncytia Formation The infected centers assay as described by Henderson et al., *Virology* 182: 186–198 (1991), was used to measure the ability of the phosphorothioate/phosphodiester derivatives of 2-5A trimer and tetramer cores to inhibit HIV-1 induced syncytia formation, an indicator of HIV-1 replication in T cells. Freshly isolated peripheral blood lymphocytes (PBL) were treated with 2-5A or derivatives for 2 h and infected with HIV-1 strain IIIB at a m.o.i. of approximately 0.1. The infected PEL were maintained in RPMI-1640 medium supplemented with 10% (v/v) heat-inactivated fetal calf serum at 37° C. in a humidified 5% $CO_2$ in air atmosphere. After 48 h, the cells were washed twice in Hank's balaned salt solution, serially diluted and seeded into multiple wells of a 96-well microtiter plate. Immediately, $2 \times 10^5$ exponentially growing Sup T1 cells were added to each well; Sup T1 cells readily form a syncytium with a cell which is productively infected with HIV-1. The wells were examined daily for the presence of syncytia, using a tissue culture microscope. The first signs of syncytia formation can be seen in 12 h, with some complete syncytia developing by 24 h. Final results were read at 72 h. Each syncytium was counted as a single infected cell. The number of syncytia per seeded cell is determined and expressed as an infected center per infected cell. In the control (no 2-5A derivative added), 100% syncytia formation was equivalent to 12±3 syncytia per 200 HIV-1 infected cells.

Figure 5A:
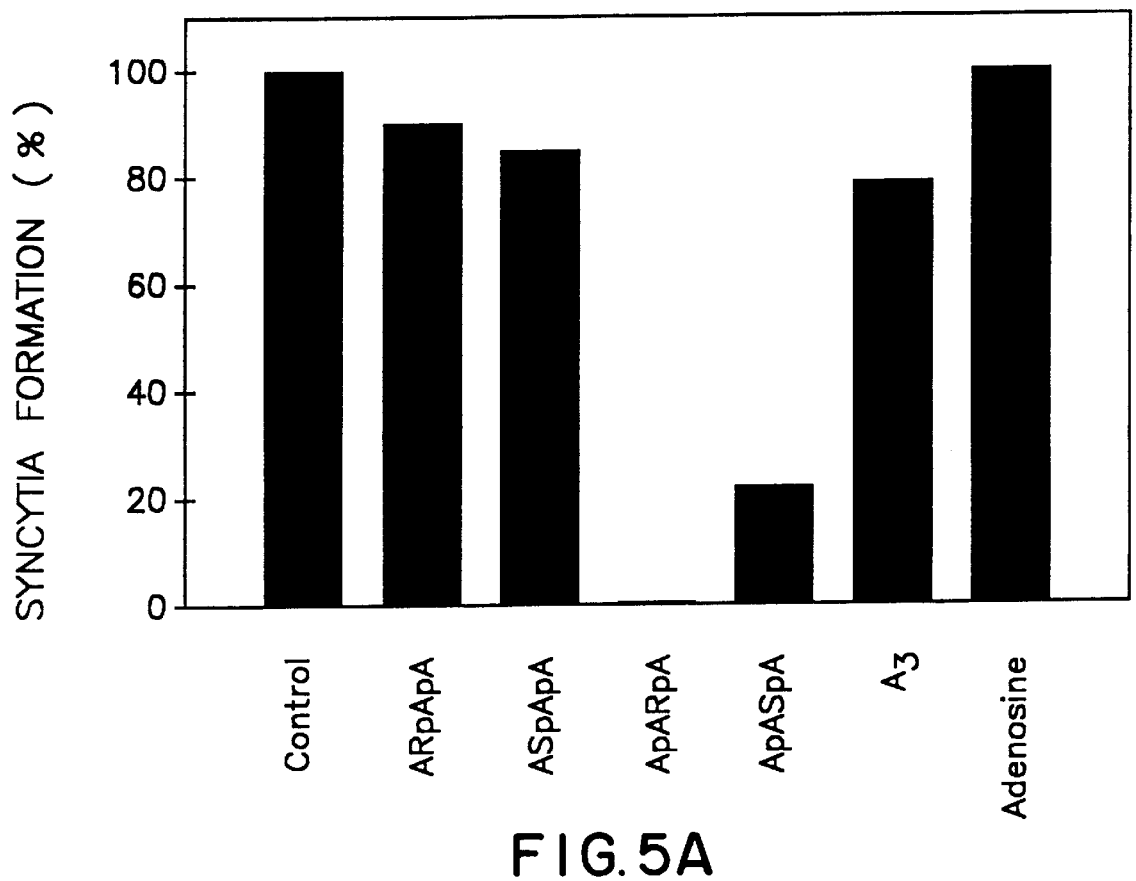
FIG. 5A represents the results of an assay performed according to the method of Henderson et al., *Virology* 182: 186–198 (1991), indicating the inhibition of HIV-1 (IIIB)-induced syncytia formation by adenosine, 2-5A trimer or tetramer core or 2',5'- phosphorothioate/phosphodiester trimer derivatives: A$_{Rp}$*ApA, A$_{Sp}$*ApA, ApA$_{Rp}$*A, ApA$_{Sp}$*A, A$_{Rp}$*ApApA, A$_{Sp}$*ApApA, ApA$_{Rp}$*ApA, ApA$_{Sp}$*ApA, ApApA$_{Rp}$*A, ApApA$_{Sp}$*A.
Figure 5B:
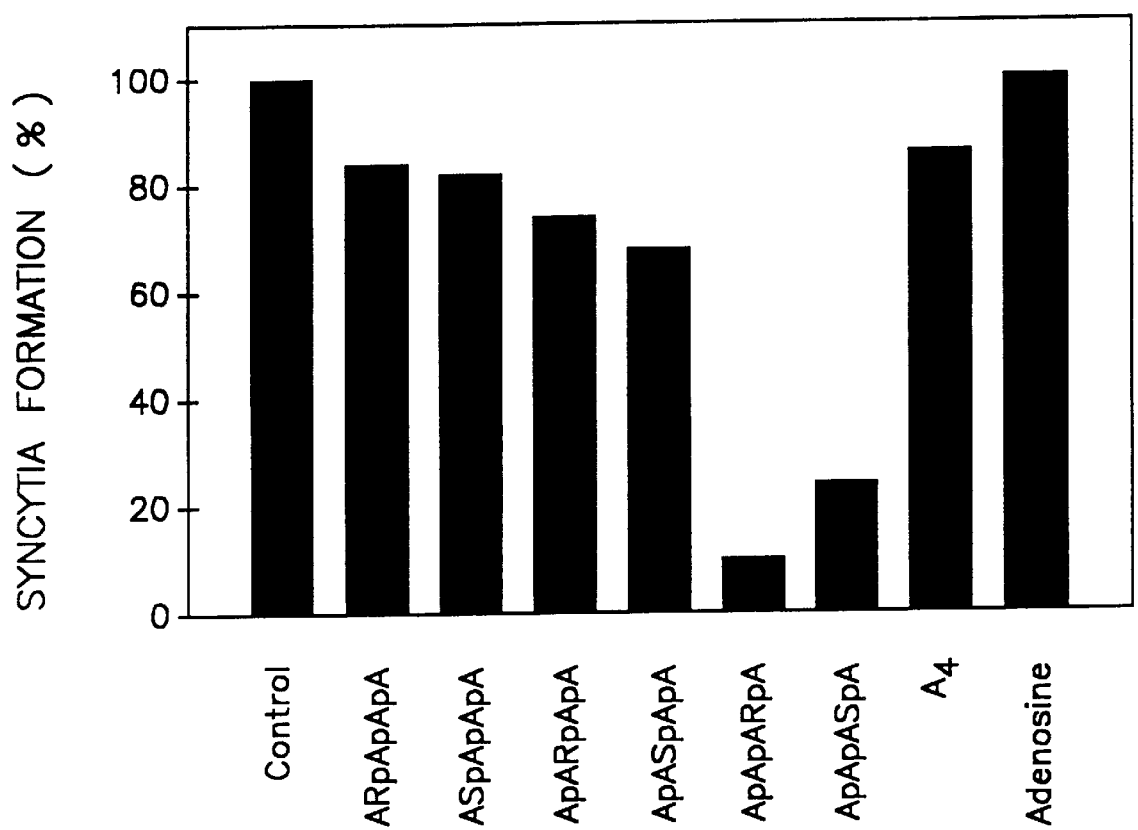
FIG. 5B is the results of an assay performed according to the method of FIG. 5A with a 2',5'-phosphorothioate/phosphodiester tetramer derivative of 2-5A core.

The data is shown in FIGS. 5A and 5B. As shown in FIG. 5A, ApA$_{Rp}$*A was a highly efficient inhibitor of syncytia formation, with 100% inhibition observed at $3 \times 10^{-4}$M. Its PS enantiomer, ApA$_{Sp}$*A inhibited syncytia formation 78%. A$_{Rp}$*ApA and A$_{Sp}$*ApA inhibited syncytia formation only 10% and 15%, respectively. Authentic A$_3$ and A$_4$ ($3 \times 10^{-4}$M) inhibited syncytia formation 21% and 15%, respectively while adenosine ($9 \times 10^{-4}$M) did not inhibit syncytia formation. Of the six phosphorothioate/phosphodiester tetramer core derivatives, ApApA$_{Rp}$*A and ApApA$_{Sp}$*A were the most inhibitory (90% and 76% inhibition, respectively) (FIG. 5B). ApA$_{Rp}$*ApA, ApA$_{Sp}$*ApA, A$_{Rp}$*ApApA and A$_{Sp}$*ApApA inhibited syncytia formation 26%, 32%, 16% and 18%, respectively. Adenosine and A$_4$ (FIG. 5B), as well as the A$_{Rp}$*A and A$_{Sp}$*A dimers, adenine or 3',5'-A$_4$ (data not shown), were not able to inhibit syncytia formation.

Effect of 2',5'-Phosphorothioate/Phosphodiester Oligoadenylates on HIV-1 Reverse Transcriptase Activity Sup T1 cells were treated with 2-5A or a phosphorothioate/phosphodiester derivative at 300 μM for 6 hours and then infected with HIV-1 at a multiplicity of infection (M.O.I) of approximately 0.1. Adenosine and adenine were tested at 900 μM. At 96 hours post-infection, culture supernatant was removed and HIV-1 RT activity was assayed in triplicate as described by Henderson et al., *Virology* 182:186–198 (1991). Briefly in this method, 25 μl of culture supernatant was added to a 50 μl cocktail containing 50 mM Tris (pH 8.0), 20 mM dithiothreitol, 10 mM MgCl$_2$, 60 mM NaCl, 0.05 Nonidet p-40, 5 μg/ml oligodeoxythymidylic acid, 10 μg/ml polyriboadenylic acid, 10 μM deoxythymidine triphosphate and 1 mCi [$^{32}$p]thymidine 5'-triphosphate. The mixture was incubated at 37° C. for 2 hours. Fifty microliters of the cocktail were then spotted onto diethylaminoethyl (DEAE) paper, dried, washed with 2x SSC solution (three times for 10 minutes each time) and 95% ethanol (two times for 5 minutes each time), dried and exposed to radiographic film for 18 to 24 hours at –80° C. The filters were cut and final quantitation was determined by scintillation spectrometry.

The data for the HIV-1 RT activity is shown in Table 2. As indicated, the trimer ApA$_{Sp}$*A was the most efficient inhibitor of HIV-1 RT activity (78%). On the contrary, its PR enantiomer, ApA$_{Rp}$*A inhibited HIV-1 reverse transcription by 31%. Similarly, the tetramer with the PS phosphorothioate/phosphodiester linkage adjacent to the 2' terminal linkage, ApApA$_{Sp}$*A, was able to suppress RT activity 62% while its PR counterpart was only 38% effective in inhibiting this activity.

TABLE 2

| Inhibition of HIV-1 Reverse Transcriptase Activity by Phosphorothioate/Phosphodiester 2–5A | |
|---|---|
| 2–5A or Derivative | Percent Inhibition of HIV-1 Reverse Transcriptase[1] |
| 2',5'-A$_{Rp}$*ApA | 32 |
| 2',5'-A$_{Sp}$*ApA | 56 |
| 2',5'-ApA$_{Rp}$*A | 31 |
| 2',5'-ApA$_{Sp}$*A | 78 |
| 2',5'-A$_{Rp}$*ApApA | 57 |
| 2',5'-A$_{Sp}$*ApApA | 54 |
| 2',5'-ApA$_{Rp}$*ApA | 52 |
| 2',5'-ApA$_{Sp}$*ApA | 42 |
| 2',5'-ApApA$_{Rp}$*A | 38 |
| 2',5'-ApApA$_{Sp}$*A | 62 |
| 2',5'-A$_4$ | 26 |
| 3',5'-A$_4$ | 8 |
| Adenosine | 0 |
| Adenine | 4 |

[1]Average of triplicate determinations. Intra-assay variation for replicates was <10%.

The compounds of the present invention may be combined with appropriate pharmaceutical or agricultural carriers to form an antiviral composition.

For pharmaceutical use, the compounds of the invention may be taken up in pharmaceutically acceptable carriers, such as, solutions, suspensions, tablets, capsules, ointments, elixirs and injectable composition and the like. They are administered to subjects suffering from viral infection. The dosage administered depends upon the nature and severity of the infection, the disease stage, and, when administered systematically, the size and weight of the infected subject.

The compounds are generally administered in the form of water-soluble salts. Pharmaceutically acceptable water soluble salts include, for example, the sodium, potassium or ammonium salts of the active compounds. They are readily dissolved in water or saline solution. Thus, the preferred formulation for pharmacological use comprises a saline solution of the desired compound in salt form. The formulation may further contain an agent, such as a sugar or protein, to maintain osmotic balance. The salt form of the compound is preferred owing to the relatively high acidity (about pH 3) of the acid form of the compounds.

The compounds of the invention may be used as a treatment or prophylactically for humans and animals from viral infectives such as Herpes simplex, rhinovirus, hepatitis and other infections of the hepatitis virus family, Epstein Barr virus, measles virus, multiple sclerosis (which may be caused by a viral agent) and the various Human T-Lymphotropic Viruses ("HTLV"), such as HTLV-1, which causes cutaneous T cell lymphoma, HTLV-2, which causes Sezary lymphoma, and HTLV-3, which is responsible for Acquired Immune Deficiency Syndrome ("AIDS"). The compounds of the invention inhibit the HIV-1 Induced Syncytia formation.

The compounds may be applied topically to treat skin cancers caused by radiation, carcinogens or viral agents. Such skin cancers include cutaneous T-cell lymphoma, Sezary lymphoma, Xeroderma pigmentosium, ataxia telangiectasia and Bloom's syndrome. A sufficient amount of a preparation containing a compound of the invention is applied to cover the lesion or affected area. An effective concentration of active agent is between about $10^{-3}$M and $10^{-5}$M, with $10^{-4}$M being preferred.

The compounds of the present invention may also be used to treat plant-infecting virus, particularly tobacco mosaic virus, and other viruses which cause necrosis in turnips, cucumber, orchids and in other plants. Such viruses include, but are not limited to, tobacco vein mottling virus, vesicular stomatitis virus, vaccinia virus, turnip necrosis virus, and cymbidium orchid virus.

The compounds may be administered effectively to plants by topical application by abrasion of the leaf surface, aerosol spray, treatment of the soil, spraying, or dusting.

An effective antiviral composition may be formed by combining one or more of the compounds of the invention with a carrier material suitable for agricultural use. While the individual stereoisomers are preferred for pharmaceutical use, mixtures of one or more of stereoisomers may be employed in agricultural applications. The active compound may also be administered by spraying insect vectors such as aphids, thrips and whiteflies which carry virus to plants. The dosage administered depends upon the severity of the infection.

The compounds of the invention may be applied to plant seeds prior to germination to control viruses contained in the germ plasm. The seeds may be soaked in a solution of polyethylene glycol ("PEG") containing one or more of the compounds. PEG brings the seeds to physiological activity and arrest. The relative concentration of active compound to PEG depends upon the type of seed under treatment.

Plants may be effectively treated with an aqueous formulation containing from about $10^{-1}$ to about $10^{-2}$M concentration of active ingredient. The compounds of the invention may be applied at very low concentrations. An effective amount of active ingredient on the plant surface is from about $10^{-8}$ to about $10^{-12}$ mole per $cm^2$ of being preferred. For the typical tobacco plant of 1,000 $cm^2$, $10^{-5}$M of compound is effective. At this rate, one pound of active ingredient is sufficient to treat $2\times10^8$ tobacco plants.

For agricultural application, the compounds are advantageously administered in the form of water-soluble salts, e.g. ammonium or potassium salts. Sodium salts are generally avoided in treating edible plants.

The compounds of the invention are readily dissolved in water, particularly at such low concentrations. Aqueous formulations for agricultural use may optionally contain a sticker and/or a UV-stabilizer. Such agents are well-known to those skilled in the art. Fatty acids (1%) are useful as spreader sticker agents. Effective UV-stabilizers include, for example, p-aminobenzoic acid.

For antiviral use in mammals, the compounds of the invention are administered parenterally, such as intravenously, intraarterially, intramuscularly, subcutaneously or when administered as an anti-cancer agent, intratumorally. The preferred route of administration for antiviral therapy is intravenous injection. The compounds of the invention may be administered to mammals at very low concentrations. The actual dosage administered may take into account the size and weight of the patient, whether the nature of the treatment is prophylactic or therapeutic in nature, the age, health and sex of the patient, the route of administration, the nature and stage of the affliction, and other factors. An effective daily dosage of active ingredient, based upon in vivo studies involving other 2-5A analogues, is from about 0.25 g per 70 kg of body weight (approximately 152 lbs) to about 2.5 g per 70 kg of body weight. The preferred daily dosage is about 0.5 g per 70 kg of body weight. Those skilled in the art should readily be able to derive appropriate dosages and schedules of administration to suit the specific circumstance and needs of the patient.

It is expected that an effective treatment regimen includes administration of the daily dosage for two days. Treatment is continued at least until the disease condition is substantially abated.

Preferably, the therapeutic end point is determined by testing for the continued presence of viral DNA. Such testing can be done by polymerase chain reaction (PCR) in which the presence of viral DNA is assayed according to convential PCR. PCR primers of appropriate nucleotide sequences for amplification of viral DNA can be prepared from known viral nucleotide sequences. To obtain DNA for testing, patient peripheral blood mononuclear cells are lysed with an appropriate lysing agent, such as NP-40.

Alternatively, testing for the continued presence of the virus can be performed by an antigen-antibody assay using any of the known monoclonal or polyclonal antisera against a protein antigen of the target virus' protein coat. For example, an antigen-antibody assay may be employed to detect any of the protein antigen in the antigens HIV protein coat, for example, the gp120, p17 or p24. Moreover, the target antigen is not limited merely to coat protein antigens. Antisera can be targeted against a suitable non-coat protein antigen, such as the HIV reverse transcriptase (RT) molecule. Monoclonal antibodies to HIV RT are known. Sobol et al., *Biochemistry* 30: 10623–10631 (1991).

Additionally, testing for the presence of the infecting virus during or post-treatment could be accomplished by an assay which assesses the viral load in the patient's blood stream. This can be done by determining the level of syncytia formation, i.e., by measuring the formation of viral particles. See procedure outlined in Henderson et al., *Virology* 182: 186–198 (1994).

In addition to administration with conventional carriers, the compounds of the present invention may be administered by a variety of specialized oligonucleotide or nucleic acid delivery techniques. 2-5A and its analogues have been successfully encapsulated in various encapsulating materials, such as in unilamellar liposomes and delivered with the aid of monoclonal antibodies to cells, Bayard et al., *Eur. J. Biochem.* 151:319–325 (1985). Reconstituted Sendai virus envelopes have been successfully used to deliver RNA and DNA to cells, Arad et al., *Biochem. Biophys. Acta.* 859: 88–94 (1986). Moreover, the virus envelope is not limited to Sendai virus, but could include encapsulation in any retroviral amphotrophic particle. For example, an HIV envelope could be formed from any part or all of the outer protein coat of a non-infectious HIV particle. Such particles as gp 120 can be cloned by known recombinant techniques. These techniques may be utilized for introduction of the present 2',5'-phosphorothioate/phosphodiester oligoadenylates into cells. It is further contemplated that the compounds of the invention may be administered in the form of prodrugs in which lipophilic groups are attached to, for example, the 5'-terminal hydroxyl group of the core compound.

Conjugation of 2',5'-Phosphorothioate Tetramer Adenylates

The 2',5'-phosphorothioate/phosphodiester tetramers of the invention may be conjugated with the carrier (poly)L-lysine. (Poly)L-lysine has been shown to be an effective vector for introducing 2',5'-oligoadenylates and analogues into intact cells. Bayard et al., *Biochemistry* 25: 3730–3736 (1986) Poly(L-lysine) conjugation to trimer molecules is not feasible, owing to the destruction of the 2-terminal ribosyl moiety and subsequent inactivation of the molecule. Conjugation to poly(L-lysine) permits efficient intracellular transport of the 2',5'-phosphorothioate/phosphodiester oligoadenylates of the invention, while preserving intact within the conjugate the trimer moiety believed necessary for good biological activity.

The conjugates are formed by introducing two aldehyde functions at the 2' end of the tetramer by periodate oxidation of the alpha-glycol group of the ribose residue. The resulting aldehyde groups are then randomly coupled to the epsilon-amino groups of lysine residues of poly(L-lysine) by Schiff base formation, and then reduced with sodium cyanoborohydride at pH 8.0. This procedure converts the 2',3'-terminal ribose ring into a morpholine structure. The poly(L-lysine) peptide preferably contains from about 60 to about 70 lysine residues. From about five to about ten of the lysine residues are coupled in this manner to tetramer moieties. The resulting 2',5'-phosphorothioate/phosphodiester/(poly)L-lysine conjugates may then be isolated by gel filtration chromatography on a Sephadex G-50 column.

The 2',5'-phosphorothioate/phosphodiester oligoadenylate poly(L-lysine) conjugates have the formula:

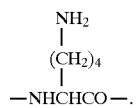

wherein q is an integer from about 60 to about 70 and each R is independently R' or

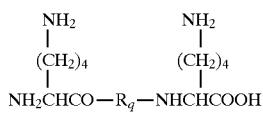

From about five to about ten of the R groups comprise R'. The R' group has the following formula:

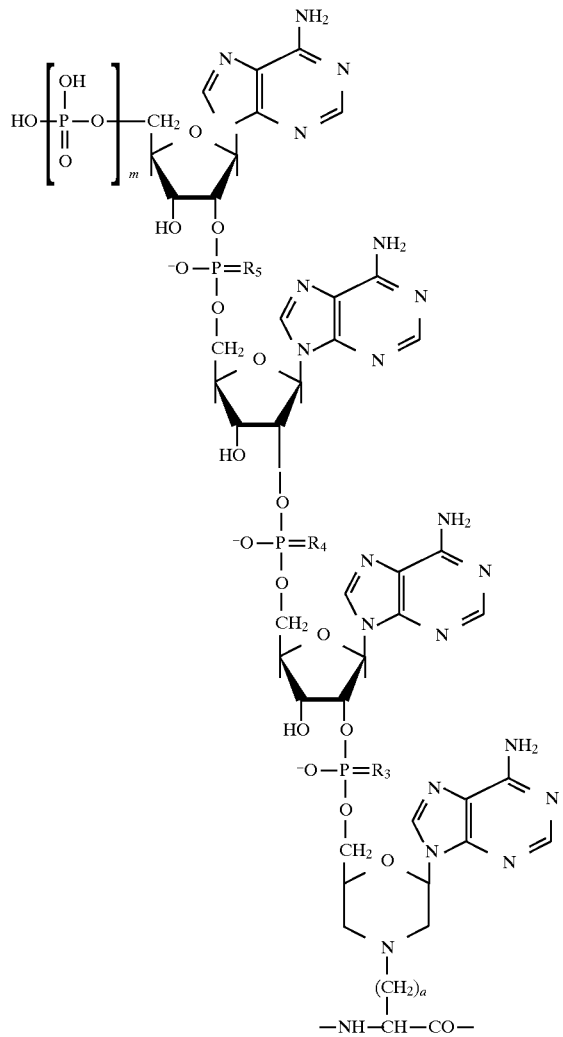

wherein m is zero, 1, 2 or 3; and $R_3$, $R_4$ and $R_5$ are independently selected from the group of oxygen and sulfur, provided that all $R_3$, $R_4$ and $R_5$ may not be oxygen, and further provided that all $R_3$, $R_4$ and $R_5$ may not be sulfur.

The conjugates may be advantageously prepared by the procedure of Bayard et al., *Biochemistry* 25: 3730–3736 (1986):

EXAMPLE 7

Preparation of Poly(L-lysine)/2',5'-Phosphorothioate/Phosphodiester Oligoadenylate Conjugates A 4-microliter aliquot of sodium metaperiodate (0.6 micromole in 0.1M sodium acetate buffer, pH 4.75) is added to an ice-cold solution of 2',5'-phosphorothioate/phosphodiester tetramer adenylate in 400 microliter of distiller water. The reaction mixture is stirred on ice for 30 min;

400 microliter of poly(L-lysine) (0.14 micromole in 0.2M phosphate buffer, pH 8.0) and 200 microliter of sodium cyanoborohydride (20 micromole in 0.2M phosphate buffer, pH 8.0) are added. The mixture is incubated for 2 h at room temperature and then loaded on a Sephadex G-50 column equilibrated with 0.1M sodium acetate buffer, pH 4.75. Each fraction is assayed for its phosphorothioate/phosphodiester oligoadenylate/poly(L-lysine) content by the method described by Lowry et al., *J. Biol. Chem.* 193:265–275 (1951), and by absorbance at 260 nm.

Conjugation of the 2',5'-phosphothioate/phosphodiester tetramer to poly(L-lysine) leaves the remaining three 2',5'-linked phosphorothioate/phosphodiester adenylic residues intact for optimal RNase L binding and activation.

Liposome Encapsulation of 2',5'Phosphorothioate/ phosphodiester Oligoadenylates

Encapsulation of the compounds of the present invention comprises another attractive non-disruptive technique for introduction into cells. Liposome encapsulation may be advantageously accomplished according to the technique described by Kondorosi et al., *FEBS Lett.* 120:37–40 (1980).

EXAMPLE 8

Preparation of Large Unilamellar Vesicles (Liposomes) Loaded with 2',5'-Phosphorothioate/ Phosphodiester Oligoadenylates Briefly, a phospholipid mixture from bovine brain (Sigma Chemical Co., Folch fraction III composed of 80–85% phosphatidylserine with the remaining 15% composed of other brain lipids; 35 mg) is suspended in 5 ml of buffer A [0.1M NaCl, 2 mM histidine, 2 mM N-tris(hydroxymethyl) methyl-2-aminoethane sulfonic acit ("TES"), 0.4 mM EDTA (pH 7.4) by vortexing. The suspension is sonicated under nitrogen for 10 minutes at 0° C. The suspension is further incubated for 1 hr at 37° C. after adjusting the final concentration of $Ca^{++}$ to 20 mM by the addition of 125 microliters of 800 mM $CaCl_2$. The resulting precipitate is sedimented by centrifugation (2500×g, 10 min), vortexing and mixing with 100 microliters of $1\times10^{-4}$M 2',5'-phosphorothioate/phosphodiester oligoadenylate, which is dissovled in phosphate-buffered saline. The final concentration of EDTA is then adjusted to 120 mM by the addition of 400 microliters of buffer B [150 mM EDTA, pH 7.4, 0.1M NaCl, 2 mM histidine, 2 mM TES]. Liposomes are formed after incubation of this mixture for 30 minutes at 37° C. The excess of EDTA and non-encapsulated components are removed by passing the liposomes through a Sephadex G-25 column which is equilibrated with phosphate-buffered saline. About 10% of the 2',5'-phosphorothioate/ phosphodiester oligoadenylate is encapsulated into liposomes by this procedure. The liposome suspension is stable at 4° C. for one week following preparation.

Preparation of Reconstituted Sendai Virus Envelopes Containing 2',5'-Phosphorothioate/ Phosphodiester Oligoadenylates Reconstituted Sendai virus envelopes may be used as efficient vehicles for the introduction of polynucleotides into cells. Arad et al., Biochimica et *Biophysica Acta* 859: 88–94 (1986), discloses introduction of poly(I) ●poly(C) into cultured cells by the use of reconstituted Sendai virus envelopes. Fusion of the aforesaid reconstituted Sendai virus envelopes leads to introduction of the enclosed macromolecules into the recipient cell cytoplasm. Reconstituted Sendai virus envelopes may be obtained by detergent solubilization of intact Sendai virus particles. The reconstituted envelopes are fusogenic vesicles consisting of the viral envelope phospholids and their glycoproteins, devoid of the viral genomic RNA.

Incorporation of the compounds of the present invention into reconstituted Sendai virus envelopes for fusion-mediated micro-injection may be accomplished by following the procedure of Arad et al., Biochimica et *Biophysica Acta* 859: 88–94 (1986). Briefly, a pellet of Sendai virus particles (1.5 mg protein) is dissolved in 30 microliters of a solution containing 10% Triton X-100, 100 mM NaCl, 50 mM Tris-HCl (pH 7.4) and 0.1 mM phenylmethylsulfonyl fluoride (Triton X-100:protein ratio, 2:1, w/w). To the clear supernatant obtained after centrifugation, 2',5'-phosphorothioate/phosphodiester oligoadenylate dissolved in a solution A (160 mM NaCl, 20 mM Tris-HCl (pH 7.4)) is added to give a final concentration of active ingredient of 5–20 mg/ml and a final volume of 150 microliters. Triton X-100 is removed from the supernatant by direct addition of 40 mg of SM-2 Bio-Beads. The turbid suspension obtained (containing reconstituted Sendai virus envelopes) is centrifuged at 100,000×g for 1 h. The pellet, containing about 10% of the original viral protein, is then suspended in solution A to give a final protein concentration of 25 micrograms/ml.

The present invention may be embodied in other specific forms without departing from the spirit or essential attributes thereof and, accordingly, reference should be made to the appended claims, rather than to the foregoing specification, as indicating the scope of the invention.

We claim:
1. A compound of the formula:

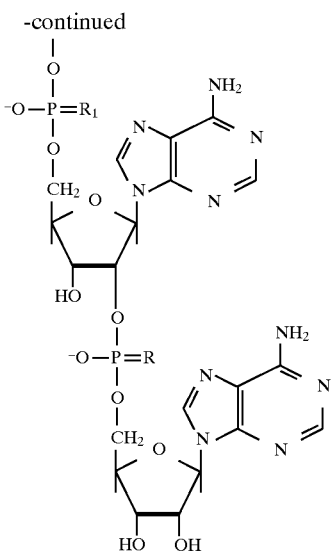

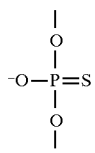

wherein m is zero, 1, 2 or 3; and R, $R_1$ and $R_2$ are independently selected from the group consisting of oxygen and sulfur, provided that all R, $R_1$ and $R_2$, may not be oxygen, and further provided that all R, $R_1$ and $R_2$ may not be sulfur; or water-soluble salt thereof.

2. A compound according to claim 1 wherein m is 1.

3. A compound according to claim 1 wherein m is 0.

4. A compound according to claim 1 selected from the group consisting of adenylyl-(2',5')-P-thioadenylyl-(2',5')-adenylyl-(2',5')-adenosine, the 5'-mono-, di-, and triphosphates thereof, and water-soluble salts of any of them.

5. A compound according to claim 1 selected from the group consisting of adenylyl-(2',5')-adenylyl-(2',5')-P-thioadenylyl-(2',5')-adenosine, the 5'-mono-, di-, and triphosphates thereof, and water-soluble salts of any of them.

6. A compound according to claim 1 selected from the group consisting of adenylyl-(2',5')-P-thioadenylyl-(2',5')-P-thioadenylyl-(2',5')-adenosine, the 5'-mono-, di-, and triphosphates thereof, and water-soluble salts of any of them.

7. An antiviral composition comprising a compound according to claim 1 in combination with a pharmaceutical or agricultural carrier.

8. An antiviral composition according to claim 7 wherein m is 1.

9. An antiviral composition according to claim 7 wherein the carrier comprises an encapsulating material selected from the group consisting of reconstituted Sendai virus envelope and liposome, which material encapsulates the compound.

10. A method of treating viral infection in a mammal comprising administering thereto an antiviral effective amount of a compound according to claim 1.

11. A method according to claim 10 wherein m is 1.

12. A pharmaceutical composition comprising a pharmaceutical carrier and a compound according to claim 1.

13. An isolated optical isomer according to claim 1, or water-soluble salt of such isolated isomer.

14. An isolated optical isomer according to claim 13 having one or two internucleotide phosphorothioate groups at least one of which is of the PR configuration.

15. An isomer according to claim 14 selected from the group consisting of adenylyl-(2',5')-(PR)-P-thioadenylyl-(2',5')-adenylyl-(2',5')-adenosine, the 5' mono-, di-, and triphosphates thereof, and water-soluble salts of any of them.

16. An isomer according to claim 13 selected from the group consisting of adenylyl-(2',5')-(PS)-P-thioadenylyl-(2',5')-adenylyl-(2',5')-adenosine, the 5' mono-, di-, triphosphates thereof, and water-soluble salts of any of them.

17. An isomer according to claim 14 selected from the group consisting of adenylyl-(2',5')-adenylyl-(2',5')-(PR)-P-thioadenylyl-(2',5')-adenosine, the 5' mono-, di-, and triphosphates thereof, and water-soluble salts of any of them.

18. An isomer according to claim 13 selected from the group consisting of adenylyl-(2',5')-adenylyl-(2',5')-(PS)-P-thioadenylyl-(2',5')-adenosine, the 5' mono-, di-, and triphosphates thereof, and water-soluble salts of any of them.

19. A method of treating viral infection in a mammal comprising administering thereto an antiviral effective amount of an isolated optical isomer according to claim 13.

20. A pharmaceutical composition comprising a pharmaceutical carrier and an isolated optical isomer according to claim 13.

21. A conjugate of poly(L-lysine) and a 2'-5' phosphorothioate/phosphodiester oligoadenylate, said conjugate having the formula $$\begin{array}{cc} NH_2 & NH_2 \\ | & | \\ (CH_2)_4 & (CH_2)_4 \\ | & | \\ NH_2CHCO-R_q-NHCHCOOH \end{array}$$

wherein q is an integer from about 60 to about 70 and each R is independently R' or $$\begin{array}{c} NH_2 \\ | \\ (CH_2)_4 \\ | \\ -NHCHCO- \end{array}$$.

provided from about five to about ten of the R groups are R', which R' has the following formula

47

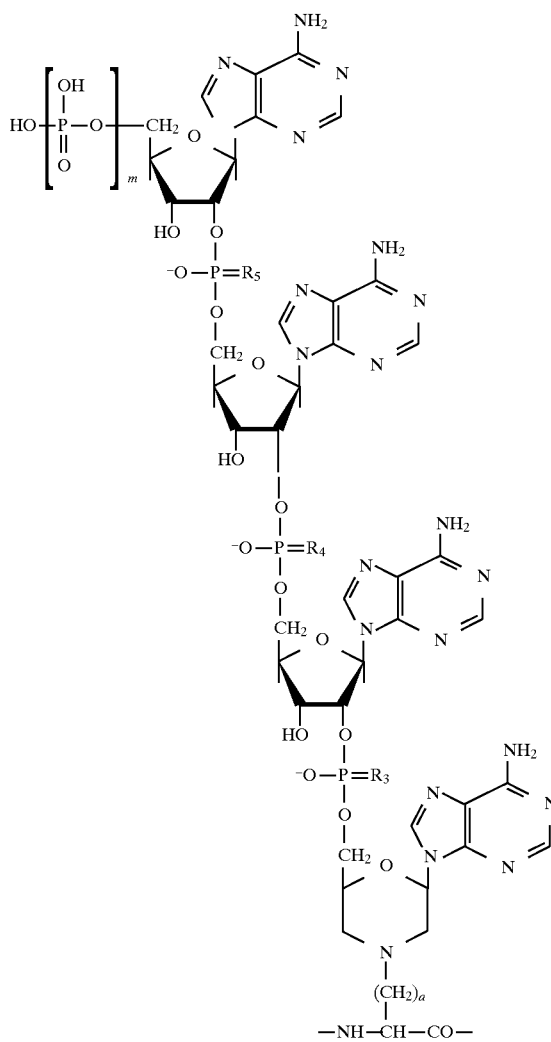

wherein m is zero, 1, 2, 3; and where $R_3$, $R_4$ and $R_5$, are independently selected from the group of oxygen and sulfur, provided that all $R_3$, $R_4$ and $R_5$ may not be oxygen, and further provided that all $R_3$, $R_4$ and $R_5$ may not be sulfur.

22. A method of treating viral infection in a plant comprising administering thereto an antiviral effective amount of a compound according to claim 1.

23. A method of treating viral infection in a plant comprising administering thereto an antiviral effective amount of a compound according to claim 2.

24. A method of treating viral infection in a plant comprising administering thereto an antiviral effective amount of an optical isomer according to claim 13.

25. A method according to claim 10 wherein the viral infection treated is infection by human immunodeficiency virus.

26. A method according to claim 19 wherein the viral infection treated is infection by human immunodeficiency virus.

48

27. A compound of the formula:

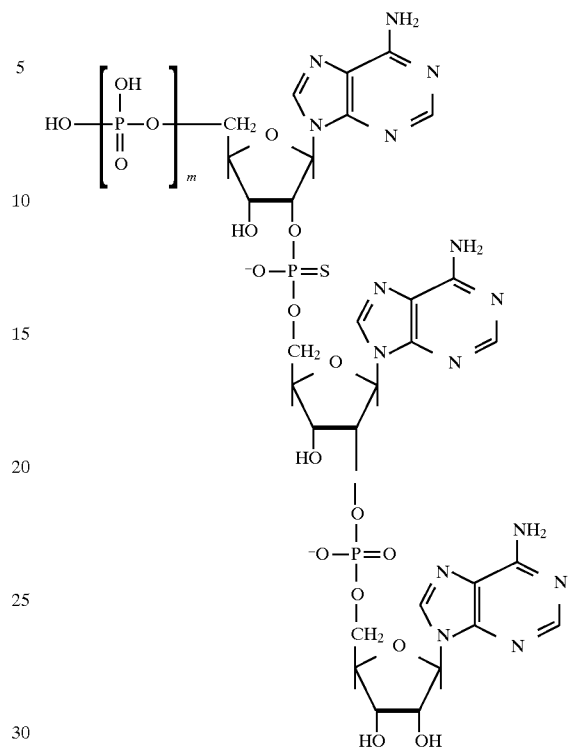

wherein m is zero, 1, 2 or 3; or water-soluble salt thereof.

28. An isomer according to claim 27 wherein m is 1.

29. An isomer according to claim 27 wherein m is 0.

30. An isolated optical isomer according to claim 27.

31. An antiviral composition comprising a compound according to claim 27 in combination with a pharmaceutical or agricultural carrier.

32. A method of treating viral infection in a plant comprising administering thereto an antiviral effective amount of a compound according to claim 27.

33. A method of treating viral infection in a mammal comprising administering thereto an antiviral effective amount of a compound according to claim 27.

34. A method according to claim 33 wherein the viral infection treated is infection by human immunodeficiency virus.

35. An antiviral composition comprising a pharmaceutical or agricultural carrier in combination with a compound of the formula

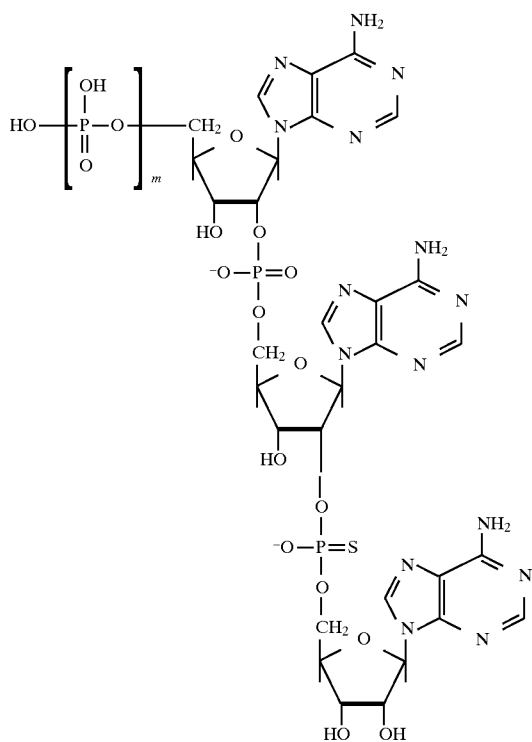

wherein m is zero, 1, 2 or 3; or water-soluble salt thereof.

36. A composition according to claim 35 wherein m is 1.

37. A composition according to claim 35 wherein m is 0.

38. A composition according to claim 35 wherein the compound is an isolated optical isomer.

39. A composition according to claim 38 wherein the optical isomer is selected from the group consisting of adenylyl-(2',5')-(PS)-P-thioadenylyl-(2',5')adenosine, the 5' mono-, di-, and triphosphates thereof, and water-soluble salts of any of them.

40. A composition according to claim 39 wherein the optical isomer is adenylyl-(2',5')-(PS)-P-thioadenylyl-(2',5') adenosine, or water-soluble salt thereof.

41. A composition according to claim 38 wherein the optical isomer is selected from the group consisting of adenylyl-(2',5')-(PR)-P-thioadenylyl-(2',5')adenosine, the 5' mono-, di-, and triphosphates thereof, and water-soluble salts of any of them.

42. A composition according to claim 41 wherein the optical isomer is adenylyl-(2',5')-(PR)-P-thioadenylyl-(2',5') adenosine, or water-soluble salt thereof.

43. A method of treating viral infection in a plant comprising administering thereto an antiviral effective amount of a composition according to claim 35.

44. A method of treating viral infection in a mammal comprising administering thereto an antiviral effective amount of a composition according to claim 35.

45. A method of treating viral infection in a mammal according to claim 44 wherein the compound contained in the composition is adenylyl-(2',5')-(PS)-P-thioadenylyl-(2', 5')adenosine, or water-soluble salt thereof.

46. A method of treating viral infection in a mammal according to claim 44 wherein the compound contained in the composition is adenylyl-(2',5')-(PR)-P-thioadenylyl-(2', 5')adenosine, or water-soluble salt thereof.

47. A method according to claim 44 wherein the viral infection treated is infection by human immunodeficiency virus.

48. A method of treating viral infection in a mammal comprising administering thereto an antiviral effective amount of a composition according to claim 20.

* * * * *